(12) United States Patent
Palli et al.

(10) Patent No.: US 8,822,754 B2
(45) Date of Patent: Sep. 2, 2014

(54) ECDYSONE RECEPTOR-BASED INDUCIBLE GENE EXPRESSION SYSTEM

(75) Inventors: Subba Reddy Palli, Lansdale, PA (US); Marianna Zinovjevna Kapitskaya, North Wales, PA (US); Dean Ervin Cress, Sounderton, PA (US)

(73) Assignee: Intrexon Corporation, Blacksburg, VA (US)

(*) Notice: Subject to any disclaimer, the term of this patent is extended or adjusted under 35 U.S.C. 154(b) by 0 days.

(21) Appl. No.: 13/463,527

(22) Filed: May 3, 2012

(65) Prior Publication Data

US 2012/0322148 A1 Dec. 20, 2012

Related U.S. Application Data

(63) Continuation of application No. 12/818,034, filed on Jun. 17, 2010, now Pat. No. 8,202,718, which is a continuation of application No. 11/841,495, filed on Aug. 20, 2007, now Pat. No. 7,776,587, which is a continuation of application No. 11/677,968, filed on Feb. 22, 2007, now Pat. No. 7,807,417, which is a continuation of application No. 10/239,134, filed as application No. PCT/US01/09050 on Mar. 21, 2001, now abandoned.

(60) Provisional application No. 60/191,355, filed on Mar. 22, 2000, provisional application No. 60/269,799, filed on Feb. 20, 2001.

(51) Int. Cl.
*A01K 67/00* (2006.01)
*A01K 67/033* (2006.01)
*A01K 67/027* (2006.01)

(52) U.S. Cl.
USPC .............................................................. 800/8

(58) Field of Classification Search
CPC ..................... A01K 2217/00; A01K 2217/052
USPC ............. 800/8, 13, 14, 15, 16, 17, 18, 19, 20; 435/69.1, 252.3
See application file for complete search history.

(56) References Cited

U.S. PATENT DOCUMENTS

| | | |
|---|---|---|
| 4,631,211 A | 12/1986 | Houghten |
| 4,859,609 A | 8/1989 | Dull et al. |
| 4,954,655 A | 9/1990 | Kelly |
| 4,981,784 A | 1/1991 | Evans et al. |
| 4,985,461 A | 1/1991 | Hsu et al. |
| 5,010,175 A | 4/1991 | Rutter et al. |
| 5,071,773 A | 12/1991 | Evans et al. |
| 5,117,057 A | 5/1992 | Hsu et al. |
| 5,171,671 A | 12/1992 | Evans et al. |
| 5,225,443 A | 7/1993 | Murphy et al. |
| 5,283,173 A | 2/1994 | Fields et al. |
| 5,378,726 A | 1/1995 | Yanagi et al. |
| 5,424,333 A | 6/1995 | Wing |
| 5,429,952 A | 7/1995 | Garner et al. |
| 5,459,127 A | 10/1995 | Felgner et al. |
| 5,514,578 A | 5/1996 | Hogness et al. |
| 5,530,021 A | 6/1996 | Yanagi et al. |
| 5,530,028 A | 6/1996 | Lidert et al. |
| 5,599,904 A | 2/1997 | Evans et al. |
| 5,639,616 A | 6/1997 | Liao et al. |
| 5,641,652 A | 6/1997 | Oro et al. |
| 5,668,175 A | 9/1997 | Evans et al. |
| 5,688,691 A | 11/1997 | Oro et al. |
| 5,710,004 A | 1/1998 | Evans et al. |
| 5,723,329 A | 3/1998 | Mangelsdort et al. |
| 5,789,214 A | 8/1998 | Ryals et al. |
| 5,880,333 A * | 3/1999 | Goff et al. ..................... 800/288 |
| 5,891,698 A | 4/1999 | Prieto et al. |
| 5,919,667 A | 7/1999 | Gage et al. |
| 5,939,442 A | 8/1999 | Evans et al. |
| 5,989,863 A | 11/1999 | Tang et al. |
| 6,004,941 A | 12/1999 | Bujard et al. |
| 6,013,836 A | 1/2000 | Hsu et al. |
| 6,025,483 A | 2/2000 | Yanofsky |
| 6,096,787 A | 8/2000 | Evans et al. |
| 6,107,543 A | 8/2000 | Sims et al. |
| 6,117,639 A | 9/2000 | Germann et al. |
| 6,147,276 A | 11/2000 | Campbell et al. |
| 6,147,282 A | 11/2000 | Goff et al. |
| 6,214,620 B1 | 4/2001 | Johns et al. |

(Continued)

FOREIGN PATENT DOCUMENTS

| | | |
|---|---|---|
| CN | 1313276 | 9/2001 |
| CN | 1313276 A | 9/2001 |

(Continued)

OTHER PUBLICATIONS

Capecchi et al., Altering the genome by homologous recombination Science vol. 244 No. 4910 pp. 1288-1292 Jun. 16, 1989.*
No et al Proc Natl Acad Sci U S A. Apr. 16, 1996;93(8):3346-51. Ecdysone-inducible gene expression in mammalian cells and transgenic mice.*
Sanders Williamset al., Transgenic animals in integrative biology: approaches and interpretations of outcome. Appl Physiol 88: 1119-1126, 2000.*
Kaufman et al Transgenic Analysis of a 100-kb Human β-Globin Cluster—Containing DNA Fragment Propagated as a Bacterial Artificial Chromosome Blood 94: 3178-3184, 1999.*
Moreadith RW,Gene targeting in embryonic stem cells: the new physiology and metabolism. J Mol Med. Mar. 1997;75(3):208-16.*
Wigley et al. Site-specific transgene insertion: an approach Reprod Fert Dev 6: 585-588, 1994.*

(Continued)

*Primary Examiner* — Maria Leavitt
(74) *Attorney, Agent, or Firm* — Sterne, Kessler, Goldstein & Fox P.L.L.C.

(57) ABSTRACT

This invention relates to the field of biotechnology or genetic engineering. Specifically, this invention relates to the field of gene expression. More specifically, this invention relates to a novel inducible gene expression system and methods of modulating gene expression in a host cell for applications such as gene therapy, large scale production of proteins and antibodies, cell-based high throughput screening assays, functional genomics and regulation of traits in transgenic plants and animals.

18 Claims, 6 Drawing Sheets

(56) References Cited

U.S. PATENT DOCUMENTS

| | | |
|---|---|---|
| 6,235,969 B1 | 5/2001 | Stice et al. |
| 6,245,531 B1 | 6/2001 | Hogness et al. |
| 6,258,603 B1 | 7/2001 | Carlson et al. |
| 6,265,173 B1 | 7/2001 | Evans et al. |
| 6,281,330 B1 | 8/2001 | Evans et al. |
| 6,300,488 B1 | 10/2001 | Gage et al. |
| 6,326,166 B1 | 12/2001 | Pomerantz et al. |
| 6,333,318 B1 | 12/2001 | Evans et al. |
| 6,410,245 B1 | 6/2002 | Northrop et al. |
| 6,458,926 B1 | 10/2002 | Evans et al. |
| 6,504,082 B1 | 1/2003 | Albertsen et al. |
| 6,635,429 B1 | 10/2003 | Leid et al. |
| 6,723,531 B2 | 4/2004 | Evans et al. |
| 6,756,491 B2 | 6/2004 | Evans et al. |
| 6,939,711 B2 | 9/2005 | Goff et al. |
| 7,038,022 B1 | 5/2006 | Evans et al. |
| 7,045,315 B2 | 5/2006 | Evans et al. |
| 7,057,015 B1 | 6/2006 | Gage et al. |
| 7,091,038 B2 * | 8/2006 | Palli et al. ............. 435/320.1 |
| 7,119,077 B1 | 10/2006 | Evans et al. |
| 7,183,061 B2 | 2/2007 | Jepson et al. |
| 7,456,315 B2 | 11/2008 | Hormann et al. |
| 7,531,326 B2 * | 5/2009 | Kapitskaya et al. ......... 435/69.7 |
| 7,776,587 B2 | 8/2010 | Palli et al. |
| 7,807,417 B2 | 10/2010 | Palli et al. |
| 7,935,510 B2 | 5/2011 | Palli et al. |
| 8,076,454 B2 | 12/2011 | Palli et al. |
| 8,105,825 B2 | 1/2012 | Dhadialla et al. |
| 8,115,059 B1 | 2/2012 | Palli et al. |
| 8,168,426 B2 | 5/2012 | Dhadialla et al. |
| 8,202,718 B2 | 6/2012 | Palli et al. |
| 8,236,556 B2 | 8/2012 | Kapitskaya et al. |
| 2002/0110861 A1 | 8/2002 | Dhadialla et al. |
| 2002/0119521 A1 | 8/2002 | Palli et al. |
| 2004/0033600 A1 | 2/2004 | Palli et al. |
| 2004/0096942 A1 | 5/2004 | Palli et al. |
| 2004/0197861 A1 | 10/2004 | Palli et al. |
| 2004/0235097 A1 | 11/2004 | Zhang et al. |
| 2005/0266457 A1 | 12/2005 | Palli et al. |
| 2006/0100416 A1 | 5/2006 | Palli et al. |
| 2007/0161086 A1 | 7/2007 | Palli et al. |
| 2007/0300313 A1 | 12/2007 | Palli et al. |
| 2008/0064097 A1 | 3/2008 | Palli et al. |
| 2008/0115237 A1 | 5/2008 | Palli et al. |
| 2008/0145935 A1 | 6/2008 | Palli et al. |
| 2008/0176280 A1 | 7/2008 | Kapitskaya et al. |
| 2008/0216184 A1 | 9/2008 | Palli et al. |
| 2008/0235816 A1 | 9/2008 | Dhadialla et al. |
| 2008/0263687 A1 | 10/2008 | Kapitskaya et al. |
| 2008/0301825 A1 | 12/2008 | Palli et al. |
| 2010/0275281 A1 | 10/2010 | Dhadialla et al. |
| 2011/0059525 A1 | 3/2011 | Palli et al. |
| 2011/0059530 A1 | 3/2011 | Palli et al. |
| 2012/0167239 A1 | 6/2012 | Palli et al. |
| 2012/0185954 A1 | 7/2012 | Palli et al. |
| 2013/0117872 A1 | 5/2013 | Palli et al. |
| 2013/0232588 A1 | 9/2013 | Kapitskaya et al. |
| 2013/0244330 A1 | 9/2013 | Palli et al. |
| 2013/0267023 A1 | 10/2013 | Dhadialla et al. |
| 2013/0286156 A1 | 10/2013 | Dhadialla et al. |

FOREIGN PATENT DOCUMENTS

| | | |
|---|---|---|
| EP | 234994 A1 | 1/1987 |
| EP | 234994 A1 | 1/1987 |
| EP | 461 809 A1 | 12/1991 |
| EP | 461809 A1 | 12/1991 |
| EP | 798378 A2 | 3/1997 |
| EP | 798378 B1 | 3/1997 |
| EP | 965644 A2 | 6/1999 |
| EP | 965644 A2 | 6/1999 |
| EP | 1266015 B1 | 3/2001 |
| WO | WO8912690 A1 | 12/1989 |
| WO | WO9200252 A1 | 1/1992 |
| WO | WO9428028 A1 | 12/1994 |
| WO | WO9518863 A1 | 7/1995 |
| WO | WO9521931 A1 | 8/1995 |
| WO | WO9637609 A1 | 5/1996 |
| WO | WO9617823 A1 | 6/1996 |
| WO | WO9625508 A1 | 8/1996 |
| WO | 9627673 A1 | 9/1996 |
| WO | WO9735985 A1 | 3/1997 |
| WO | WO9738117 A1 | 3/1997 |
| WO | 9738117 A1 | 10/1997 |
| WO | WO9833162 A1 | 1/1998 |
| WO | WO 98/35550 | 8/1998 |
| WO | WO9910510 A3 | 8/1998 |
| WO | WO9902683 A1 | 1/1999 |
| WO | WO9910510 A2 | 3/1999 |
| WO | WO9951777 A2 | 4/1999 |
| WO | WO9951777 A3 | 4/1999 |
| WO | WO 99/26966 | 6/1999 |
| WO | WO9927365 A1 | 6/1999 |
| WO | WO 99/36520 | 7/1999 |
| WO | WO9936520 A1 | 7/1999 |
| WO | WO9936520 A1 | 7/1999 |
| WO | 9958155 A1 | 11/1999 |
| WO | WO 01/02436 A1 | 1/2001 |
| WO | WO0170816 A2 | 3/2001 |
| WO | 0136447 | 5/2001 |
| WO | 0162780 | 8/2001 |
| WO | 02029075 A2 | 4/2002 |
| WO | WO 02/29075 | 4/2002 |
| WO | WO02029075 A2 | 4/2002 |
| WO | WO02066612 A2 | 8/2002 |
| WO | WO02066613 A2 | 8/2002 |
| WO | WO02066614 A2 | 8/2002 |
| WO | WO02066615 A2 | 8/2002 |
| WO | WO03105849 A1 | 6/2003 |
| WO | WO2004005478 A2 | 1/2004 |
| WO | WO2004072254 A2 | 2/2004 |
| WO | WO2004078924 A2 | 2/2004 |
| WO | WO2005017126 A2 | 2/2005 |
| WO | WO2005108617 A2 | 11/2005 |
| WO | WO2006083253 A1 | 8/2006 |

OTHER PUBLICATIONS

Keefer, Production of bioproducts through the use of transgenic animal models. Anim Reprod Sci. Jul. 2004;82-83:5-12. Review.*

Sigmund. Viewpoint: are studies in genetically altered mice out of control? Arterioscler Thromb Vasc Biol. Jun. 2000:20(6)1425- 9. Review.*

Wang et al. Rapid analysis of gene expression (RAGE) facilitates universal expression profiling (Nuc. Acids Res. 27: 4609- 4618, 1999; p. 4617).*

Mullins et al., 1993, Hypertension,Transgenesis in Nonmurine Species 1993;22;630-633.*

Houdebine, L, The methods to generate transgenic animals and to control transgene expression(2002, Journal of Biotechnology, vol. 98, p. 145-160).*

Cameron, 1977, Recent advances in transgenic technology pp. 253-265.*

1992, Kappell et al., Current Opinions in Biotechnology, p. 549, col. 1 and 2;).*

Billas et al., Vitam Horm. 2005;73:101-29. Ligand-binding pocket of the ecdysone receptor.*

Kolb et al., Insertion of a foreign gene into the b-casein locus by Cre-mediated site-specific recombination Gene 227 (1999) 21-31.*

Machida et al., P23H Rhodopsin Transgenic Rat: Correlation of Retinal Function with Histopathology Invest. Ophthalmol. Vis. Sci. Sep. 2000 vol. 41 No. 10 3200-3209.*

Non final office action for parent U.S. Appl. No. 10/239,134, filed Aug. 22, 2006.*

Horwitz KB et al., Nuclear receptor coactivators and corepressors, Mol Endocrinol, (1996), 10:1167-77. Endocrine Society, United States.

Kim JS et al., Design of TATA box-binding protein/zinc finger fusions for targeted regulation of gene expression, Proc Natl Acad Sci U S A, (1997), 94:3616-20. National Academy of Sciences, United States.

(56) References Cited

OTHER PUBLICATIONS

Kirken RA et al., Two discrete regions of interleukin-2 (IL2) receptor beta independently mediate IL2 activation of a PD98059/rapamycin/wortmannin-insensitive Stat5a/b serine kinase, J Biol Chem, (1997), 272:15459-65. American Society for Biochemistry and Molecular Biology, United States.

Nakagawa Y et al., Quantitative structure-activity studies of insect growth regulators: XIX: Effects of substituents on the aromatic moiety of dibenzoylhydrazines on larvicidal activity against the beet armyworm *Spodoptera exigua.* , Pest Management Science, (2002), 58:131-138, Wiley, United Kingdom.

O'Brien RM et al., Structural and functional analysis of the human phosphoenolpyruvate carboxykinase gene promoter, Biochim Biophys Acta, (1995), 1264:284-8., Elsevier Pub. Co., Netherlands.

Peet DJ et al., Engineering novel specificities for ligand-activated transcription in the nuclear hormone receptor RXR, Chem Biol, (1998), 5:13-21. Cell Press, United States.

Pierce AC et al., Computational Binding Studies of Orthogonal Cyclosporin-Cyclophilin Pairs, Angewandte Chemie International Edition in English, (1997), 36:1466-69.

Spencer DM et al., Controlling signal transduction with synthetic ligands, Science, (1993), 262:1019-24. American Assoc. for the Advancement of Science, United States.

Swevers L et al., The silkmoth homolog of the *Drosophila* ecdysone receptor (B1 isoform): cloning and analysis of expression during follicular cell differentiation, Insect Biochem Mol Biol, (1995), 25:857-66, Elsevier, Netherlands.

Trisyono A et al., Effect of the nonsteroidal ecdysone agonists, methoxyfenozide and tebufenozide, on the European Corn Borer (Lepidoptera: Pyralidae), J Economic Entomology, (1997), 90:1486-1492., Entomological Society of America, United States.

Wing KD, RH 5849, a nonsteroidal ecdysone agonist: effects on a *Drosophila* cell line, Science, (1988), 241:467-9., American Assoc. for the Advancement of Science, United States.

Wipf P et al., Combinatorial synthesis and biological evaluation of library of small-molecule Ser/Thr-protein phosphatase inhibitors, Bioorg Med Chem, (1997), 5:165-77, Elsevier Science, United Kingdom.

Wurm FM et al., Inducible overproduction of the mouse c-myc protein in mammalian cells, Proc Natl Acad Sci U S A, (1986), 83:5414-8, National Academy of Sciences, United States.

Zhang X et al., Study on synthesis and bioactivity of new diacylhydrazine IGR JS118, Nongyao, (2003), 42:18-20.

Egea PF et al. "Effects of ligand binding on the association properties and conformation in solution of retinoic acid receptors RXR and RAR," Mol Endocrinol. May 2002;16(5):987-97, Endocrine Society, United States.

Shea C et al., "An rxr/usp homolog from the parasitic nematode, *Dirofilaria immitis*." Gene. Jan. 7, 2004;324:171-82., Elsevier, Netherlands.

Bonneton F; et al. "Rapid divergence of the ecdysone receptor in Diptera and Lepidoptera suggests coevolution between ECR and USP-RXR." Mol Biol Evol. Apr. 2003;20(4):541-53., Oxford University Press, United Kingdom.

Hayward DC; et al. "The structure of the USP/RXR of *Xenos pecki* indicates that Strepsiptera are not closely related to Diptera." Dev Genes Evol. Apr. 2005;215(4):213-9, Springer-Verlag, Germany.

Moradpour D et al. "Independent regulation of two separate gene activities in a continuous human cell line."Biol. Chem. Aug.-Sep. 1998;379(8-9):1189-91., Walter De Gruyter, Germany.

International Search Report dated Feb. 22, 2007.

Antoniewski C et al., The ecdysone response enhancer of the Fbp1 gene of *Drosophila melanogaster* is a direct target for the EcR/USP nuclear receptor, Mol Cell Biol, (1994), 14:4465-74, American Society for Microbiology, United States.

Ashburner M et al., Temporal control of puffing activity in polytene chromosomes, Cold Spring Harb Symp Quant Biol, (1974), 38:655-62, Cold Spring Harbor Press, United States.

Cherbas L et al., Identification of ecdysone response elements by analysis of the *Drosophila* Eip28/29 gene, Genes Dev, (1991), 5:120-31, Cold Spring Harbor Press, United States.

Cho WL et al., Mosquito ecdysteroid receptor: analysis of the cDNA and expression during vitellogenesis, Insect Biochem Mol Biol, (1995), 25:19-27, Elsevier, Netherlands.

Chung AC et al., Cloning of crustacean ecdysteroid receptor and retinoid-X receptor gene homologs and elevation of retinoid-X receptor mRNA by retinoic acid, Mol Cell Endocrinol, (1998), 139:209-27., North Holland Publishing, Netherlands.

D'Avino PP et al., The moulting hormone ecdysone is able to recognize target elements composed of direct repeats, Mol Cell Endocrinol, (1995), 113:1-9, North Holland Publishing, Netherlands.

Dhadialla TS et al., New insecticides with ecdysteroidal and juvenile hormone activity, Annu Rev Entomol, (1998), 43:545-69, Annual Reviews, Inc., United States.

Evans RM, The steroid and thyroid hormone receptor superfamily, Science, (1988), 240:889-95, American Assoc. for the Advancement of Science, United States.

Fujiwara H et al., Cloning of an ecdysone receptor homolog from *Manduca sexta* and the developmental profile of its mRNA in wings, Insect Biochem Mol Biol, (1995), 25:845-56., Elsevier, Netherlands.

Godowski PJ et al., Signal transduction and transcriptional regulation by glucocorticoid receptor-LexA fusion proteins, Science, (1988), 241:812-6, American Assoc. for the Advancement of Science, United States.

Guo X et al., Isolation of a functional ecdysteroid receptor homologue from the ixodid tick *Amblyomma americanum* (L.), Insect Biochem Mol Biol, (1997), 27:945-62, Elsevier, Netherlands.

Hannan GN et al., Cloning and characterization of LcEcR: a functional ecdysone receptor from the sheep blowfly *Lucilia cuprina*, Insect Biochem Mol Biol, (1997), 27:479-88, Elsevier, Netherlands.

Heberlein U et al., Characterization of *Drosophila* transcription factors that activate the tandem promoters of the alcohol dehydrogenase gene, Cell, (1985), 41:965-77; Cell Press, United States.

Imhof MO et al., Cloning of a *Chironomus tentans* cDNA encoding a protein (cEcRH) homologous to the *Drosophila melanogaster* ecdysteroid receptor (dEcR), Insect Biochem Mol Biol, (1993), 23:115-24, Elsevier, Netherlands.

Kothapalli R et al., Cloning and developmental expression of the ecdysone receptor gene from the spruce budworm, *Choristoneura fumiferana*, Dev Genet, (1995), 17:319-30, Elsevier, United States.

Licitra EJ et al., A three-hybrid system for detecting small ligand-protein receptor interactions, Proc Natl Acad Sci U S A, (1996), 93:12817-21, National Academy of Sciences, United States.

Martinez A et al., Transcriptional activation of the cloned *Heliothis virescens* (Lepidoptera) ecdysone receptor (HvEcR) by muristeroneA, Insect Biochem Mol Biol, (1999), 29:915-30., Elsevier, Netherlands.

Morrison DA et al., Isolation of transformation-deficient *Streptococcus pneumoniae* mutants defective in control of competence, using insertion-duplication mutagenesis with the erythromycin resistance determinant of pAM beta 1, J Bacteriol, (1984), 159:870-6, American Society for Microbiology, United States.

Mouillet JF et al., Cloning of two putative ecdysteroid receptor isoforms from *Tenebrio molitor* and their developmental expression in the epidermis during metamorphosis, Eur J Biochem, (1997), 248:856-63., Blackwell, United Kingdom.

Neuberger MS et al., Recombinant antibodies possessing novel effector functions, Nature, (1984), 312:604-8, Nature Publishing, United Kingdom.

Riddiford LM et al., Ecdysone receptors and their biological actions, Vitam Horm, (2000), 60:1-73., Academic Press, United States.

Saleh DS et al., Cloning and characterization of an ecdysone receptor cDNA from *Locusta migratoria*, Mol Cell Endocrinol, (1998), 143:91-9., North Holland Publishing, Netherlands.

Srini C. Perera MSPJKARTSDSRP, An analysis of ecdysone receptor domains required for heterodimerization with ultraspiracle, Archives of Insect Biochemistry and Physiology, (1999), 41:61-70, Wiley-Liss, United States.

(56) References Cited

OTHER PUBLICATIONS

Suhr ST et al., High level transactivation by a modified *Bombyx* ecdysone receptor in mammalian cells without exogenous retinoid X receptor, Proc Natl Acad Sci U S A, (1998), 95:7999-8004., National Academy of Sciences, United States.

Swevers L et al., The silkmoth homolog of the *Drosophila* ecdysone receptor (B1 isoform): cloning and analysis of expression during follicular cell differentiation, Insect Biochem Mol Biol, (1995), 25:857-66., Elsevier, Netherlands.

Verras M et al., Cloning and characterization of CcEcR. An ecdysone receptor homolog from the mediterranean fruit fly *Ceratitis capitata*, Eur J Biochem, (1999), 265:798-808, Blackwell, United Kingdom.

Wilson JM et al., Hepatocyte-directed gene transfer in vivo leads to transient improvement of hypercholesterolemia in low density lipoprotein receptor-deficient rabbits, J Biol Chem, (1992), 267:963-7, American Society for Biochemistry and Molecular Biology, United States.

Yao TP et al., *Drosophila* ultraspiracle modulates ecdysone receptor function via heterodimer formation, Cell, (1992), 71:63-72, Cell Press, United States.

Yao TP et al., Functional ecdysone receptor is the product of EcR and Ultraspiracle genes, Nature, (1993), 366:476-9, Nature Publishing, United Kingdom.

Christopherson KS et al., Ecdysteroid-dependent regulation of genes in mammalian cells by a *Drosophila* ecdysone receptor and chimeric transactivators, Proc Natl Acad Sci U S A, (1992), 89:6314-8, National Academy of Sciences, United States.

Kakizawa T et al., Ligand-dependent heterodimerization of thyroid hormone receptor and retinoid X receptor, J Biol Chem, (1997), 272:23799-804, American Society for Biochemistry and Molecular Biology, United States.

Koelle MR et al., The *Drosophila* EcR gene encodes an ecdysone receptor, a new member of the steroid receptor superfamily, Cell, (1991), 67:59-77, Cell Press, United States.

Leid M et al., Purification, cloning, and RXR identity of the HeLa cell factor with which RAR or TR heterodimerizes to bind target sequences efficiently, Cell, (1992), 68:377-95; Cell Press, United States.

Leonhardt SA et al., Agonist and antagonists induce homodimerization and mixed ligand heterodimerization of human progesterone receptors in vivo by a mammalian two-hybrid assay, Mol Endocrinol, (1998), 12:1914-30, Endocrine Society, United States.

Metzger D et al., The human oestrogen receptor functions in yeast, Nature, (1988), 334:31-6, Nature Publishing, United Kingdom.

No D et al., Ecdysone-inducible gene expression in mammalian cells and transgenic mice, Proc Natl Acad Sci U S A, (1996), 93:3346-51; National Academy of Sciences, United States.

Perera SC et al., Studies on two ecdysone receptor isoforms of the spruce budworm, *Choristoneura fumiferana*, Mol Cell Endocrinol, (1999), 152:73-84, North Holland Publishing, Netherlands.

Andrianov VG et al., 4-Aminofurazan-3-hydroximic halides, Chemistry of Heterocyclic Compounds, (1992), 28:581-585., Springer-Link, United States.

Andrianov VG et al., 4-Amino-2-1,2,4-oxadiazolines, Chemistry of Heterocyclic Compounds, (1991), 27:216-218. Springer-Link, United States.

Belshaw PJ et al., Controlling protein association and subcellular localization with a synthetic ligand that induces heterodimerization of proteins, Proc Natl Acad Sci U S A, (1996), 93:4604-7., National Academy of Sciences, United States.

Belshaw PJ et al., Rational Design of Orthogonal Receptor-Ligand Combinations, Angewandte Chemie International Edition in English, (1995), 34:2129-2132, Wiley-VCH, Germany.

Brennan JD, Preparation and Entrapment of Fluorescently Labeled Proteins for the Development of Reagentless Optical Biosensor, Journal of Fluorescence, (1999), 9:295-312. Springer, Netherlands.

Cao S et al., N'-tert-Butyl-N'-aroyl-N-(alkoxycarbonylmethyl)-N-aroylhydrazines, a novel nonsteroidal ecdysone agonist: syntheses, insecticidal activity, conformational, and crystal structure analysis Canadian Journal of Chemistry, (2001), 79:272-278, American Chemical Society, United States.

Cao S et al., N'-tert-butyl-N'-aroyl-N-(alkoxycarbonylmethyl)-N-aroylhydrazines, a novel nonsteroidal ecdysone agonist: syntheses, insecticidal activity, conformational, and crystal structure analysis, Canadian Journal of Chemistry, (2001), 79:272-278, NRC Research Press, Canada.

Carlson GR et al., The chemical and biological properties of methoxyfenozide, a new insecticidal ecdysteroid agonist, Pest Management Science, (2001), 57:115-119., Wiley, United Kingdom.

Doyle DF et al., Engineering orthogonal ligand-receptor pairs from "near drugs", J Am Chem Soc, (2001), 123:11367-71, American Chemical Society, United States.

Fields S et al., A novel genetic system to detect protein-protein interactions, Nature, (1989), 340:245-6, Nature Publishing Co., United Kingdom.

Filmus J et al., Synergistic induction of promoters containing metal- and glucocorticoid-responsive elements, Nucleic Acids Res, (1992), 20:2755-60, Oxford University Press, United Kingdom.

Glass CK et al., Nuclear receptor coactivators, Curr Opin Cell Biol, (1997), 9:222-32, Elsevier, United Kingdom.

Holt JR et al., Functional expression of exogenous proteins in mammalian sensory hair cells infected with adenoviral vectors, J Neurophysiol, (1999), 81:1881-8, American Physiological Society, United States.

Notice of Allowance mailed Dec. 27, 2010 in U.S. Appl. No. 11/118,855, inventors Palli et al., filed Apr. 29, 2005.

Notice of Allowance mailed Apr. 27, 2011 in U.S. Appl. No. 11/841,631, inventors Palli et al., filed Aug. 20, 2007.

Office Action mailed Sep. 14, 2010, in U.S. Appl. No. 11/837,834, filed Aug. 13, 2007, inventors Palli et al.

Office Action mailed Feb. 15, 2011, in U.S. Appl. No. 09/965,697, filed Sep. 27, 2001, inventors Dhadialla et al.

Marshall, E., "Gene Therapy on Trial," *Science* 288(5468):951-957, American Association for the Advancement of Science, United States (2000).

Wang, A., et al., "Rapid analysis of gene expression (RAGE) facilitates universal expression profiling," *Nuc. Acids Res.* 27(23:4609-4619, Oxford University Press, England (1999).

Kaufman, R.M., et al., "Transgenic analysis of a 100-kb human beta-globin cluster-containing DNA fragment propagated as a bacterial artificial chromosome," *Blood* 94(9):3178-3184, American Society of Hematology, United States (1999).

Wigley, P., et al., "Site-specific transgene insertion: An approach," *Reprod. Fert. Dev.* 6(5):585-588, Commonwealth Scientific and Industrial Research Organisation, Australia (1994).

Phillips, A.J., "The challenge of gene therapy and DNA delivery," *J. Pharm. Pharmacol.* 53(9):1169-1174, Pharmaceutical Society of Great Britain, England (2001).

Office action mailed Mar. 30, 2011 in U.S. Appl. No. 12/818,034, inventors Palli et al., filed Jun. 17, 2010.

Office action mailed Oct. 18, 2011 in U.S. Appl. No. 12/818,034, inventors Palli et al., filed Jun. 17, 2010.

Office action mailed Jul. 27, 2012 in U.S. Appl. No. 12/859,940, inventors Palli et al., filed Aug. 20, 2010.

Office action mailed Dec. 28, 2012 in U.S. Appl. No. 12/859,940, inventors Palli et al., filed Aug. 20, 2010.

U.S. Appl. No. 13/613,597, inventors Dhadialla et al., filed Sep. 13, 2012.

U.S. Appl. No. 13/615,348, inventors Palli et al., filed Sep. 13, 2012.

U.S. Appl. No. 13/618,693, inventors Palli et al., filed Sep. 13, 2012.

U.S. Appl. No. 13/618,742, inventors Kapitskaya et al., filed Sep. 14, 2012.

U.S. Appl. No. 13/431,636, inventors Dhadialla et al., filed Mar. 27, 2012.

Examiner's SCORE Search Results for U.S. Appl. No. 11/118,855, inventors Palli et al., 27 pages (conducted on Aug. 14, 2007).

Examiner's SCORE Search Results for U.S. Appl. No. 11/118,855, inventors Palli et al., 17 pages (conducted on Aug. 14, 2007).

Helmreich E.J.M., "The Biochemistry of Cell Signalling," p. 192, Oxford University Press (2001).

(56) References Cited

OTHER PUBLICATIONS

Hofmann, A. et al., "Rapid retroviral delivery of tetracycline-inducible genes in a single autoregulatory cassette," *Proc. Natl. Acad. Sci. USA* 93: 5185-5190, National Academy of Sciences (1996).
Hoppe, U.C., et al., "Adenovirus-Mediated Inducible gene Expression in Vivo by a Hybrid Ecdysone Receptor," *Molecular Therapy* 1:159-164, The American Society of Gene Therapy (1999).
Martinez, A., et al., "creation of ecdysone receptor chimeras in plants for controlled regulation of gene expression," *Mol Gen Genet* 261:546-552, Springer-Verlag (1999).
Perera, S.C. et al., "An Analysis of Ecdysone Receptor Domains Required for Heterodimerization With Ultraspiracle," *Archives of Insect Biochemistry and Physiology* 41: 61-70, Wiley-Liss, Inc. (1999).
Shimizu, B-i. et al., "Molting hormonal and larvicidal activities of aliphatic acyl analogs of dibenzoylhydrazine insecticides," *Steroids* 62:638-642, Elsevier Science Inc. (1997).
Talbot, W.S., et al., "*Drosophila* Tissues with Different Metamorphic Responses to Ecdysone Express Different Ecdysone Receptor Isoforms," *Cell* 73:1323-1337, Cell Press (1993).
UniProtKB/Swiss-Protein Database, Accession No. P49880, "Ecdysone receptor," 2 pages (1996).
UniProtKB/Swiss-Protein Database, Accession No. P49883, "Ecdysone receptor," 2 pages (1996).
Office Action mailed Sep. 19, 2007 in U.S. Appl. No. 10/468,193, inventors Palli, et al., filed Dec. 17, 2003.
Office action mailed Aug. 22, 2006 in U.S. Appl. No. 10/239,134, inventors Palli et al., filed Sep. 19, 2002.
Office Action mailed Nov. 24, 2004 in U.S. Appl. No. 09/965,703, inventors Palli, et al., filed Sep. 26, 2001.
Office Action mailed Jun. 13, 2005 in U.S. Appl. No. 09/965,703, inventors Palli, et al., filed Sep. 26, 2001.
Office Action mailed May 14, 2004 in U.S. Appl. No. 09/965,703, inventors Palli, et al., filed Sep. 26, 2001.
Office Action mailed Jul. 12, 2005 in U.S. Appl. No. 09/965,697, inventors Dhadialla, et aL, filed Sep. 27, 2001.
Office Action mailed Apr. 18, 2006 in U.S. Appl. No. 09/965,697, inventors Dhadialla, et al., filed Sep. 27, 2001.
Office Action mailed Nov. 13, 2006 in U.S. Appl. No. 09/965,697, inventors Dhadialla, et al., filed Sep. 27, 2001.
Office Action mailed Aug. 9, 2007 in U.S. Appl. No. 09/965,697, inventors Dhadialla, et al., filed Sep. 27, 2001.
Office Action mailed May 28, 2008 in U.S. Appl. No. 09/965,697, inventors Dhadialla, et al., filed Sep. 27, 2001.
Office Action mailed Oct. 26, 2006 in U.S. Appl. No. 10/468,199, inventors Kapitskaya, et al., filed Dec. 17, 2003.
Office Action mailed Jun. 11, 2007 in U.S. Appl. No. 10/468,199, inventors Kapitskaya, et al., filed Dec. 17, 2003.
Office Action mailed Mar. 13, 2008 in U.S. Appl. No. 10/468,199, inventors Kapitskaya, et al., filed Dec. 17, 2003.
Office Action mailed Sep. 7, 2007 in U.S. Appl. No. 11/118,855, inventors Palli, et al., filed Apr. 29, 2005.
Office Action delivered electronically Aug. 21, 2008 in U.S. Appl. No. 11/677,968, inventors Palli, et al., filed Feb. 22, 2007.
U.S. Appl. No. 10/468,200, inventors Palli, et al., filed Aug. 15, 2003.
U.S. Appl. No. 10/468,192, inventors Palli, et al., filed Aug. 15, 2003.
Wipf et al., "Combinatorial Synthesis and Biological Evaluation of Library of Small-Molecule Ser/Thr-Protein Phosphatase Inhibitors," *Bioorganic & Medicinal Chemistry* 5: 165-177, Elsevier Science, Ltd., Great Britain (1997).
Blumberg, B., et al., "Multiple retinoid-responsive receptors in a single cell: Families of retinoid "X" receptors and retinoic acid receptors in the *Xenopous* egg," *Proc. Natl. Acad. Sci. USA* 89:2321-2325, National Academy of Sciences, United States (1992).
Clayton, G.M., et al., "The structure of the ultraspiracle ligand-binding domain reveals a nuclear receptor locked in an inactive conformation," *Proc. Natl. Acad. Sci.* 98:1549-1554, National Academy of Sciences, United States (2001).

Laudet, V., et al., "A Unified Nomenclature System for the Nuclear Receptor Superfamily," *Cell* 97:161-163, Cell Press, United States (1999).
Mangelsdorf, D.J., et al., "Nuclear receptor that identifies a novel retinoic acid response pathway," *Nature* 345:224-229, Nature Publishing Group, England (1990).
Marklew, S., et al., "Isolation of a novel RXR from *Xenopus* that most closely resembles mammalian RXRβ and is expressed throughout early development," *Biochim Biophys Acta* 1218:267-272, Elsevier Science B.V., Netherlands (1994).
Palmer, M.J., et al., "Characterization of EcR and RXR Homologous in the Ixodid Tick, *Amblyomma amerianum* (L.)," *Am. Zool.* 39:747-757, American Society of Zoologists, United States (1999).
EMBL Nucleotide Sequence Database, Accession No. AJ251542, 7 pages (Entry date 2000).
UniProtKB/Swiss-Protein Database, Accession No. O02035, "Ecdysone receptor," 4 pages (1996).
UniProtKB/Swiss-Protein Database, Accession No. O76246, "Ecdysteroid receptor," 4 pages (1996).
Office action mailed Jun. 30, 2009 in U.S. Appl. No. 11/118,855, inventors Palli et al., filed Apr. 29, 2005.
Office Action mailed Feb. 25, 2009 in U.S. Appl. No. 11/841,325, inventors Dhadialla et al., filed Aug. 20, 2007.
Office Action mailed Feb. 24, 2009 in U.S. Appl. No. 11/841,495, inventors Palli et al., filed Aug. 20, 2007.
Office Action mailed Apr. 2, 2009 in U.S. Appl. No. 11/841,529, inventors Palli et al., filed Aug. 20, 2007.
Office Action mailed Jun. 29, 2009 in U.S. Appl. No. 11/841,648, inventors Kapitskaya et al., filed Aug. 24, 2007.
Office Action mailed Jun. 23, 2009 in U.S. Appl. No. 09/965,697, inventors Dhadialla et al., filed Sep. 27, 2001.
Office Action mailed Dec. 9, 2008 in U.S. Appl. No. 09/965,697, inventors Dhadialla et al., filed Sep. 27, 2001.
Office Action mailed May 22, 2009, in U.S. Appl. No. 11/837,834, inventors Palli et al., filed Aug. 13, 2007.
Office Action mailed Feb. 20, 2009 in U.S. Appl. No. 11/677,968, inventors Palli et al., filed Feb. 22, 2007.
Bowie, J., et al., "Deciphering the message in protein sequences: tolerance to amino acid substitutions," *Science* 247:1306-1310, American Assoc. for the Advancement of Science, United States (1990).
Wells, J., "Additivity of mutational effects in proteins," *Biochemistry* 29:8509-8517, American Chemical Society, United States.
Ngo, J., et al., "Computational complexity, protein structure prediction, and the Levinthal paradox," in *The Protein Folding Problem and Tertiary Structure Prediction*, Merz, K. and S. LeGrand, eds, pp. 433-506, Birkhaüser, Boston (1994).
Office Action mailed Feb. 24, 2009, in U.S. Appl. No. 11/841,945, Palli, S., et al., filed Aug. 20, 2007.
Notice of Allowance mailed Feb. 4, 2010 in U.S. Appl. No. 11/118,855, inventors Palli et al., filed Apr. 29, 2005.
Office Action mailed Sep. 28, 2010 in U.S. Appl. No. 11/841,631, inventors Palli et al., filed Aug. 20, 2007.
Office Action mailed May 12, 2010 in U.S. Appl. No. 11/841,464, inventors Palli et al., filed Aug. 20, 2007.
Notice of Allowance mailed May 24, 2010 in U.S. Appl. No. 11/677,968, inventors Palli et al., filed Feb. 22, 2007.
Office Action mailed Sep. 14, 2010 in U.S. Appl. No. 11/841,644, inventors Palli et al., filed Aug. 20, 2007.
Office action mailed Mar. 22, 2010 in U.S. Appl. No. 11/841,648, inventors Kapitskaya et al., filed Aug. 24, 2007.
Office action mailed Dec. 7, 2010 in U.S. Appl. No. 11/841,648, inventors Kapitskaya et al., filed Aug. 24 ,2007.
Notice of Allowance mailed Mar. 19, 2010 in U.S. Appl. No. 11/841,495, inventors Palli et al., filed Aug. 20, 2007.
Office action mailed Apr. 20, 2010 in U.S. Appl. No. 11/841,597, inventors Kapitskaya et al., filed Aug. 20, 2007.
Office action mailed Nov. 10, 2010 in U.S. Appl. No. 11/841,597, inventors Kapitskaya et al., filed Aug. 20, 2007.
Office Action mailed May 25, 2010 in U.S. Appl. No. 09/965,697, inventors Dhadialla, et al., filed Sep. 27, 2001.
Office Action mailed Dec. 30, 2010 in U.S. Appl. No. 12/707,599, inventors Dhadialla, et al., filed Feb. 17, 2010.

(56) References Cited

OTHER PUBLICATIONS

Office Action mailed Apr. 1, 2010 in U.S. Appl. No. 11/841,529, inventors Palli et al., filed Aug. 20, 2007.
Kumar, M.B., "A single point mutation in ecdysone receptor leads to increased ligand specificity: Implications for gene switch applications," *Proc. Natl. Acad. Sci.* 99: 14710-14715, National Academy of Sciences, United States (2002).
Palli, S.R. et al., "Improved ecdysone receptor-based inducible gene regulation system," *Eur. J. Biochem.* 270: 1308-1315, Wiley Interscience (2003).
Tran, H.T. et al., "Reconstruction of Ligand-Dependent Transactivation of *Choristoneura fumiferana* Ecdysone Receptor in Yeast," *Molecular Endocrinology* 15: 1140-1153, The Endocrine Society (2001).
U.S. Appl. No. 12/859,940, inventors Palli et al., filed Aug. 20, 2010.
Office Action mailed Oct. 21, 2009 in U.S. Appl. No. 11/841,597, inventors Kapitskaya, et al., filed Aug. 20, 2007.
Office Action mailed Feb. 22, 2010, in U.S. Appl. No. 11/837,834, inventors Palli et al., filed Aug. 13, 2007.
Office Action mailed Feb. 18, 2010, in U.S. Appl. No. 10/468,193, inventors Palli et al., filed Dec. 17, 2003.
Office Action mailed Nov. 1, 2013 in U.S. Appl. No. 12/859,940, inventors Palli et al., filed Aug. 20, 2010.
Office Action mailed Nov. 3, 2011 in U.S. Appl. No. 11/841,597, inventors Kapitskaya et al., filed Aug. 20, 2007.
Notice of Allowance mailed Oct. 21, 2013 in U.S. Appl. No. 11/841,529, inventors Patti et al.
Notice of Allowance mailed Jul. 30, 2013 in U.S. Appl. No. 11/841,648, inventors Kapitskaya et al.
Campbell, K.H.S., et al., "Sheep cloned by nuclear transfer from a cultured cell line," *Nature* 380:64-66, Nature Publishing Group, England (1996).
Carver, A.S., et al., "Transgenic Livestock as Bioreactors: Stable Expression of Human Alpha-1-Antitrypsin by a Flock of Sheep," *Bio/Technology* 11:1263-1270, Nature Publishing Company, United States (1993).
Chiou, T.-J. and Bush, D.R., "Molecular Cloning, Immunochemical Localization to the Vacuole, and Expression in Transgenic Yeast and Tobacco of a Putative Sugar Transporter from Sugar Beet," *Plant Physiol.* 110: 511-520, American Society of Plant Physiologists, United States (1996).

Du, S.J., et al., "Growth Enhancement in Transgenic Atlantic Salmon by the Use of an 'All Fish' Chimeric Growth Hormone Gene Construct," *Bio/Technology* 10:176-181, Nature Publishing Company, United States (1992).
McCreath, K.J., et al., "Production of gene-targeted sheep by nuclear transfer from cultured somatic cells," *Nature* 405:1066-1069, *Nature* 408:120, and Nature Ref. N0614E KIND (ERR), 6 Pages, Macmillan Magazines Ltd, England (2000).
Pursel, V.G., et al., "Transfer of an Ovine Metallothionein-Ovine Growth Hormone Fusion Gene into Swine," *J. Anim. Sci.* 75:2208-2214, American Society of Animal Science, United States (1997).
Schnieke, A.E., et al., "Human Factor IX Transgenic Sheep Produced by Transfer of Nuclei from Transfected Fetal Fibroblasts," *Science* 278:2130-2133, American Association for the Advancement of Science, United States (1997).
Wall, R.J., et al., "Transgenic Dairy Cattle: Genetic Engineering on a Large Scale," *J. Dairy Sci.* 80:2213-2224, American Dairy Science Association, United States (1997)
Wilmut, I., et al., "Viable offspring derived from fetal and adult mammalian cells," *Nature* 385:810-813 and *Nature* 386:200, 5 Pages, Nature Publishing Group, England (1997)
Wolf, E., et al., "Transgenic technology in farm animals—progress and perspectives," *Experimental Physiology* 85(6):615-625, The Physiological Society, England (2000).
Zuo, J., et al., An estrogen receptor-based transactivator XVE mediates highly inducible gene expression in transgenic plants, *The Plant Journal* 24(2):265-273, Blackwell Science Ltd, England (2000).
Gama Sosa, M.A., et al., "Animal transgenesis: an overview," *Brain Structure Function* 214: 91-109, Springer (2010).
Sereda, M. et al., "A Transgenic Rat Model of Charcot-Marie-Tooth Disease," *Neuron* 16: 1049-1060 (1996).
Machida, S. et al., "P23H Rhodopsin Transgenic Rat: Correlation of Retinal Function with Histopathology," *Invest. Opthalmol. Vis. Sci.* 41: 3200-3209 (2000).
Saez, E. et al., "Identification of ligands and coligands for the ecdysone-regulated gene switch," *PNAS* 97: 14512-14517 (2000).
Wang, X.-J. et al., "Development of gene-switch transgenic mice that inducibly express transforming growth factor $\beta 1$ in the epidermis," *Proc. Natl. Acad. Sci. USA* 96: 84843-8488 (1999).
Fugger, L. et al., "Expression of HLA-DR4 and human CD4 transgenes in mice determines the variable region $\beta$-chain T-cell repertoire and mediates an HLA-DR-restricted immune response," *Proc. Natl. Acad. Sci. USA* 91: 6151-6155 (1994).
Horuzsko, A. et al., "HLA-G functions as a restriction element and a transplantation antigen in mice," *Intl. Immunol.* 9: 645-653 (1997).

\* cited by examiner

ECDYSONE RECEPTOR-BASED INDUCIBLE GENE EXPRESSION SYSTEM

This application is a continuation of U.S. application Ser. No. 12/818,034, filed Jun. 17, 2010 (now U.S. Pat. No. 8,202, 718), which is a continuation of U.S. application Ser. No. 11/841,495, filed Aug. 20, 2007 (now U.S. Pat. No. 7,776, 587), which is a continuation of U.S. application Ser. No. 11/677,968, filed Feb. 22, 2007 (now U.S. Pat. No. 7,807, 417), which is a continuation of U.S. application Ser. No. 10/239,134, filed Sep. 19, 2002 (abandoned), which is the U.S. National Stage of International Application No. PCT/US01/09050, filed Mar. 21, 2001, which claims priority benefit of U.S. Application No. 60/191,355, filed Mar. 22, 2000 and of U.S. Application No. 60/269,799, filed Feb. 20, 2001.

FIELD OF THE INVENTION

This invention relates to the field of biotechnology or genetic engineering. Specifically, this invention relates to the field of gene expression. More specifically, this invention relates to a novel ecdysone receptor-based inducible gene expression system and methods of modulating the expression of a gene within a host cell using this inducible gene expression system.

BACKGROUND OF THE INVENTION

In the field of genetic engineering, precise control of gene expression is a valuable tool for studying, manipulating, and controlling development and other physiological processes. Gene expression is a complex biological process involving a number of specific protein-protein interactions. In order for gene expression to be triggered, such that it produces the RNA necessary as the first step in protein synthesis, a transcriptional activator must be brought into proximity of a promoter that controls gene transcription. Typically, the transcriptional activator itself is associated with a protein that has at least one DNA binding domain that binds to DNA binding sites present in the promoter regions of genes. Thus, for gene expression to occur, a protein comprising a DNA binding domain and a transactivation domain located at an appropriate distance from the DNA binding domain must be brought into the correct position in the promoter region of the gene.

The traditional transgenic approach utilizes a cell-type specific promoter to drive the expression of a designed transgene. A DNA construct containing the transgene is first incorporated into a host genome. When triggered by a transcriptional activator, expression of the transgene occurs in a given cell type.

Another means to regulate expression of foreign genes in cells is through inducible promoters. Examples of the use of such inducible promoters include the PR1-a promoter, prokaryotic repressor-operator systems, immunosuppressive-immunophilin systems, and higher eukaryotic transcription activation systems such as steroid hormone receptor systems and are described below.

The PR1-a promoter from tobacco is induced during the systemic acquired resistance response following pathogen attack. The use of PR1-a may be limited because it often responds to endogenous materials and external factors such as pathogens, UV-B radiation, and pollutants. Gene regulation systems based on promoters induced by heat shock, interferon and heavy metals have been described (Wurn et al., 1986, Proc. Natl. Acad. Sci. USA 83:5414-5418; Arnheiter et al., 1990 Cell 62:51-61; Filmus et al., 1992 Nucleic Acids Research 20:27550-27560). However, these systems have limitations due to their effect on expression of non-target genes. These systems are also leaky.

Prokaryotic repressor-operator systems utilize bacterial repressor proteins and the unique operator DNA sequences to which they bind. Both the tetracycline ("Tet") and lactose ("Lac") repressor-operator systems from the bacterium *Escherichia coli* have been used in plants and animals to control gene expression. In the Tet system, tetracycline binds to the TetR repressor protein, resulting in a conformational change which releases the repressor protein from the operator which as a result allows transcription to occur. In the Lac system, a lac operon is activated in response to the presence of lactose, or synthetic analogs such as isopropyl-b-D-thiogalactoside. Unfortunately, the use of such systems is restricted by unstable chemistry of the ligands, i.e. tetracycline and lactose, their toxicity, their natural presence, or the relatively high levels required for induction or repression. For similar reasons, utility of such systems in animals is limited.

Immunosuppressive molecules such as FK506, rapamycin and cyclosporine A can bind to immunophilins FKBP12, cyclophilin, etc. Using this information, a general strategy has been devised to bring together any two proteins simply by placing FK506 on each of the two proteins or by placing FK506 on one and cyclosporine A on another one. A synthetic homodimer of FK506 (FK1012) or a compound resulted from fusion of FK506-cyclosporine (FKCsA) can then be used to induce dimerization of these molecules (Spencer et al., 1993, Science 262:1019-24; Belshaw et al., 1996 Proc Natl Acad Sci USA 93:4604-7). Gal4 DNA binding domain fused to FKBP12 and VP16 activator domain fused to cyclophilin, and FKCsA compound were used to show heterodimerization and activation of a reporter gene under the control of a promoter containing Gal4 binding sites. Unfortunately, this system includes immunosuppressants that can have unwanted side effects and therefore, limits its use for various mammalian gene switch applications.

Higher eukaryotic transcription activation systems such as steroid hormone receptor systems have also been employed. Steroid hormone receptors are members of the nuclear receptor superfamily and are found in vertebrate and invertebrate cells. Unfortunately, use of steroidal compounds that activate the receptors for the regulation of gene expression, particularly in plants and mammals, is limited due to their involvement in many other natural biological pathways in such organisms. In order to overcome such difficulties, an alternative system has been developed using insect ecdysone receptors (EcR).

Growth, molting, and development in insects are regulated by the ecdysone steroid hormone (molting hormone) and the juvenile hormones (Dhadialla, et al., 1998. Annu. Rev. Entomol. 43: 545-569). The molecular target for ecdysone in insects consists of at least ecdysone receptor (EcR) and ultraspiracle protein (USP). EcR is a member of the nuclear steroid receptor super family that is characterized by signature DNA and ligand binding domains, and an activation domain (Koelle et al. 1991, Cell, 67:59-77). EcR receptors are responsive to a number of steroidal compounds such as ponasterone A and muristerone A. Recently, non-steroidal compounds with ecdysteroid agonist activity have been described, including the commercially available insecticides tebufenozide and methoxyfenozide that are marketed world wide by Rohm and Haas Company (see International Patent Application No. PCT/EP96/00686 and U.S. Pat. No. 5,530, 028). Both analogs have exceptional safety profiles to other organisms.

International Patent Application No. PCT/US97/05330 (WO 97/38117) discloses methods for modulating the expression of an exogenous gene in which a DNA construct comprising the exogenous gene and an ecdysone response element is activated by a second DNA construct comprising an ecdysone receptor that, in the presence of a ligand therefore, and optionally in the presence of a receptor capable of acting as a silent partner, binds to the ecdysone response element to induce gene expression. The ecdysone receptor of choice was isolated from *Drosophila melanogaster*. Typically, such systems require the presence of the silent partner, preferably retinoid X receptor (RXR), in order to provide optimum activation. In mammalian cells, insect ecdysone receptor (EcR) heterodimerizes with retinoid X receptor (RXR) and regulates expression of target genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. Unfortunately, this system is not effective for inducing reporter gene expression in animal cells (for comparison, see Example 1.2, below).

In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

Drawbacks of the above described EcR-based gene regulation systems include a considerable background activity in the absence of ligands and that these systems are not applicable for use in both plants and animals (see U.S. Pat. No. 5,880,333). For most applications that rely on modulating gene expression, these EcR-based systems are undesirable. Therefore, a need exists in the art for improved systems to precisely modulate the expression of exogenous genes in both plants and animals. Such improved systems would be useful for applications such as gene therapy, large scale production of proteins and antibodies, cell-based high throughput screening assays, functional genomics and regulation of traits in transgenic animals. Improved systems that are simple, compact, and dependent on ligands that are relatively inexpensive, readily available, and of low toxicity to the host would prove useful for regulating biological systems.

Various publications are cited herein, the disclosures of which are incorporated by reference in their entireties. However, the citation of any reference herein should not be construed as an admission that such reference is available as "Prior Art" to the instant application.

SUMMARY OF THE INVENTION

The present invention relates to a novel ecdysone receptor-based inducible gene expression system, novel receptor polynucleotides and polypeptides for use in the novel inducible gene expression system, and methods of modulating the expression of a gene within a host cell using this inducible gene expression system. In particular, Applicants' invention relates to an improved gene expression modulation system comprising a polynucleotide encoding a receptor polypeptide comprising a truncation mutation.

Specifically, the present invention relates to a gene expression modulation system comprising: a) a first gene expression cassette that is capable of being expressed in a host cell comprising a polynucleotide that encodes a first polypeptide comprising: i) a DNA-binding domain that recognizes a response element associated with a gene whose expression is to be modulated; and a ligand binding domain comprising a ligand binding domain from a nuclear receptor; and b) a second gene expression cassette that is capable of being expressed in the host cell comprising a polynucleotide sequence that encodes a second polypeptide comprising: i) a transactivation domain; and a ligand binding domain comprising a ligand binding domain from a nuclear receptor other than an ultraspiracle receptor; wherein the DNA binding domain and the transactivation domain are from a polypeptide other than an ecdysone receptor, a retinoid X receptor, or an ultraspiracle receptor; wherein the ligand binding domains from the first polypeptide and the second polypeptide are different and dimerize.

In a specific embodiment, the ligand binding domain of the first polypeptide comprises an ecdysone receptor (EcR) ligand binding domain In another specific embodiment, the ligand binding domain of the second polypeptide comprises a retinoid X receptor (RXR) ligand binding domain.

In a preferred embodiment, the ligand binding domain of the first polypeptide comprises an ecdysone receptor ligand binding domain and the ligand binding domain of the second polypeptide comprises a retinoid X receptor ligand binding domain The present invention also relates to a gene expression modulation system according, to the invention further comprising c) a third gene expression cassette comprising: i) a response element to which the DNA-binding domain of the first polypeptide binds; ii) a promoter that is activated by the transactivation domain of the second polypeptide; and the gene whose expression is to be modulated.

The present invention also relates to an isolated polynucleotide encoding a truncated EcR or a truncated RXR polypeptide, wherein the truncation mutation affects ligand binding activity or ligand sensitivity.

In particular, the present invention relates to an isolated polynucleotide encoding a truncated EcR or a truncated RXR polypeptide comprising a truncation mutation that reduces ligand binding activity or ligand sensitivity of said EcR or RXR polypeptide. In a specific embodiment, the present invention relates to an isolated polynucleotide encoding a truncated EcR or a truncated RXR polypeptide comprising a truncation mutation that reduces steroid binding activity or steroid sensitivity of said EcR or RXR polypeptide. In another specific embodiment, the present invention relates to an isolated polynucleotide encoding a truncated EcR or a truncated RXR polypeptide comprising a truncation mutation that reduces non-steroid binding activity or non-steroid sensitivity of said EcR or RXR polypeptide.

The present invention also relates to an isolated polynucleotide encoding a truncated EcR or a truncated RXR polypeptide comprising a truncation mutation that enhances ligand binding activity or ligand sensitivity of said EcR or RXR polypeptide. In a specific embodiment, the present invention relates to an isolated polynucleotide encoding a truncated EcR or a truncated RXR polypeptide comprising a truncation mutation that enhances steroid binding activity or steroid sensitivity of said EcR or RXR polypeptide. In another specific embodiment, the present invention relates to an isolated polynucleotide encoding a truncated EcR or a truncated RXR polypeptide comprising a truncation mutation that enhances non-steroid binding activity or non-steroid sensitivity of said EcR or RXR polypeptide.

The present invention also relates to an isolated polynucleotide encoding a truncated RXR polypeptide comprising a truncation mutation that increases ligand sensitivity of a heterodimer comprising the truncated retinoid X receptor polypeptide and a dimerization partner. In a specific embodiment, the dimerization partner is an ecdysone receptor polypeptide.

The present invention also relates to an isolated polypeptide encoded by a polynucleotide according to Applicants' invention. In particular, the present invention relates to an isolated truncated EcR or truncated RXR polypeptide comprising a truncation mutation, wherein the EcR or RXR polypeptide is encoded by a polynucleotide according to the invention.

Thus, the present invention also relates to an isolated truncated EcR or truncated RXR polypeptide comprising a truncation mutation that affects ligand binding activity or ligand sensitivity of said EcR or RXR polypeptide.

Applicants' invention also relates to methods of modulating gene expression in a host cell using a gene expression modulation system according to the invention. Specifically, Applicants' invention provides a method of modulating the expression of a gene in a host cell comprising the gene to be modulated comprising the steps of: a) introducing into the host cell a gene expression modulation system according to the invention; and b) introducing into the host cell a ligand that independently combines with the ligand binding domains of the first polypeptide and the second polypeptide of the gene expression modulation system; wherein the gene to be expressed is a component of a chimeric gene comprising: i) a response element comprising a domain to which the DNA binding domain from the first polypeptide binds; ii) a promoter that is activated by the transactivation domain of the second polypeptide; and the gene whose expression is to be modulated, whereby a complex is formed comprising the ligand, the first polypeptide, and the second polypeptide, and whereby the complex modulates expression of the gene in the host cell.

Applicants' invention also provides an isolated host cell comprising an inducible gene expression system according to the invention. The present invention also relates to an isolated host cell comprising a polynucleotide or polypeptide according to the invention. Accordingly, Applicants' invention also relates to a non-human organism comprising a host cell according to the invention.

DETAILED DESCRIPTION OF THE INVENTION

Figure 1:
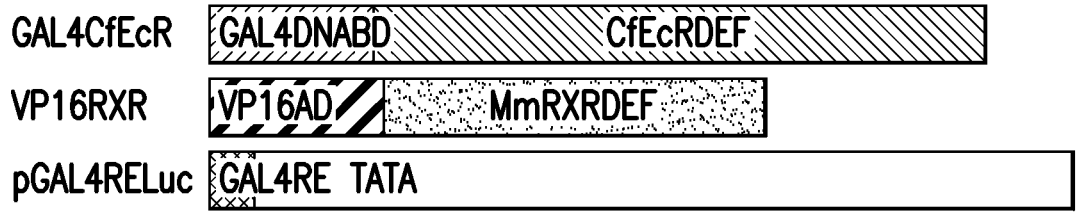
FIG. 1: An ecdysone receptor-based gene expression, system comprising a first gene expression cassette encoding a Gal4DBD-CfEcRDEF chimeric polypeptide and a second gene expression cassette encoding a VP16AD-MmRXRDEF chimeric polypeptide; prepared as described in Example 1 (switch 1.1).
Figure 2:
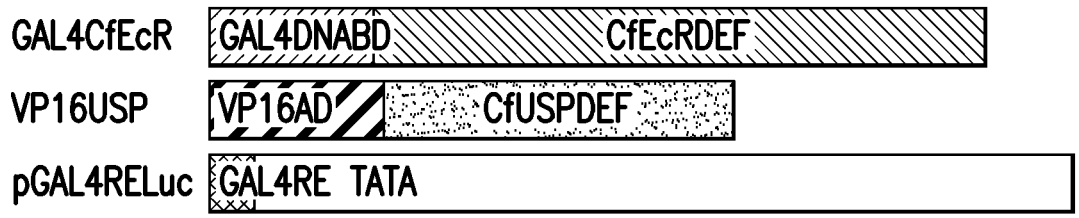
FIG. 2: An ecdysone receptor gene expression system comprising a first gene expression cassette encoding a Gal4DBD-CfEcRDEF chimeric polypeptide and a second gene expression cassette encoding a VP16AD-CfUSPDEF Chimeric polypeptide; prepared as described in Example 1 (switch 1.2).
Figure 3:
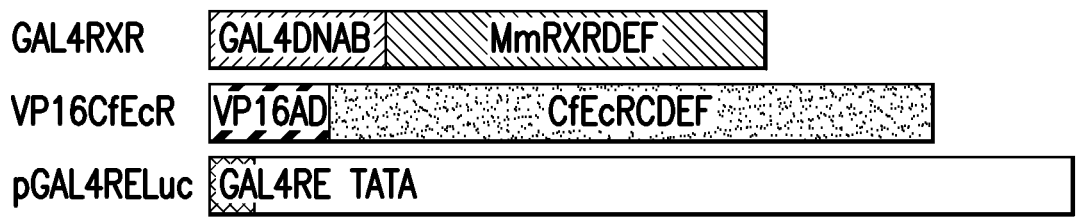
FIG. 3: An ecdysone receptor-based gene expression system comprising a first gene expression cassette encoding a Gal4DBD-MmRXRDEF chimeric polypeptide and a second gene expression cassette encoding a VP16AD-CfEcRCDEF chimeric polypeptide; prepared as described in Example 1 (switch 1.3).
Figure 4:
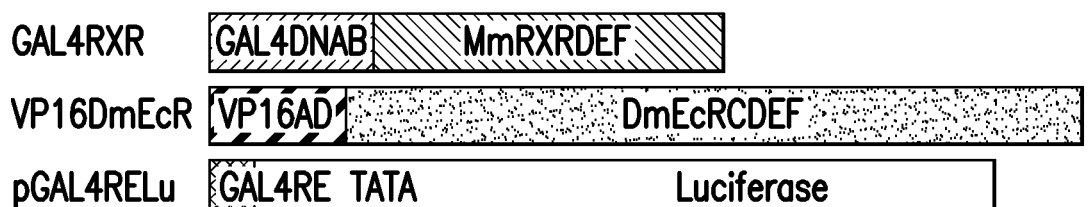
FIG. 4: An ecdysone receptor-based gene expression system comprising a first gene expression cassette encoding a Gal4DBD-MmRXRDEF chimeric polypeptide and a second gene expression cassette encoding a VP16AD-DmEcRCDEF chimeric polypeptide; prepared as described in Example 1 (switch 1.4).
Figure 5:
FIG. 5: An ecdysone receptor-based gene expression system comprising a first gene expression cassette encoding a Gal4DBD-CfUSPDEF chimeric polypeptide and a second gene expression cassette encoding a VP16AD-CfEcRCDEF chimeric polypeptide; prepared as described in Example 1 (switch 1.5).
Figure 5:
Figure 5:
Figure 6:
FIG. 6: An ecdysone receptor-based gene expression system comprising a first gene expression cassette encoding a Gal4DBD-CfEcRDEF-VP16AD chimeric polypeptide; prepared as described in Example 1 (switch 1.6).
Figure 6:
Figure 7:
FIG. 7: An ecdysone receptor-based gene expression system comprising a first gene expression cassette encoding a VP16AD-CfEcRCDEF chimeric polypeptide; prepared as described in Example 1 (switch 1.7).
Figure 7:
Figure 8:
FIG. 8: An ecdysone receptor-based gene expression system comprising a first gene expression cassette encoding a VP16AD-DmEcRCDEF chimeric polypeptide and a second gene expression cassette encoding a MmRXR polypeptide; prepared as described in Example 1 (switch 1.3).
Figure 8:
Figure 8:
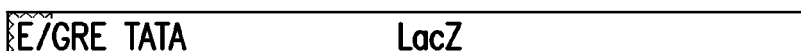
Figure 9:
FIG. 9: An ecdysone receptor-based gene expression system comprising a first gene expression cassette encoding a VP16AD-CfEcRCDEF chimeric polypeptide and a second gene expression cassette encoding a MmRXR polypeptide; prepared as described in Example 1 (switch 1.9).
Figure 9:
Figure 9:
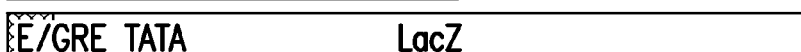
Figure 10:
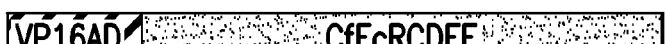
FIG. 10: An ecdysone receptor-based gene expression system comprising a gene expression cassette encoding a Gal4DBD-CfEcRCDEF chimeric polypeptide; prepared as described in Example 1 (switch 1.10).
Figure 10:

Applicants have now developed an improved ecdysone receptor-based inducible gene expression system comprising a truncation mutant of an ecdysone receptor or a retinoid X receptor (RXR) polypeptide that affects ligand binding activity or ligand sensitivity. This mutational effect may increase or reduce ligand binding activity or ligand sensitivity and may be steroid or non-steroid specific. Thus, Applicants' invention provides an improved ecdysone receptor-based inducible gene expression system useful for modulating expression of a gene of interest in a host cell. In a particularly desirable embodiment, Applicants' invention provides an inducible gene expression system that has a reduced level of background gene expression and responds to submicromolar concentrations of non-steroidal ligand. Thus, Applicants' novel inducible gene expression system and its use in methods of modulating gene expression in a host cell overcome the limitations of currently available inducible expression systems and provide the skilled artisan with an effective means to control gene expression.

The present invention provides a novel inducible gene expression system that can be used to modulate gene expression in both prokaryotic and eukaryotic host cells. Applicants' invention is useful for applications such as gene therapy, large scale production of proteins and antibodies, cell-based high throughput screening assays, functional genomics and regulation of traits in transgenic organisms.

DEFINITIONS

In this disclosure, a number of terms and abbreviations are used. The following definitions are provided and should be helpful in understanding the scope and practice of the present invention.

In a specific embodiment, the term "about" or "approximately" means within 20%, preferably within 10%, more preferably within 5%, and even more preferably within 1% of a given value or range.

The term "substantially free" means that a composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The term "isolated" for the purposes of the present invention designates a biological material (nucleic acid or protein) that has been removed from its original environment (the environment in which it is naturally present).

For example, a polynucleotide present in the natural state in a plant or an animal is not isolated. The same polynucleotide separated from the adjacent nucleic acids in which it is naturally present. The term "purified" does not require the material to be present in a form exhibiting absolute purity, exclusive of the presence of other compounds. It is rather a relative definition.

A polynucleotide is in the "purified" state after purification of the starting material or of the natural material by at least one order of magnitude, preferably 2 or 3 and preferably 4 or 5 orders of magnitude.

A "nucleic acid" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes but is not limited to cDNA, genomic DNA, plasmids DNA, synthetic DNA, and semi-synthetic DNA. DNA may be linear, circular, or supercoiled.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester anologs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

The term "fragment" will be understood to mean a nucleotide sequence of reduced length relative to the reference nucleic acid and comprising, over the common portion, a nucleotide sequence identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least 8, 10, 12, 15, 18, 20 to 25, 30, 40, 50, 70, 80, 100, 200, 500, 1000 or 1500 consecutive nucleotides of a nucleic acid according to the invention.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and/or coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A chimeric gene may comprise coding sequences derived from different sources and/or regulatory sequences derived from different sources. "Endogenous gene" refers to a native gene in its natural location in the genome of an organism. A "foreign" gene or "heterologous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Heterologous" DNA refers to DNA not naturally located in the cell, or in a chromosomal site of the cell. Preferably, the heterologous DNA includes a gene foreign to the cell.

The term "genome" includes chromosomal as well as mitochondrial, chloroplast and viral DNA or RNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989 infra). Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization.

Stringency conditions can be adjusted to screen for moderately similar fragments, such as homologous sequences from distantly related organisms, to highly similar fragments, such as genes that duplicate functional enzymes from closely related organisms. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as disclosed or used herein as well as those substantially similar nucleic acid sequences.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

Post-hybridization washes also determine stringency conditions. One set of preferred conditions uses a series of washes starting with 6×SSC, 0.5% SDS at room temperature for 15 minutes (min), then repeated with 2×SSC, 0.5% SDS at 45° C. for 30 minutes, and then repeated twice with 0.2×SSC, 0.5% SDS at 50° C. for 30 minutes. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids comprise complementary sequences, although depending on the stringency of the hybridization, mismatches between bases are possible.

The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook at al., supra, 11.7-11.8).

In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "probe" refers to a single-stranded nucleic acid molecule that can base pair with a complementary single stranded target nucleic acid to form a double-stranded molecule.

As used herein, the term "oligonucleotide" refers to a nucleic acid, generally of at least 18 nucleotides, that is hybridizable to a genomic DNA molecule, a cDNA molecule, a plasmid DNA or an mRNA molecule. Oligonucleotides can be labeled, e.g., with $^{32}$P-nucleotides or nucleotides to which a label, such as biotin, has been covalently conjugated. A labeled oligonucleotide can be used as a probe to detect the presence of a nucleic acid. Oligonucleotides (one or both of which may be labeled) can be used as PCR primers, either for cloning full length or a fragment of a nucleic acid, or to detect the presence of a nucleic acid. An oligonucleotide can also be used to form a triple helix with a DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A "primer" is an oligonucleotide that hybridizes to a target nucleic acid sequence to create a double stranded nucleic acid region that can serve as an initiation point for DNA synthesis under suitable conditions. Such primers may be used in a polymerase chain reaction.

"Polymerase chain reaction" is abbreviated PCR and means an in vitro method for enzymatically amplifying specific nucleic acid sequences. PCR involves a repetitive series of temperature cycles with each cycle comprising three stages: denaturation of the template nucleic acid to separate the strands of the target molecule, annealing a single stranded PCR oligonucleotide primer to the template nucleic acid, and extension of the annealed primer(s) by DNA polymerase. PCR provides a means to detect the presence of the target molecule and, under quantitative or semi-quantitative conditions, to determine the relative amount of that target molecule within the starting pool of nucleic acids.

"Reverse transcription-polymerase chain reaction" is abbreviated RT-PCR and means an in vitro method for enzymatically producing a target cDNA molecule or molecules from an RNA molecule or molecules, followed by enzymatic amplification of a specific nucleic acid sequence or sequences within the target cDNA molecule or molecules as described above. RT-PCR also provides a means to detect the presence of the target molecule and, under quantitative or semi-quantitative conditions, to determine the relative amount of that target molecule within the starting pool of nucleic acids.

A DNA "coding sequence" is a double-stranded DNA sequence that is transcribed and translated into a polypeptide in a cell in vitro or in vivo when placed under the control of appropriate regulatory sequences. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure. The boundaries of the coding sequence are determined by a start codon at the 5' (amino) terminus and a translation stop codon at the 3' (carboxyl) terminus. A coding sequence can include, but is not limited to, prokaryotic sequences, cDNA from mRNA, genomic DNA sequences, and even synthetic DNA sequences. If the coding sequence is intended for expression in a eukaryotic cell, a polyadenylation signal and transcription termination sequence will usually be located 3' to the coding sequence.

"Open reading frame" is abbreviated ORF and means a length of nucleic acid sequence, either DNA, cDNA or RNA, that comprises a translation start signal or initiation codon, such as an ATG or AUG, and a termination codon and can be potentially translated into a polypeptide sequence.

The term "head-to-head" is used herein to describe the orientation of two polynucleotide sequences in relation to each other. Two polynucleotides are positioned in a head-to-head orientation when the 5' end of the coding strand of one polynucleotide is adjacent to the 5' end of the coding strand of the other polynucleotide, whereby the direction of transcription of each polynucleotide proceeds away from the 5' end of the other polynucleotide. The term "head-to-head" may be abbreviated (5')-to-(5') and may also be indicated by the symbols (← →) or (3'←5'5'→3').

The term "tail-to-tail" is used herein to describe the orientation of two polynucleotide sequences in relation to each other. Two polynucleotides are positioned in a tail-to-tail orientation when the 3' end of the coding strand of one polynucleotide is adjacent to the 3' end of the coding strand of the other polynucleotide, whereby the direction of transcription of each polynucleotide proceeds toward the other polynucleotide. The term "tail-to-tail" may be abbreviated (3')-to-(3') and may also be indicated by the symbols (→ ←) or (5'→3'3'←5').

The "head-to-tail" is used herein to describe the orientation of two polynucleotide sequences in relation to each other. Two polynucleotides are positioned in a head-to-tail orientation when the 5' end of the coding strand of one polynucleotide is adjacent to the 3' end of the coding strand of the other polynucleotide, whereby the direction of transcription of each polynucleotide proceeds in the same direction as that of the other polynucleotide. The term "head-to-tail" may be abbreviated (5')-to-(3') and may also be indicated by the symbols (→ →) or (5'→3'5'→3').

The term "downstream" refers to a nucleotide sequence that is located 3' to reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" refer to an enzyme that binds and cuts within a specific nucleotide sequence within double stranded DNA.

"Homologous recombination" refers to the insertion of a foreign DNA sequence into another DNA molecule, e.g., insertion of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

Several methods known in the art may be used to propagate a polynucleotide according to the invention. Once a suitable host system and growth conditions are established, recombinant expression vectors can be propagated and prepared in quantity. As described herein, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A "vector" is any means for the cloning of and/or transfer of a nucleic acid into a host cell. A vector may be a replicon to which another DNA segment may be attached so as to bring about the replication of the attached segment. A "replicon" is any genetic element (e.g., plasmid, phage, cosmid, chromosome, virus) that functions as an autonomous unit of DNA replication in vivo, i.e., capable of replication under its own control. The term "vector" includes both viral and nonviral means for introducing the nucleic acid into a cell in vitro, ex vivo or in vivo. A large number of vectors known in the art may be used to manipulate nucleic acids, incorporate response elements and promoters into genes, etc. Possible vectors include, for example, plasmids or modified viruses including, for example bacteriophages such as lambda derivatives, or plasmids such as PBR322 or pUC plasmid derivatives, or the Bluescript vector. For example, the insertion of the DNA fragments corresponding to response elements and promoters into a suitable vector can be accomplished by ligating the appropriate DNA fragments into a chosen vector that has complementary cohesive termini. Alternatively, the ends of the DNA molecules may be enzymatically modified or any site may be produced by ligating nucleotide sequences (linkers) into the DNA termini. Such vectors may be engineered to contain selectable marker genes that provide for the selection of cells that have incorporated the marker into the cellular genome. Such markers allow identification and/or selection of host cells that incorporate and express the proteins encoded by the marker.

Viral vectors, and particularly retroviral vectors, have been used in a wide variety of gene delivery applications in cells, as well as living animal subjects. Viral vectors that can be used include but are not limited to retrovirus, adeno-associated virus, pox, baculovirus, vaccinia, herpes simplex, Epstein-Barr, adenovirus, geminivirus, and caulimovirus vectors. Non-viral vectors include plasmids, liposomes, electrically charged lipids (cytofectins), DNA-protein complexes, and biopolymers. In addition to a nucleic acid, a vector may also comprise one or more regulatory regions, and/or selectable markers useful in selecting, measuring, and monitoring nucleic acid transfer results (transfer to which tissues, duration of expression, etc.).

The term "plasmid" refers to an extra chromosomal element often carrying a gene that is not part of the central metabolism of the cell, and usually in the form of circular double-stranded DNA molecules. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

A "cloning vector" is a "replicon", which is a unit length of a nucleic acid, preferably DNA, that replicates sequentially and which comprises an origin of replication, such as a plasmid, phage or cosmid, to which another nucleic acid segment may be attached so as to bring about the replication of the attached segment. Cloning vectors may be capable of replication in one cell type and expression in another ("shuttle vector").

Vectors may be introduced into the desired host cells by methods known in the art, e.g., transfection, electroporation, microinjection, transduction, cell fusion, DEAE dextran calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; and Hartmut et al., Canadian Patent Application No. 2,012,311, filed Mar. 15, 1990).

A polynucleotide according to the invention can also be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner et al., 1987. PNAS 84:7413; Mackey, et al., 1988. Proc. Natl. Acad. Sci. U.S.A. 85:8027-8031; and Ulmer et al., 1993. Science 259:1745-1748). The use of cationic lipids may promote encapsulation of negatively charged nucleic acids, nucleic acids, and also promote fusion with negatively charged cell membranes (Feigner and Ringold, 1989. Science 337:387-388). Particularly useful lipid compounds and compositions for transfer of nucleic acids are described in International Patent Publications WO95/18863 and WO96/17823, and in U.S. Pat. No. 5,459,127. The use of lipofection to introduce exogenous genes into the specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a vector in vivo as a naked DNA plasmid (see U.S. Pat. Nos. 5,693,622, 5,589,466 and 5,580,859). Receptor-mediated DNA delivery approaches can also be used (Curiel et al., 1992. Hum. Gene Ther. 3:147-154; and Wu and Wu, 1987. J. Biol. Chem. 262:4429-4432).

The term "transfection" means the uptake of exogenous or heterologous RNA or DNA by a cell. A cell has been "transfected" by exogenous or heterologous RNA or DNA when such RNA or DNA has been introduced inside the cell. A cell has been "transformed" by exogenous or heterologous RNA or DNA when the transfected RNA or DNA effects a phenotypic change. The transforming RNA or DNA can be integrated (covalently linked) into chromosomal DNA making up the genome of the cell.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The term "genetic region" will refer to a region of a nucleic acid molecule or a nucleotide sequence that comprises a gene encoding a polypeptide.

In addition, the recombinant vector comprising a polynucleotide according to the invention may include one or more origins for replication in the cellular hosts in which their amplification or their expression is sought, markers or selectable markers.

The term "selectable marker" means an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like, wherein the effect is used to track the inheritance of a nucleic acid of interest and/or to identify a cell or organism that has inherited the nucleic acid of interest. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentanyl transferase gene, and the like.

The term "reporter gene" means a nucleic acid encoding an identifying factor that is able to be identified based upon the reporter gene's effect wherein the effect is used to track the inheritance of a nucleic acid of interest, to identify a cell or organism that has inherited the nucleic acid of interest, and/or to measure gene expression induction or transcription. Examples of reporter genes known and used in the art include: luciferase (Luc), green fluorescent protein (GFP), chloramphenicol acetyltransferase (CAT), β-galactosidase (LacZ), β-glucuronidase (Gus), and the like. Selectable marker genes may also be considered reporter genes.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". Promoters that cause a gene to be expressed in a specific cell type are commonly referred to as "cell-specific promoters" or "tissue-specific promoters". Promoters that cause a gene to be expressed at a specific stage of development or cell differentiation are commonly referred to as "developmentally-specific promoters" or "cell differentiation-specific promoters". Promoters that are induced and cause a gene to be expressed following exposure or treatment of the cell with an agent, biological molecule, chemical, ligand, light, or the like that induces the promoter are commonly referred to as "inducible promoters" or "regulatable promoters". It is further recognized that since in most cases the exact boundaries of regulatory sequences have not been completely defined, DNA fragments of different lengths may have identical promoter activity.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced (if the coding sequence contains introns) and translated into the protein encoded by the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

The term "response element" means one or more cis-acting DNA elements which confer responsiveness on a promoter mediated through interaction with the DNA-binding domains of the first chimeric gene. This DNA element may be either palindromic (perfect or imperfect) in its sequence or composed of sequence motifs or half sites separated by a variable number of nucleotides. The half sites can be similar or identical and arranged as either direct or inverted repeats or as a single half site or multimers of adjacent half sites in tandem. The response element may comprise a minimal promoter isolated from different organisms depending upon the nature of the cell or organism into which the response element will be incorporated. The DNA binding domain of the first hybrid protein binds, in the presence or absence of a ligand, to the DNA sequence of a response element to initiate or suppress transcription of downstream gene(s) under the regulation of this response element. Examples of DNA sequences for response elements of the natural ecdysone receptor include: RRGG/TTCANTGAC/ACYY (see Cherbas L., et. al., (1991), *Genes Dev.* 5, 120-131); AGGTCAN$_{(n)}$AGGTCA, where N$_{(n)}$ can be one or more spacer nucleotides (see D'Avino P P., et. al., (1995), *Mol. Cell. Endocrinol,* 113, 1-9); and GGGTTGAATGAATTT (see Antoniewski C., et. al., (1994). Mol. Cell Biol. 14, 4465-4474).

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a nucleic acid or polynucleotide. Expression may also refer to translation of mRNA into a protein or polypeptide.

The terms "cassette", "expression cassette" and "gene expression cassette" refer to a segment of DNA that can be inserted into a nucleic acid or polynucleotide at specific restriction sites or by homologous recombination. The segment of DNA comprises a polynucleotide that encodes a polypeptide of interest, and the cassette and restriction sites are designed to ensure insertion of the cassette in the proper reading frame for transcription and translation. "Transformation cassette" refers to a specific vector comprising a polynucleotide that encodes a polypeptide of interest and having elements in addition to the polynucleotide that facilitate transformation of a particular host cell. Cassettes, expression cassettes, gene expression cassettes and transformation cassettes of the invention may also comprise elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

For purposes of this invention, the term "gene switch" refers to the combination of a response element associated with a promoter, and an EcR based system which, in the presence of one or more ligands, modulates the expression of a gene into which the response element and promoter are incorporated.

The terms "modulate" and "modulates" mean to induce, reduce or inhibit nucleic acid or gene expression, resulting in the respective induction, reduction or inhibition of protein or polypeptide production.

The plasmids or vectors according to the invention may further comprise at least one promoter suitable for driving expression of a gene in a host cell. The term "expression vector" means a vector, plasmid or vehicle designed to enable the expression of an inserted nucleic acid sequence following transformation into the host. The cloned gene, i.e., the inserted nucleic acid sequence, is usually placed under the control of control elements such as a promoter, a minimal promoter, an enhancer, or the like. Initiation control regions or promoters, which are useful to drive expression of a nucleic acid in the desired host cell are numerous and familiar to those skilled in the art. Virtually any promoter capable of driving these genes is suitable for the present invention including but not limited to: viral promoters, plant promoters, bacterial promoters, animal promoters, mammalian promoters, synthetic promoters, constitutive promoters, tissue specific promoter, developmental specific promoters, inducible promoters, light regulated promoters; CYC1, HIS3, GAL1, GAL4, GAL10, ADH1, PGK, PHO5, GAPDH, ADC1, TRP1, URA3, LEU2, ENO, TPI, alkaline phosphatase promoters (useful for expression in *Saccharomyces*); AOX1 promoter (useful for expression in *Pichia*); b-lactamase, lac, ara, tet, trp, lP$_L$, lP$_R$, T7, tac, and trc promoters (useful for expression in *Escherichia coli*); and light regulated-, seed specific-, pollen specific-, ovary specific-, pathogenesis or disease related-, cauliflower mosaic virus 35S, CMV 35S minimal, cassava vein mosaic virus (CsVMV), chlorophyll a/b binding protein, ribulose 1,5-bisphosphate carboxylase, shoot-specific, root specific, chitinase, stress inducible, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses, the cytomegalovirus early promoter, the herpes simplex virus (HSV) thymidine kinase (TK) promoter, an elongation factor 1 alpha (EF1) promoter, a phosphoglycerate kinase (PGK) promoter, a ubiquitin (Ubc) promoter, an albumin promoter, the regulatory sequences of the mouse metallothionein-L promoter, and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in liver, alpha 1-antitrypsin gene control region active in the liver, beta-globin gene control region active in myeloid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell α-actin, and the like. In a preferred embodiment of the invention, the promoter is selected from the group consisting of a cauliflower mosaic virus 35S promoter, a cassava vein mosaic virus promoter, and a cauliflower mosaic virus 35S minimal promoter, an elongation factor 1 alpha (EF1) promoter, a phosphoglycerate kinase (PGK) promoter, a ubiquitin (Ubc) promoter, and an albumin promoter. In addition, these expression sequences may be modified by addition of enhancer or regulatory sequences and the like.

Enhancers that may be used in embodiments of the invention include but are not limited to: tobacco mosaic virus enhancer, cauliflower mosaic virus 35S enhancer, tobacco etch virus enhancer, ribulose 1,5-bisphosphate carboxylase enhancer, rice tungro baciliform virus enhancer, and other plant and viral gene enhancers, and the like.

Termination control regions, i.e., terminator or polyadenylation sequences, may also be derived from various genes native to the preferred hosts. Optionally, a termination site may be unnecessary, however, it is most preferred if included. In a preferred embodiment of the invention, the termination control region may be comprise of be derived from a synthetic sequence, synthetic polyadenylation signal, an SV40 late polyadenylation signal, an SV40 polyadenylation signal, a bovine growth hormone (BGH) polyadenylation signal, nopaline synthase (nos), cauliflower mosaic virus (CaMV), octopine synthase (ocs), Agrocateum, viral, and plant terminator sequences, or the like.

The terms "3' non-coding sequences" or "3' untranslated region (UTR)" refer to DNA sequences located downstream (3') of a coding sequence and may comprise polyadenylation [poly(A)] recognition sequences and other sequences encoding regulatory signals capable of affecting mRNA processing or gene expression. The polyadenylation signal, is usually characterized by affecting the addition of polyadenylic acid tracts to the 3' end of the mRNA precursor.

"Regulatory region" means a nucleic acid sequence which regulates the expression of a second nucleic acid sequence. A regulatory region may include sequences which are naturally responsible for expressing a particular nucleic acid (a homologous region) or may include sequences of a different origin that are responsible for expressing different proteins or even synthetic proteins (a heterologous region). In particular, the sequences can be sequences of prokaryotic, eukaryotic, or viral genes or derived sequences that stimulate or repress transcription of a gene in a specific or non-specific manner and in an inducible or non-inducible manner. Regulatory regions include origins of replication, RNA splice sites, promoters, enhancers, transcriptional termination sequences, and signal sequences which direct the polypeptide into the secretory pathways of the target cell.

A regulatory region from a "heterologous source" is a regulatory region that is not naturally associated with the expressed nucleic acid. Included among the heterologous regulatory regions are regulatory regions from a different species, regulatory regions from a different gene, hybrid regulatory sequences, and regulatory sequences which do not occur in nature, but which are designed by one having ordinary skill in the art.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene. The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

A "polypeptide" is a polymeric compound comprised of covalently linked amino acid residues. Amino acids have the following general structure:

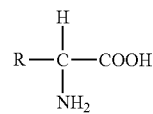

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. A polypeptide of the invention preferably comprises at least about 14 amino acids.

A "protein" is a polypeptide that performs a structural or functional role in a living cell.

An "isolated polypeptide" or "isolated protein" is a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which may be present, for example, due to incomplete purification, addition of stabilizers, or compounding into a pharmaceutically acceptable preparation.

"Fragment" of a polypeptide according to the invention will be understood to mean a polypeptide whose amino acid sequence is shorter than that of the reference polypeptide and which comprises, over the entire portion with these reference polypeptides, an identical amino acid sequence. Such fragments may, where appropriate, be included in a larger polypeptide of which they are a part. Such fragments of a polypeptide according to the invention may have a length of 10, 15, 20, 30 to 40, 50, 100, 200 or 300 amino acids.

A "variant" of a polypeptide or protein is any analogue, fragment, derivative, or mutant which is derived from a polypeptide or protein and which retains at least one biological property of the polypeptide or protein. Different variants of the polypeptide or protein may exist in nature. These variants may be allelic variations characterized by differences in the nucleotide sequences of the structural gene coding for the protein, or may involve differential splicing or post-translational modification. The skilled artisan can produce variants having single or multiple amino acid substitutions, deletions, additions, or replacements. These variants may include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining these variants, including genetic (suppressions, deletions, mutations, etc.), chemical, and enzymatic techniques, are known to persons having ordinary skill in the art. A variant polypeptide preferably comprises at least about 14 amino acids.

A "heterologous protein" refers to a protein not naturally produced in the cell.

A "mature protein" refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "homology" refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667). Such proteins (and their encoding genes) have sequence homology, as reflected by their high degree of sequence similarity.

Accordingly, the term "sequence similarity" in all its grammatical forms refers to the degree of identity or correspondence between nucleic acid or amino acid sequences of proteins that may or may not share a common evolutionary origin (see Reeck et al., 1987, Cell 50:667). As used herein, the term "homologous" in all its grammatical forms and spelling variations refers to the relationship between proteins that possess a "common evolutionary origin," including proteins from superfamilies and homologous proteins from different species (Reeck et al., supra). Such proteins (and their encoding genes) have sequence homology, as reflected by their high degree of sequence similarity. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences. Each of the proposed modifications is well within the routine skill in the art, as is determination of retention of biological activity of the encoded products.

Moreover, the skilled artisan recognizes that substantially similar sequences encompassed by this invention are also defined by their ability to hybridize, under stringent conditions (0.1×SSC, 0.1% SDS, 65° C. and washed with 2×SSC, 0.1% SDS followed by 0.1×SSC, 0.1% SDS), with the sequences exemplified herein. Substantially similar nucleic acid fragments of the instant invention are those nucleic acid fragments whose DNA sequences are at least 70% identical to the DNA sequence of the nucleic acid fragments reported herein. Preferred substantially nucleic acid fragments of the instant invention are those, nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Even more preferred are nucleic acid fragments that are at least 95% identical to the DNA sequence of the nucleic acid fragments reported herein.

Two amino acid sequences are "substantially homologous" or "substantially similar" when greater than about 40% of the amino acids are identical, or greater than 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer to similar or homologous sequences, whether the exact position is identical or different from the molecule to which the similarity or homology is measured. A nucleic acid or amino acid sequence alignment may include spaces. Thus, the term "corresponding to" refers to the sequence similarity, and not the numbering of the amino acid residues or nucleotide bases.

A "substantial portion" of an amino acid or nucleotide sequence comprises enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410; see also www.ncbi.nlm.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASER-GENE bioinformatics computing suite (DNASTAR Inc., Madison, Wis.). Multiple alignment of the sequences may be performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method may be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

Gene Expression Modulation System of the Invention

Applicants have now shown that separating the transactivation and DNA binding domains by placing them on two different proteins results in greatly reduced background activity in the absence of a ligand and significantly increased activity over background in the presence of a ligand. Applicants' improved gene expression system comprises two chimeric gene expression; the first encoding a DNA binding domain fused to a nuclear receptor polypeptide and the second encoding a transactivation domain fused to a nuclear receptor polypeptide. The interaction of the first protein with the second protein effectively tethers the DNA binding domain to the transactivation domain. Since the DNA binding and transactivation domains reside on two different molecules, the background activity in the absence of ligand is greatly reduced.

In general, the inducible gene expression modulation system of the invention comprises a) a first chimeric gene that is capable of being expressed in a host cell comprising a polynucleotide sequence that encodes a first hybrid polypeptide comprising i) a DNA-binding domain that recognizes a response element associated with a gene whose expression is to be modulated; and ii) a ligand binding domain comprising the ligand binding domain from a nuclear receptor; and b) a second chimeric gene that is capable of being expressed in the host cell comprising a polynucleotide sequence that encodes a second hybrid polypeptide comprising: i) a transactivation domain; and a ligand binding domain comprising the ligand binding domain from a nuclear receptor other than ultraspiracle (USP); wherein the transactivation domain are from other than EcR, RXR, or USP; and wherein the ligand binding domains from the first hybrid polypeptide and the second hybrid polypeptide are different and dimerize.

This two-hybrid system exploits the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283,173). This two-hybrid system is a significantly improved inducible gene expression modulation system compared to the two systems disclosed in International Patent Applications PCT/US97/05330 and PCT/US98/14215.

The ecdysone receptor-based gene expression modulation system of the invention may be either heterodimeric and homodimeric. A functional EcR complex generally refers to a heterodimeric protein complex consisting of two members of the steroid receptor family, an ecdysone receptor protein obtained from various insects, and an ultraspiracle (USP) protein or the vertebrate homolog of USP, retinoid X receptor protein (see Yao, et al. (1993) Nature 366, 476-479; Yao, et al., (1992) Cell 71, 63-72). However, the complex may also be a homodimer as detailed below. The functional ecdysteroid receptor complex may also include additional protein(s) such as immunophilins. Additional members of the steroid receptor family of proteins, known as transcriptional factors (such as DHR38 or betaFTZ-1), may also be ligand dependent or independent partners for EcR, USP, and/or RXR. Additionally, other cofactors may be required such as proteins generally known as coactivators (also termed adapters or mediators). These proteins do not bind sequence-specifically to DNA and are not involved in basal transcription. They may exert their effect on transcription activation through various mechanisms, including stimulation of DNA-binding of activators, by affecting chromatin structure, or by mediating activator-initiation complex interactions. Examples of such coactivators include RIP140, TIF1, RAP46/Bag-1, ARA70, SRC-1/NCoA-1, TIF2/GRIP/NCoA-2, ACTR/AIB1/RAC3/pCIP as well as the promiscuous coactivator C response element B binding protein, CBP/p300 (for review see Glass et al, Curr. Opin. Cell Biol. 9:222-232, 1997). Also, protein cofactors generally known as corepressors (also known as repressors, silencers, or silencing mediators) may be required to effectively inhibit transcriptional activation in the absence of ligand. These corepressors may interact with the unliganded ecdysone receptor to silence the activity at the response element. Current evidence suggests that binding of ligand changes the conformation of the receptor, which results in release of the corepressor and recruitment of the above described coactivators, thereby abolishing their silencing activity. Examples of corepressors include N—CoR and SMRT (for review, see Horwitz et al. Mol Endocrinol. 10: 1167-1177, 1996). These cofactors may either be endogenous within the cell or organism, or may be added exogenously as transgenes to be expressed in either a regulated or unregulated fashion. Homodimer complexes of the ecdysone receptor protein, USP, or RXR may also be functional under some circumstances.

The ecdysone receptor complex typically includes proteins which are members of the nuclear receptor superfamily wherein all members are characterized by the presence of an amino-terminal transactivation domain, a DNA binding domain ("DBD"), and a ligand binding domain ("LBD") separated from the DBD by a hinge region. As used herein, the term "DNA binding domain" comprises a minimal peptide sequence of a DNA binding protein, up to the entire length of a DNA binding protein, so long as the DNA binding domain functions to associate with a particular response element. Members of the nuclear receptor superfamily are also characterized by the presence of four or five domains: A/B, C, D, E, and in some members F (see Evans, Science 240:889-895 (1988)). The "A/B" domain corresponds to the transactivation domain, "C" corresponds to the DNA binding domain, "D" corresponds to the binge region, and "E" corresponds to the ligand binding domain. Some members of the family may also have another transactivation domain on the carboxy-terminal side of the LBD corresponding to "F".

The DBD is characterized by the presence of two cysteine zinc fingers between which are two amino acid motifs, the P-box and the D-box, which confer specificity for ecdysone response elements. These domains may be either native, modified, or chimeras of different domains of heterologous receptor proteins. This EcR receptor, like a subset of the steroid receptor family, also possesses less well defined regions responsible for heterodimerization properties. Because the domains of EcR, USP, and RXR are modular in nature, the LBD, DBD, and transactivation domains may be interchanged.

Gene switch systems are known that incorporate components from the ecdysone receptor complex. However, in these known systems, whenever EcR is used it is associated with native or modified DNA binding domains and transactivation domains on the same molecule. USP or RXR are typically used as silent partners. We have now shown that when DNA binding domains and transactivation domains are on the same molecule the background activity in the absence of ligand is high and that such activity is dramatically reduced when DNA binding domains and transactivation domains are on different molecules, that is, on each of two partners of a heterodimeric or homodimeric complex. This two-hybrid system also provides improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provide higher activity at a lower concentration. In addition, since transactivation based on EcR gene switches is often cell-line dependent, it is easier to tailor switching system to obtain maximum transactivation capability for each application. Furthermore, this two-hybrid system avoids some side effects due to overexpression of RXR that often occur when unmodified RXR is used as a switching partner. In this two-hybrid system, native DNA binding and transactivation domains of EcR or RXR are eliminated. As a result, these chimeric molecules have less chance of interacting with other steroid hormone receptors present in the cell resulting in reduced side effects.

Specifically, Applicants' invention relates to a gene expression modulation system comprising: a) a first gene expression cassette that is capable of being expressed in a host cell, wherein the first gene expression cassette comprises a polynucleotide that encodes a first polypeptide comprising i) a DNA-binding domain that recognizes a response element associated with a gene whose expression is to be modulated; and a ligand binding domain comprising a ligand binding domain from a nuclear receptor; and b) a second gene expression cassette that is capable of being expressed in the host cell, wherein the second gene expression cassette comprises a polynucleotide sequence that encodes a second polypeptide comprising i) a transactivation domain; and ii) a ligand binding domain comprising a ligand binding domain from a nuclear receptor other than ultraspiracle (USP); wherein the DNA binding domain and the transactivation domain are from other than EcR, RXR, or USP; wherein the ligand binding domains from the first polypeptide and the second polypeptide are different and dimerize.

The present invention also relates to a gene expression modulation system according to the present invention further comprising c) a third gene expression cassette comprising: i) the response element to which the DNA-binding domain of the first polypeptide binds; i) a promoter that is activated by the transactivation domain of the second polypeptide; and iii) the gene whose expression is to be modulated.

In a specific embodiment, the gene whose expression is to be modulated is a homologous gene with respect to the host cell. In another specific embodiment, the gene whose expression is to be modulated is a heterologous gene with respect to the host cell.

In a specific embodiment, the ligand binding domain of the first polypeptide comprises an ecdysone receptor ligand binding domain.

In another specific embodiment, the ligand binding domain of the first polypeptide comprises a retinoid X receptor ligand binding domain.

In a specific embodiment, the ligand binding domain of the second polypeptide comprises an ecdysone receptor ligand binding domain.

In another specific embodiment, the ligand binding domain of the second polypeptide comprises a retinoid X receptor ligand binding domain.

In a preferred embodiment, the ligand binding domain of the first polypeptide comprises an ecdysone receptor ligand binding domain, and the ligand binding domain of the second polypeptide comprises a retinoid X receptor ligand binding domain.

In another preferred embodiment, the ligand binding domain of the first polypeptide is from a retinoid X receptor polypeptide, and the ligand binding domain of the second polypeptide is from an ecdysone receptor polypeptide.

Preferably, the ligand binding domain is an EcR or RXR related steroid/thyroid hormone nuclear receptor family member ligand binding domain, or analogs, combinations, or modifications thereof. More preferably, the LBD is from EcR or RXR. Even more preferably, the LBD is from a truncated EcR or RXR. A truncation mutation may be made by any method used in the art, including but not limited to restriction endonuclease digestion/deletion, PCR-mediated/oligonucleotide-directed deletion, chemical mutagenesis, UV strand breakage, and the like.

Preferably, the EcR is an insect EcR selected from the group consisting of a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"), a *Tenebrio molitor* EcR ("TmEcR"), a *Manduca sexta* EcR ("MsEcR"), a *Heliothies virescens* EcR ("HvEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Uca pugilator* EcR ("UpEcR"), or an ixodid tick *Amblyomma americanum* EcR ("AmaEcR"). Even more preferably, the LBD is from spruce budworm (*Choristoneura fumiferana*) EcR ("CfEcR") or fruit fly *Drosophila melanogaster* EcR ("DmEcR").

Preferably, the LBD is from a truncated insect EcR. The insect EcR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 25, 240, 245, 250, 255, 260, or 265 amino acids. More preferably, the insect EcR polypeptide truncation comprises a deletion of at least a partial polypeptide domain. Even more preferably, the insect EcR polypeptide truncation comprises a deletion of at least an entire polypeptide domain. In a specific embodiment, the insect EcR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the ecdysone receptor ligand binding domain is encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the ecdysone receptor ligand binding domain comprises a polypeptide sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

Preferably, the RXR polypeptide is a mouse *Mus musculus* RXR ("MmRXR") or a human *Homo sapiens* RXR ("HsRXR"). The RXR polypeptide may be an $RXR_\alpha$, $RXR_\beta$, or RXR isoform.

Preferably, the LBD is from a truncated RXR. The RXR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the RXR polypeptide truncation comprises a deletion of at least a partial polypeptide domain. Even more preferably, the RXR polypeptide truncation comprises a deletion of at least an entire polypeptide domain. In a specific embodiment, the RXR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the retinoid X receptor ligand binding domain is encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the retinoid X receptor ligand binding domain comprises a polypeptide sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

For purposes of this invention EcR and RXR also include synthetic and chimeric EcR and RXR and their homologs.

The DNA binding domain can be any DNA binding domain with a known response element, including synthetic and chimeric DNA binding domains, or analogs, combinations, or modifications thereof. Preferably, the DBD is a GAL4 DBD, a LexA DBD, a transcription factor DBD, a steroid/thyroid hormone nuclear receptor superfamily member DBD, a bacterial LacZ DBD, or a yeast put DBD. More preferably, the DBD is a GAL4 DBD [SEQ ID NO: 41 (polynucleotide) or SEQ ID NO: 42 (polypeptide)] or a LexA DBD [(SEQ ID NO: 43 (polynucleotide) or SEQ ID NO: 44 (polypeptide)].

The transactivation domain (abbreviated "AD" or "TA") may be any steroid/thyroid hormone nuclear receptor AD, synthetic or chimeric AD, polyglutamine AD, basic or acidic amino acid AD, a VP16 AD, a GAL4 AD, an NF-κB AD, a BP64 AD, or an analog, combination, or modification thereof. Preferably, the AD is a synthetic or chimeric AD, or is obtained from a VP16, GAL4, or NF-κB. Most preferably, the AD is a VP16 AD [SEQ ID NO: 45 (polynucleotide) or SEQ ID NO: 46 (polypeptide)].

The response element ("RE") may be any response element with a known DNA binding domain, or an analog, combination, or modification thereof. Preferably, the RE is an RE from GAL4 ("GAL4RE"), LexA, a steroid/thyroid hormone nuclear receptor RE, or a synthetic RE that recognizes a synthetic DNA binding domain. More preferably, the RE is a GAL4RE comprising a polynucleotide sequence of SEQ ID NO: 47 or a LexA 8X operon comprising a polynucleotide sequence of SEQ ID NO: 48. Preferably, the first hybrid protein is substantially free of a transactivation domain and the second hybrid protein is substantially free of a DNA binding domain. For purposes of this invention, "substantially free" means that the protein in question does not contain a sufficient sequence of the domain in question to provide activation or binding activity.

The ligands for use in the present invention as described below, when combined with the ligand binding domain of an EcR USP, RXR, or another polypeptide which in turn are bound to the response element linked to a gene, provide the means for external temporal regulation of expression of the gene. The binding mechanism or the order in which the various components of this invention bind to each other, that is, ligand to receptor, first polypeptide to response element, second polypeptide to promoter, etc., is not critical. Binding of the ligand to the ligand binding domains of an EcR, USP, RXR, or another protein, enables expression or suppression of the gene. This mechanism does not exclude the potential for ligand binding to EcR, USP, or RXR, and the resulting formation of active homodimer complexes (e.g. EcR+EcR or USP+USP). Preferably, one or more of the receptor domains can be varied producing a chimeric gene switch. Typically, one or more of the three domains, DBD, LBD, and transactivation domain, may be chosen from a source different than the source of the other domains so that the chimeric genes and the resulting hybrid proteins are optimized in the chosen host cell or organism for transactivating activity, complementary binding of the ligand, and recognition of a specific response element. In addition, the response element itself can be modified or substituted with response elements for other DNA binding protein domains such as the GAL-4 protein from yeast (see Sadowski, et al. (1988) Nature, 335:563-564) or LexA protein from *E. coli* (see Brent and Ptashne (1985), Cell, 43:729-736), or synthetic response elements specific for targeted interactions with proteins designed, modified, and selected for such specific interactions (see, for example, Kim, et al. (1997), *Proc. Natl. Acad. Sci., USA*, 94:3616-3620) to accommodate chimeric receptors. Another advantage of chimeric systems is that they allow choice of a promoter used to drive the gene expression according to a desired end result. Such double control can be particularly important in areas of gene therapy, especially when cytotoxic proteins are produced, because both the timing of expression as well as the cells wherein expression occurs can be controlled. When genes, operatively linked to a suitable promoter, are introduced into the cells of the subject, expression of the exogenous genes is controlled by the presence of the system of this invention. Promoters may be constitutively or inducibly regulated or may be tissue-specific (that is, expressed only in a particular type of cells) or specific to certain developmental stages of the organism Gene Expression Cassettes of the Invention The novel ecdysone receptor-based inducible gene expression system of the invention comprises a novel gene expression cassette that is capable of being expressed j a host cell, wherein the gene expression cassette comprises a polynucleotide encoding a hybrid polypeptide. Thus, Applicants' invention also provides novel gene expression cassettes for use in the gene expression system of the invention.

Specifically, the present invention provides a gene expression cassette comprising a polynucleotide encoding a hybrid polypeptide. The hybrid polypeptide comprises either 1) a DNA-binding domain that recognizes a response element and a ligand binding domain of a nuclear receptor or 2) a transactivation domain and a ligand binding domain of a nuclear receptor, wherein the transactivation domain is from a nuclear receptor other than an EcR, an RXR, or a USP.

In a specific embodiment, the gene expression cassette encodes a hybrid polypeptide comprising a DNA-binding domain that recognizes a response element and an ecdysone receptor ligand binding domain, wherein the DNA binding domain is from a nuclear receptor other than an ecdysone receptor.

In another specific embodiment, the gene expression cassette encodes a hybrid polypeptide comprising a DNA-binding domain that recognizes a response element and a retinoid X receptor ligand binding domain, wherein the DNA binding domain is from a nuclear receptor other than a retinoid X receptor.

The DNA binding domain can be any DNA binding domain with a known response element, including synthetic, and chimeric DNA binding domains, or analogs, combinations, or modifications thereof. Preferably, the DBD is a GAL4 DBD, a LexA DBD, a transcription factor DBD, a steroid/thyroid hormone nuclear receptor superfamily member DBD, a bacterial LacZ DBD, or a yeast put DBD. More preferably, the DBD is a GAL4 DBD [SEQ ID NO: 41 (polynucleotide) or SEQ ID NO: 42 (polypeptide)] or a LexA DBD [(SEQ ID NO: 43 (polynucleotide) or SEQ ID NO: 44 (polypeptide)].

In another specific embodiment, the gene expression cassette encodes a hybrid polypeptide comprising a transactivation domain and an ecdysone receptor ligand binding domain, wherein the transactivation domain is from a nuclear receptor other than an ecdysone receptor.

In another specific embodiment, the gene expression cassette encodes a hybrid polypeptide comprising a transactivation domain and a retinoid X receptor ligand binding domain, wherein the transactivation domain is from a nuclear receptor other than a retinoid X receptor.

The transactivation domain (abbreviated "AD" or "TA") may be any steroid/thyroid hormone nuclear receptor AD, synthetic or chimeric AD, polyglutamine AD, basic or acidic amino acid AD, a VP16 AD, a GAL4 AD, an NF-κB AD, a BP64 AD, or an analog, combination, or modification thereof. Preferably, the AD is a synthetic or chimeric AD, or is obtained from a VP16, GAL4, or NF-κB. Most preferably, the AD is a VP16 AD [SEQ ID NO: 45 (polynucleotide) or SEQ ID NO: 46 (polypeptide)].

Preferably, the ligand binding domain is an EcR or RXR related steroid/thyroid hormone nuclear receptor family member ligand binding domain, or analogs, combinations, or modifications thereof. More preferably, the LBD is from EcR or RXR. Even more preferably, the LBD is from a truncated EcR or RXR.

Preferably, the EcR is an insect EcR selected from the group consisting of a Lepidopteran EcR, a Dipteran EcR, an Arthropod EcR, a Homopteran EcR and a Hemipteran EcR. More preferably, the EcR for use is a spruce budworm *Choristoneura fumiferana* EcR ("CfEcR"), a *Tenebrio molitor* EcR ("TmEcR"), a *Manduca sexta* EcR ("MsEcR"), a *Heliothies virescens* EcR ("HvEcR"), a silk moth *Bombyx mori* EcR ("BmEcR"), a fruit fly *Drosophila melanogaster* EcR ("DmEcR"), a mosquito *Aedes aegypti* EcR ("AaEcR"), a blowfly *Lucilia capitata* EcR ("LcEcR"), a Mediterranean fruit fly *Ceratitis capitata* EcR ("CcEcR"), a locust *Locusta migratoria* EcR ("LmEcR"), an aphid *Myzus persicae* EcR ("MpEcR"), a fiddler crab *Uca pugilator* EcR ("UpEcR"), or an ixodid tick *Amblyomma americanum* EcR ("AmaEcR"). Even more preferably, the LBD is from spruce budworm (*Choristoneura fumiferana*) EcR ("CfEcR") or fruit fly *Drosophila melanogaster* EcR ("DmEcR").

Preferably, the LBD is from a truncated insect EcR. The insect EcR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the insect EcR polypeptide truncation comprises a deletion of at least a partial polypeptide domain. Even more preferably, the insect EcR polypeptide truncation comprises a deletion of at least an entire polypeptide domain. In a specific embodiment, the insect EcR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the ecdysone receptor ligand binding domain is encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the ecdysone receptor ligand binding domain comprises an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

Preferably, the RXR polypeptide is a mouse *Mus musculus* RXR ("MmRXR") or a human *Homo sapiens* RXR ("HsRXR"). The RXR polypeptide may be an $RXR_\alpha$, $RXR_\beta$, or $RXR_\gamma$ isoform.

Preferably, the LBD is from a truncated RXR. The RXR polypeptide truncation comprises a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the RXR polypeptide truncation comprises a deletion of at least a partial polypeptide domain. Even more preferably, the RXR polypeptide truncation comprises a deletion of at least an entire polypeptide domain. In a specific embodiment, the RXR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the retinoid X receptor ligand binding domain is encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the retinoid X receptor ligand binding domain comprises an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In a preferred embodiment, the gene expression cassette encodes a hybrid polypeptide comprising a DNA-binding domain encoded by a polynucleotide comprising a nucleic acid sequence selected from the group consisting of a GAL4 DBD (SEQ IL NO: 41) or a LexA DBD (SEQ ID NO: 43) and an ecdysone receptor ligand binding domain encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the gene expression cassette encodes a hybrid polypeptide comprising a DNA-binding domain comprising a polypeptide sequence selected from the group consisting of a GAL4 DBD (SEQ ID NO: 42) or a LexA DBD (SEQ ID NO: 44) and an ecdysone receptor ligand binding domain comprising an amino acid sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a DNA-binding domain encoded by a polynucleotide comprising a nucleic acid sequence selected from the group consisting of a GAL4 DBD (SEQ ID NO: 41) or a LexA DBD (SEQ ID NO: 43) and a retinoid X receptor ligand binding domain encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the gene expression cassette encodes a hybrid polypeptide comprising a DNA-binding domain comprising a polypeptide sequence selected from the group consisting of a GAL4 DBD (SEQ ID NO: 42) or a LexA DBD (SEQ ID NO: 44) and a retinoid X receptor ligand binding domain comprising an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

In another preferred embodiment, the gene expression cassette encodes a hybrid polypeptide comprising a transactivation domain encoded by a polynucleotide comprising a nucleic acid sequence of SEQ ID NO: 45 and an ecdysone receptor ligand binding domain encoded by a polynucleotide comprising a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10.

In another preferred embodiment, the gene expression cassette encodes a hybrid polypeptide comprising a transactivation domain comprising a polypeptide sequence of SEQ ID NO: 46 and an ecdysone receptor ligand binding domain comprising a polypeptide sequence selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, and SEQ ID NO: 20.

In another preferred embodiment, the gene expression cassette encodes a hybrid polypeptide comprising a transactivation domain encoded by a polynucleotide comprising a nucleic acid sequence of SEQ ID NO: 45 and a retinoid X receptor ligand binding domain encoded by a polynucleotide comprising a nucleic acid sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In another preferred embodiment, the gene expression cassette encodes a hybrid polypeptide comprising a transactivation domain comprising a polypeptide sequence of SEQ ID NO: 46 and a retinoid X receptor ligand binding domain comprising an amino acid sequence selected from the group consisting of SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, and SEQ ID NO: 40.

For purposes of this invention EcR and RXR also include synthetic and chimeric EcR and RXR and their homologs.

Polynucleotides of the Invention

The novel ecdysone receptor-based inducible gene expression system of the invention comprises a gene expression cassette comprising a polynucleotide that encodes a truncated EcR or RXR polypeptide comprising a truncation mutation and is useful in methods of modulating the expression of a gene within a host cell.

Thus, the present invention also relates to a polynucleotide that encodes an EcR or RXR polypeptide comprising a truncation mutation. Specifically, the present invention relates to an isolated polynucleotide encoding an EcR or RXR polypeptide comprising a truncation mutation that affects ligand binding activity or ligand sensitivity.

Preferably, the truncation mutation results in a polynucleotide that encodes a truncated EcR polypeptide or a truncated RXR polypeptide comprising a deletion of at least 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the EcR or RXR polypeptide truncation comprises a deletion of at least a partial polypeptide domain. Even more preferably, the EcR or RXR polypeptide truncation comprises a deletion of at least an entire polypeptide domain. In a specific embodiment, the EcR or RXR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a specific embodiment, the EcR polynucleotide according to the invention comprises a polynucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, and SEQ ID NO: 10. In a specific embodiment, the polynucleotide according to the invention encodes a ecdysone receptor polypeptide comprising an amino acid sequence selected from the group consisting of SEQ ID NO: 11 (CfEcR-CDEF), SEQ ID NO: 12 (CfEcR-1/2CDEF, which comprises the last 33 carboxy-terminal amino acids of C domain), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-1/2CDEF), SEQ ID NO: 18 (DmEcR-DEF), SEQ ID NO: 19 (DmEcR-EF), and SEQ ID NO: 20 (DmEcR-DE).

In another specific embodiment, the RXR polynucleotide according to the invention comprises a polynucleotide sequence selected from the group consisting of SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30. In another specific embodiment, the polynucleotide according to the invention encodes a truncated RXR polypeptide comprising an amino acid sequence consisting of SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncated EF), and SEQ ID NO: 40 (HsRXR-E).

In particular, the present invention relates to an isolated polynucleotide encoding an EcR or RXR polypeptide comprising a truncation mutation, wherein the mutation reduces ligand binding activity or ligand sensitivity of the EcR or RXR polypeptide. In a specific embodiment, the present invention relates to an isolated polynucleotide encoding an EcR or RXR polypeptide comprising a truncation mutation that reduces steroid binding activity or steroid sensitivity of the EcR or RXR polypeptide. In a preferred embodiment, the present invention relates to an isolated polynucleotide encoding an EcR polypeptide comprising a truncation mutation that reduces steroid binding activity or steroid sensitivity of the EcR polypeptide, wherein the polynucleotide comprises a nucleic acid sequence of SEQ ID NO: 3 (CfEcR-DEF), SEQ ID NO: 4 (CfEcR-EF), SEQ ID NO: 8 (DmEcR-DEF), or SEQ ID NO: 9 (DmEcR-EF). In another specific embodiment, the present invention relates to an isolated polynucleotide encoding an EcR or RXR polypeptide comprising a truncation mutation that reduces non-steroid binding activity or non-steroid sensitivity of the EcR or RXR polypeptide. In a preferred embodiment, the present invention relates to an isolated polynucleotide encoding an EcR polypeptide comprising a truncation mutation that reduces non-steroid binding activity or non-steroid sensitivity of the EcR polypeptide, wherein the polynucleotide comprises a nucleic acid sequence of SEQ ID NO: 4 (CfEcR-EF) or SEQ ID NO: 9 (DmEcR-EF).

The present invention also relates to an isolated polynucleotide encoding an EcR or RXR polypeptide comprising a truncation mutation, wherein the mutation enhances ligand binding activity or ligand sensitivity of the EcR or RXR polypeptide. In a specific embodiment, the present invention relates to an isolated polynucleotide encoding an EcR or RXR polypeptide comprising a truncation mutation that enhances steroid binding activity or steroid sensitivity of the EcR or RXR polypeptide. In another specific embodiment, the present invention relates to an isolated polynucleotide encoding an EcR or RXR polypeptide comprising a truncation mutation that enhances non-steroid binding activity or non-steroid sensitivity of the EcR or RXR polypeptide. In a preferred embodiment, the present invention relates to an isolated polynucleotide encoding an EcR polypeptide comprising a truncation mutation that enhances non-steroid binding activity or non-steroid sensitivity of the EcR polypeptide, wherein the polynucleotide comprises a nucleic acid sequence of SEQ ID NO: 3 (CfEcR-DEF) or SEQ NO: 8 (DmEcR-DEF).

The present invention also relates to an isolated polynucleotide encoding a retinoid X receptor polypeptide comprising a truncation mutation that increases ligand sensitivity of a heterodimer comprising the mutated retinoid X receptor polypeptide and a dimerization partner. Preferably, the isolated polynucleotide encoding a retinoid X receptor polypeptide comprising a truncation mutation that increases ligand sensitivity of a heterodimer comprises a polynucleotide sequence selected from the group consisting of SEQ ID NO: 23 (MmRXR-EF), SEQ ID NO: 24 (MmRXR-truncatedEF), SEQ ID NO: 28 (HsRXR-EF), or SEQ ID NO: 29 (HsRXR-truncated EF). In a specific embodiment, the dimerization partner is an ecdysone receptor polypeptide. Preferably, the dimerization partner is a truncated EcR polypeptide. More preferably, the dimerization partner is an EcR polypeptide in which domains A/B/C have been deleted. Even more preferably, the dimerization partner is an EcR polypeptide comprising an amino acid sequence of SEQ ID NO: 13 (CfEcR-DEF) or SEQ ID NO: 18 (DmEcR-DEF).

Polypeptides of the Invention

The novel ecdysone receptor-based inducible gene expression system of the invention comprises a polynucleotide that encodes a truncated EcR or RXR polypeptide and is useful in methods of modulating the expression of a gene within a host cell. Thus, the present invention also relates to an isolated truncated EcR or RXR polypeptide encoded by a polynucleotide or a gene expression cassette according to the invention. Specifically, the present invention relates to an isolated truncated EcR or RXR polypeptide comprising a truncation mutation that affects ligand binding activity or ligand sensitivity encoded by a polynucleotide according to the invention.

The present invention also relates to an isolated truncated EcR or RXR polypeptide comprising a truncation mutation. Specifically, the present invention relates to an isolated EcR or RXR polypeptide comprising a truncation mutation that affects ligand binding activity or ligand sensitivity.

Preferably, the truncation mutation results in a truncated EcR polypeptide or a truncated RXR polypeptide comprising a deletion of at least 1, 2, 3, 4, 5, 10, 15, 20, 25, 30, 35, 40, 45, 50, 55, 60, 65, 70, 75, 80, 85, 90, 95, 100, 105, 110, 11.5, 120, 125, 130, 135, 140, 145, 150, 155, 160, 165, 170, 175, 180, 185, 190, 195, 200, 205, 210, 215, 220, 225, 230, 235, 240, 245, 250, 255, 260, or 265 amino acids. More preferably, the EcR or RXR polypeptide truncation comprises a deletion of at least a partial polypeptide domain. Even more preferably, the EcR or RXR polypeptide truncation comprises a deletion of at least an entire polypeptide domain. In a specific embodiment, the EcR or RXR polypeptide truncation comprises a deletion of at least an A/B-domain deletion, a C-domain deletion, a D-domain deletion, an E-domain deletion, an F-domain deletion, an A/B/C-domains deletion, an A/B/1/2-C-domains deletion, an A/B/C/D-domains deletion, an A/B/C/D/F-domains deletion, an A/B/F-domains, and an A/B/C/F-domains deletion. A combination of several complete and/or partial domain deletions may also be performed.

In a preferred embodiment, the isolated truncated ecdysone receptor polypeptide is encoded by a polynucleotide comprising a polynucleotide sequence selected from the group consisting of SEQ ID NO: 1 (CfEcR-CDEF), SEQ ID NO: 2 (CfEcR-1/2CDEF), SEQ ID NO: 3 (CfEcR-DEF), SEQ ID NO: 4 (CfEcR-EF), SEQ ID NO: 5 (CfEcR-DE), SEQ ID NO: 6 (DmEcR-CDEF), SEQ ID NO: 7 (DmEcR-1/2CDEF), SEQ ID NO: 8 (DmEcR-DEF), SEQ ID NO: 9 (DmEcR-EF), and SEQ ID NO: 10 (DmEcR-DE). In another preferred embodiment, the isolated truncated ecdysone receptor polypeptide comprises an amino acid sequence selected from the group consisting of SEQ ID NO: 11 (CfEcR-CDEF), SEQ ID NO: 12 (CfEcR-1/2CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-1/2CDEF), SEQ ID NO: 18 (DmEcR-DEF), SEQ ID NO: 19 (DmEcR-EF), and SEQ ID NO: 20 (DmEcR-DE).

In a preferred embodiment, the isolated truncated RXR polypeptide is encoded by a polynucleotide comprising a polynucleotide sequence selected from the group consisting of SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncatedEF) and SEQ ID NO: 30 (HsRXR-E). In another preferred embodiment, the isolated truncated RXR polypeptide comprises an amino acid sequence selected from the group consisting of SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncatedEF), and SEQ ID NO: 40 (HsRXR-E).

The present invention relates to an isolated EcR or RXR polypeptide comprising a truncation mutation that reduces ligand binding activity or ligand sensitivity of the EcR or RXR polypeptide, wherein the polypeptide is encoded by a polynucleotide comprising a polynucleotide sequence selected from the group consisting of SEQ ID NO: 1 (CfEcR-CDEF), SEQ ID NO: 2 (CfEcR-1/2CDEF), SEQ ID NO: 3 (CfEcR-DEF), SEQ ID NO: 4 (CfEcR-EF), SEQ ID NO: 5 (CfEcR-DE), SEQ ID NO: 6 (DmEcR-CDEF), SEQ ID NO: 7 (DmEcR-1/2CDEF), SEQ ID NO: 8 (DmEcR-DEF), SEQ ID NO: 9 (DmEcR-EF), SEQ ID NO: 10 (DmEcR-DE), SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncatedEF), and SEQ ID NO: 30 (HsRXR-E).

Thus, the present invention relates to an isolated truncated EcR or RXR polypeptide comprising a truncation mutation that reduces ligand binding activity or ligand sensitivity of the EcR or RXR polypeptide, wherein the polypeptide comprises an amino acid sequence selected from the group consisting of SEQ ID NO: 11 (CfEcR-CDEF), SEQ ID NO: 12 (CfEcR-1/2CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-1/2CDEF), SEQ ID NO: 18 (DmEcR-DEF), SEQ ID NO: 19 (DmEcR-EF), SEQ ID NO: 20 (DmEcR-DE), SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 38 (HsRXR-EF), SEQ ID NO: 39 (HsRXR-truncatedEF), and SEQ ID NO: 40 (HsRXR-E).

In a specific embodiment, the present invention relates to an isolated EcR or RXR polypeptide comprising a truncation mutation that reduces steroid binding activity or steroid sensitivity of the EcR or RXR polypeptide. In a preferred embodiment, the present invention relates to an isolated EcR polypeptide comprising a truncation mutation that reduces steroid binding activity or steroid sensitivity of the EcR polypeptide, wherein the EcR polypeptide is encoded by a polynucleotide comprising a nucleic acid sequence of SEQ ID NO: 3 (CfEcR-DEF), SEQ ID NO: 4 (CfEcR-EF), SEQ ID NO: 8 (DmEcR-DEF), or SEQ ID NO: 9 (DmEcR-EF). Accordingly, the present invention also relates to an isolated truncated EcR or RXR polypeptide comprising a truncation mutation that reduces steroid binding activity or steroid sensitivity of the EcR or RXR polypeptide. In a preferred embodiment, the present invention relates to an isolated EcR polypeptide comprising a truncation mutation that reduces steroid binding activity or steroid sensitivity of the EcR polypeptide, wherein the EcR polypeptide comprises an amino acid sequence of SEQ ID NO: 13 (CfEcR-DEF), SEQ ID NO: 14 (CfEcR-EF), SEQ ID NO: 18 (DmEcR-DEF), or SEQ ID NO: 19 (DmEcR-EF).

In another specific embodiment, the present invention relates to an isolated EcR or RXR polypeptide comprising a truncation mutation that reduces non-steroid binding activity or non-steroid sensitivity of the EcR or RXR polypeptide. In a preferred embodiment, the present invention relates to an isolated EcR polypeptide comprising a truncation mutation that reduces non-steroid binding activity or non-steroid sensitivity of the EcR polypeptide, wherein the EcR polypeptide is encoded by a polynucleotide comprising a nucleic acid sequence of SEQ ID NO: 4 (CfEcR-EF) or SEQ ID NO: 9 (DmEcR-EF). Accordingly, the present invention also relates to an isolated truncated EcR or RXR polypeptide comprising a truncation mutation that reduces non-steroid binding activity or steroid sensitivity of the EcR or RXR polypeptide. In a preferred embodiment, the present invention relates to an isolated EcR polypeptide comprising a truncation mutation that reduces non-steroid binding activity or non-steroid sensitivity of the EcR polypeptide, wherein the EcR polypeptide comprises an amino acid sequence of SEQ ID NO: 14 (CfEcR-EF) or SEQ ID NO: 19 (DmEcR-EF).

In particular, the present invention relates to an isolated EcR or RXR polypeptide comprising a truncation mutation that enhances ligand binding activity or ligand sensitivity of the EcR or RXR polypeptide, wherein the polypeptide is encoded by a polynucleotide comprising a polynucleotide sequence selected from the group consisting of SEQ ID NO: 1 (CfEcR-CDEF), SEQ ID NO: 2 (CfEcR-1/2CDEF), SEQ ID NO: 3 (CfEcR-DEF), SEQ ID NO: 4 (CfEcR-EF), SEQ ID NO: 5 (CfEcR-DE), SEQ ID NO: 6 (DmEcR-CDEF), SEQ ID NO: 7 (DmEcR-1/2CDEF), SEQ ID NO: 8 (DmEcR-DEF), SEQ ID NO: 9 (DmEcR-EF), SEQ ID NO: 10 (DmEcR-DE), SEQ ID NO: 21 (MmRXR-CDEF), SEQ ID NO: 22 (MmRXR-DEF), SEQ ID NO: 23 (MmRXR-EF), SEQ ID NO: 24 (MmRXR-truncatedEF), SEQ ID NO: 25 (MmRXR-E), SEQ ID NO: 26 (HsRXR-CDEF), SEQ ID NO: 27 (HsRXR-DEF), SEQ ID NO: 28 (HsRXR-EF), SEQ ID NO: 29 (HsRXR-truncated EF), and SEQ ID NO: 30 (HsRXR-E).

The present invention relates to an isolated EcR or RXR polypeptide comprising a truncation mutation that enhances ligand binding activity or ligand sensitivity of the EcR or RXR polypeptide, wherein the polypeptide comprises an amino acid sequence selected from the group consisting of SEQ ID NO: 11 (CfEcR-CDEF), SEQ ID NO: 12 (CfEcR-1/2CDEF), SEQ ID NO: 13 (CfEcR-DEF), SEQ ID NO: 14 (CfEcR-EF), SEQ ID NO: 15 (CfEcR-DE), SEQ ID NO: 16 (DmEcR-CDEF), SEQ ID NO: 17 (DmEcR-1/2CDEF), SEQ ID NO: 18 (DmEcR-DEF), SEQ ID NO: 19 (DmEcR-EF), SEQ ID NO: 20 (DmEcR-DE), SEQ ID NO: 31 (MmRXR-CDEF), SEQ ID NO: 32 (MmRXR-DEF), SEQ ID NO: 33 (MmRXR-EF), SEQ ID NO: 34 (MmRXR-truncatedEF), SEQ ID NO: 35 (MmRXR-E), SEQ ID NO: 36 (HsRXR-CDEF), SEQ ID NO: 37 (HsRXR-DEF), SEQ ID NO: 39 (HsRXR-EF), SEQ ID NO: 39 (HsRXR-truncatedEF), and SEQ ID NO: 40 (HsRXR-E).

The present invention relates to an isolated EcR or RXR polypeptide comprising a truncation mutation that enhances ligand binding activity or ligand sensitivity of the EcR or RXR polypeptide. In a specific embodiment, the present invention relates to an isolated EcR or RXR polypeptide comprising a truncation mutation that enhances steroid binding activity or steroid sensitivity of the EcR or RXR polypeptide. Accordingly, the present invention also relates to an isolated EcR or RXR polypeptide comprising a truncation mutation that enhances steroid binding activity or steroid sensitivity of the EcR or RXR polypeptide.

In another specific embodiment, the present invention relates to an isolated EcR or RXR polypeptide comprising a truncation mutation that enhances non-steroid binding activity or non-steroid sensitivity of the EcR or RXR polypeptide. In a preferred embodiment, the present invention relates to an isolated EcR polypeptide comprising a truncation mutation that enhances non-steroid binding activity or non-steroid sensitivity of the EcR polypeptide, wherein the EcR polypeptide is encoded by a polynucleotide comprising a nucleic acid sequence of SEQ ID NO: 3 (CfEcR-DEF) or SEQ ID NO: 8 (DmEcR-DEF). Accordingly, the present invention also relates to an isolated EcR or RXR polypeptide comprising a truncation mutation that enhances non-steroid binding activity or steroid sensitivity of the EcR or RXR polypeptide. In a preferred embodiment, the present invention relates to an isolated EcR polypeptide comprising a truncation mutation that enhances non-steroid binding activity or non-steroid sensitivity of the EcR polypeptide, wherein the EcR polynucleotide comprises an amino acid sequence of SEQ ID NO: 13 (CfEcR-DEF) or SEQ ID NO: 18 (DmEcR-DEF).

The present invention also relates to an isolated retinoid X receptor polypeptide comprising a truncation mutation that increases ligand sensitivity of a heterodimer comprising the mutated retinoid X receptor polypeptide and a dimerization partner. Preferably, the isolated retinoid X receptor polypeptide comprising a truncation mutation that increases ligand sensitivity of a heterodimer is encoded by a polynucleotide comprising a nucleic acid sequence selected from the group consisting of SEQ ID NO: 23 (MmRXR-EF), SEQ ID NO: 24

(MmRXR-truncatedEF), SEQ ID NO: 28 (HsRXR-EF), or SEQ ID NO: 29 (HsRXR-truncatedEF). More preferably, the isolated polynucleotide encoding a retinoid X receptor polypeptide comprising a truncation mutation that increases ligand sensitivity of a heterodimer comprises an amino acid sequence selected from the group consisting of SEQ ID NO: 33 (MmRXR-EF), SEQ ID NO: 34 (MmRXR-truncatedEF), SEQ ID NO: 38 (HsRXR-EF), or SEQ ID NO: 39 (HsRXR-truncatedEF).

In a specific embodiment, the dimerization partner is an ecdysone receptor polypeptide. Preferably, the dimerization partner is a truncated EcR polypeptide. More preferably, the dimerization partner is an EcR polypeptide in which domains A/B/C have been deleted. Even more preferably, the dimerization partner is an EcR polypeptide comprising an amino acid sequence of SEQ ID NO: 13 (CfEcR-DEF) or SEQ ID NO: 18 (DmEcR-DEF).

Method of Modulating Gene Expression of the Invention

Applicants' invention also relates to methods of modulating gene expression in a host cell using a gene expression modulation system according to the invention. Specifically, Applicants' invention provides a method of modulating the expression of a gene in a host cell comprising the steps of: a) introducing into the host cell a gene expression modulation system according to the invention; and b) introducing into the host cell a ligand that independently combines with the ligand binding domains of the first polypeptide and the second polypeptide of the gene expression modulation system; wherein the gene to be expressed is a component of a gene expression cassette comprising: i) a response element comprising a domain to which the DNA binding domain of the first polypeptide binds; ii) a promoter that is activated by the transactivation domain of the second polypeptide; and a gene whose expression is to be modulated, whereby a complex is formed comprising the ligand, the first polypeptide of the gene expression modulation system and the second polypeptide of the gene expression modulation system, and whereby the complex modulates expression of the gene in the host cell.

Genes of interest for expression in a host cell using Applicants' methods may be endogenous genes or heterologous genes. Nucleic acid or amino acid sequence information for a desired gene or protein can be located in one of many public access databases, for example, GENBANK, EMBL, Swiss-Prot, and PIR, or in many biology related journal publications. Thus, those skilled in the art have access to nucleic acid sequence information for virtually all known genes. Such information can then be used to construct the desired constructs for the insertion of the gene of interest within the gene expression cassettes used in Applicants' methods described herein.

Examples of genes of interest for expression in a host cell using Applicants' methods include, but are not limited to: antigens produced in plants as vaccines, enzymes like alpha-amylase, phytase, glucans, and xylanse, genes for resistance against insects, nematodes, fungi, bacteria, viruses, and abiotic stresses, nutraceuticals, pharmaceuticals, vitamins, genes for modifying amino acid content, herbicide resistance, cold, drought, and heat tolerance, industrial products, oils, protein, carbohydrates, antioxidants, male sterile plants, flowers, fuels, other output traits, genes encoding therapeutically desirable polypeptides or products, such as genes that can provide, modulate, alleviate, correct and/or restore polypeptides important in treating a condition, a disease, a disorder, a dysfunction, a genetic defect, and the like.

Acceptable ligands are any that modulate expression of the gene when binding of the DNA binding domain of the two hybrid system to the response element in the presence of the ligand results in activation or suppression of expression of the genes. Preferred ligands include ponasterone, muristerone A, N,N'-diacylhydrazines such as those disclosed in U.S. Pat. Nos. 6,013,836; 5,117,057; 5,530,028; and 5,378,726; dibenzoylalkyl cyanohydrazines such as those disclosed in European Application No. 461,809; N-alkyl-N,N'-diacylhydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; each of which is incorporated herein by reference and other similar materials including 3,5-di-tert-butyl-4-hydroxy-N-isobutyl-benzamide, 8-O-acetylharpagide, and the like.

Preferably, the ligand for use in Applicants' method of modulating expression of gene is a compound of the formula:

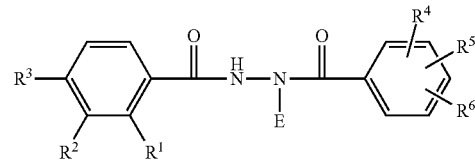

wherein:
E is a $(C_4-C_6)$alkyl containing a tertiary carbon or a cyano $(C_3-C_5)$alkyl containing a tertiary carbon;
$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH=CHCN, allyl, azido, SCN, or $SCHF_2$;
$R^2$ is H, Me, Et, n-Pr, i-Pr, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, Ac, F, Cl, OH, OMe, OEt, O-n-Pr, OAc, NMe2, $NEt_2$, SMe, SEt, $SOCF_3$, $OCF_2CF_2H$, COEt, cyclopropyl, $CF_2CF_3$, CH=CHCN, allyl, azido, $OCF_3$, $OCHF_2$, O-i-Pr, SCN, $SCHF_2$, $SOMe$, NH—CN, or joined with $R^3$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;
$R^3$ is H, Et, or joined with $R^2$ and the phenyl carbons to which $R^2$ and $R^3$ are attached to form an ethylenedioxy, a dihydrofuryl ring with the oxygen adjacent to a phenyl carbon, or a dihydropyryl ring with the oxygen adjacent to a phenyl carbon;
$R^4$, $R^5$, and $R^6$ are independently H, Me, Et, F, Cl, Br, formyl, $CF_5$, $CHF_2$, $CH_2F$, $CH_2Cl$, $CH_2OH$, CN, C≡CH, 1-propynyl, 2-propynyl, vinyl, OMe, OEt, SMe, or SEt.

Applicants' invention provides for modulation of gene expression in prokaryotic and eukaryotic host cells. Thus, the present invention also relates to a method for modulating gene expression in a host cell selected from the group consisting of a bacterial cell, a fungal cell, a yeast cell, a plant cell, an animal cell, and a mammalian cell. Preferably, the host cell is a yeast cell, a plant cell, a murine cell, or a human cell.

Expression in transgenic host cells may be useful for the expression of various polypeptides of interest including but not limited to therapeutic polypeptides, pathway intermediates; for the modulation of pathways already existing in the host for the synthesis of new products heretofore not possible using the host; cell based assays; and the like. Additionally the gene products may be useful for conferring higher growth yields of the host or for enabling alternative growth mode to be utilized.

Host Cells and Non-Human Organisms of the Invention

As described above, the gene expression modulation system of the present invention may be used to modulate gene expression in a host cell. Expression in transgenic host cells may be useful for the expression of various genes of interest. Thus, Applicants' invention also provides an isolated host cell comprising a gene expression system according to the invention. The present invention also provides an isolated host cell comprising a gene expression cassette according to the invention. Applicants' invention also provides an isolated host cell comprising a polynucleotide or polypeptide according to the invention. The isolated host cell may be either a prokaryotic or a eukaryotic host cell.

Preferably, the host cell is selected from the group consisting of a bacterial cell, a fungal cell, a yeast cell, a plant cell, an animal cell, and a mammalian cell. Examples of preferred host cells include, but are not limited to, fungal or yeast species such as *Aspergillus, Trichoderma, Saccharomyces, Pichia, Candida, Hansenula*, or bacterial species such as those in the genera *Synechocystis, Synechococcus, Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium* and *Klebsiella*, plant, animal, and mammalian host cells. More preferably, the host cell is a yeast cell, a plant cell, a murine cell, or a human cell.

In a specific embodiment, the host cell is a yeast cell selected from the group consisting of a *Saccharomyces*, a *Pichia*, and a *Candida* host cell.

In another specific embodiment, the host cell is a plant cell selected from the group consisting of an apple, *Arabidopsis*, bajra, banana, barley, bean, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, *sorghum*, soybean, squash, sugarcane, sugarbeet sunflower, sweet potato, tea, tomato, tobacco, watermelon, and wheat host cell.

In another specific embodiment, the host cell is a murine cell.

In another specific embodiment, the host cell is a human cell.

Host cell transformation is well known in the art and may be achieved by a variety of methods including but not limited to electroporation, viral infection, plasmid/vector transfection, non-viral vector mediated transfection, *Agrobacterium*-mediated transformation, particle bombardment, and the like. Expression of desired gene products involves culturing the transformed host cells under suitable conditions and inducing expression of the transformed gene. Culture conditions and gene expression protocols in prokaryotic and eukaryotic cells are well known in the art (see General Methods section of Examples). Cells may be harvested and the gene products isolated according to protocols specific for the gene product.

In addition, a host cell may be chosen which modulates the expression of the inserted polynucleotide, or modifies and processes the polypeptide product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce a non-glycosylated core protein product. However, a polypeptide expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the polypeptide's activity. Furthermore, different vector/host expression systems may affect processing reactions, such as proteolytic cleavages, to a different extent.

Applicants' invention also relates to a non-human organism comprising an isolated host cell according to the invention. Preferably, the non-human organism is selected from the group consisting of a bacterium, a fungus, a yeast, a plant, an animal, and a mammal. More preferably, the non-human organism is a yeast, a plant, a mouse, a rat, a rabbit, a cat, a dog, a bovine, a goat, a pig, a horse, a sheep, a monkey, or a chimpanzee.

In a specific embodiment, the non-human organism is a yeast selected from the group consisting of *Saccharomyces, Pichia*, and *Candida*.

In another specific embodiment, the non-human organism is a plant selected from the group consisting of an apple, *Arabidopsis*, bajra, banana, barley, beans, beet, blackgram, chickpea, chili, cucumber, eggplant, favabean, maize, melon, millet, mungbean, oat, okra, *Panicum*, papaya, peanut, pea, pepper, pigeonpea, pineapple, *Phaseolus*, potato, pumpkin, rice, *sorghum*, soybean, squash, sugarcane, sugarbeet, sunflower, sweet potato, tea, tomato, tobacco, watermelon, and wheat.

In another specific embodiment, the non-human organism is a *Mus musculus* mouse.

Measuring Gene Expression/Transcription

One useful measurement of Applicants' methods of the invention is that of the transcriptional state of the cell including the identities and abundances of RNA, preferably mRNA species. Such measurements are conveniently conducted by measuring cDNA abundances by any of several existing gene expression technologies.

Nucleic acid array technology is a useful technique for determining differential mRNA expression. Such technology includes, for example, oligonucleotide chips and DNA microarrays. These techniques rely on DNA fragments or oligonucleotides which correspond to different genes or cDNAs which are immobilized on a solid support and hybridized to probes prepared from total mRNA pools extracted from cells, tissues, or whole organisms and converted to cDNA. Oligonucleotide chips are arrays of oligonucleotides synthesized on a substrate using photolithographic techniques. Chips have been produced which can analyze for up to 1700 genes. DNA microarrays are arrays of DNA samples, typically PCR products, that are robotically printed onto a microscope slide. Each gene is analyzed by a full or partial length target DNA sequence. Micro arrays with up to 10,000 genes are now routinely prepared commercially. The primary difference between these two techniques is that oligonucleotide chips typically utilize 25-mer oligonucleotides which allow fractionation of short DNA molecules whereas the larger DNA targets of microarrays, approximately 1000 base pairs, may provide more sensitivity in fractionating complex DNA mixtures.

Another useful measurement of Applicants' methods of the invention is that of determining the translation state of the cell by measuring the abundances of the constituent protein species present in the cell using processes well known in the art.

Where identification of genes associated with various physiological functions is desired, an assay may be employed in which changes in such functions as cell growth, apoptosis, senescence, differentiation, adhesion, binding to a specific molecules, binding to another cell, cellular organization, organogenesis, intracellular transport, transport facilitation, energy conversion, metabolism, myogenesis, neurogenesis, and/or hematopoiesis is measured.

In addition, selectable marker or reporter gene expression may be used to measure gene expression modulation using Applicants' invention.

Other methods to detect the products of gene expression are well known in the art and include Southern blots (DNA detection), dot or slot blots (DNA, RNA), Northern blots (RNA), and RT-PCR (RNA) analyses. Although less preferred, labeled proteins can be used to detect a particular nucleic acid sequence to which it hybridizes.

In some cases it is necessary to amplify the amount of a nucleic acid sequence. This may be carried out using one or more of a number of suitable methods including, for example, polymerase chain reaction ("PCR"), ligase chain reaction ("LCR"), strand displacement amplification ("SDA"), transcription-based amplification, and the like. PCR is carried out in accordance with known techniques in which, for example, a nucleic acid sample is treated in the presence of a heat stable DNA polymerase, under hybridizing conditions, with one oligonucleotide primer for each strand of the specific sequence to be detected. An extension product of each primer that is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample may be analyzed as described above to assess whether the sequence or sequences to be detected are present.

The present invention may be better understood by reference to the following non-limiting Examples, which are provided as exemplary of the invention.

EXAMPLES

General Methods

Standard recombinant DNA and molecular cloning techniques used herein are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, Greene Publishing Assoc. and Wiley-Interscience (1987).

Methods for plant tissue culture, transformation, plant molecular biology, and plant, general molecular biology may be found in *Plant Tissue Culture Concepts and Laboratory Exercises* edited by R N Trigiano and D J Gray, $2^{nd}$ edition, 2000, CRC press, New York; *Agrobacterium Protocols* edited by K M A Gartland and M R Davey, 1995, Humana Press, Totowa, N.J.; *Methods in Plant Molecular Biology*, P. Maliga et al., 1995, Cold Spring Harbor Lab Press, New York; and *Molecular Cloning*, J. Sambrook et al., 1989, Cold Spring Harbor Lab Press, New York.

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of host cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences may be accomplished using the suite of programs available from the Genetics Computer Group Inc. (Wisconsin Package Version 9.0, Genetics Computer Group (GCG), Madison, Wis.). Where the GCG program "Pileup" is used the gap creation default value of 12, and the gap extension default value of 4 may be used. Where the CGC "Gap" or "Bestfit" programs is used the default gap creation penalty of 50 and the default gap extension penalty of 3 may be used. In any case where GCG program parameters are not prompted for, in these or any other GCG program, default values may be used.

The meaning of abbreviations is as follows: "h" means hour(s), "min" means minute(s), "sec" means second(s), "d" means day(s), "μl" means microliter(s), "ml" means milliliter(s), "L" means liter(s), "μM" means micromolar, "mM" means millimolar, "μg" means microgram(s), "mg" means milligram(s), "A" means adenine or adenosine, "T" means thymine or thymidine, "G" means guanine or guanosine, "C" means cytidine or cytosine, "x g" means times gravity, "nt" means nucleotide(s), "aa" means amino acid(s), "bp" means base pair(s), "kb" means kilobase(s), "k" means kilo, "μ" means micro, and "C" means degrees Celsius.

Example 1

Applicants' improved EcR-based inducible gene modulation system was developed for use in various applications including gene therapy, expression of proteins of interest in host cells, production of transgenic organisms, and cell-based assays. This Example describes the construction and evaluation of several gene expression cassettes for use in the EcR-based inducible gene expression system of the invention.

In various cellular backgrounds, including mammalian cells, insect ecdysone receptor (EcR) heterodimerizes with retinoid X receptor (RXR) and, upon binding of ligand, transactivates genes under the control of ecdysone response elements. Applicants constructed several EcR-based gene expression cassettes based on the spruce budworm *Choristoneura fumiferana* EcR ("CfEcR"; full length polynucleotide and amino acid sequences are set forth in SEQ ID NO: 49 and SEQ ID NO: 50, respectively), *C. fumiferana* ultraspiracle ("CfUSP"; full length polynucleotide and amino acid sequences are set forth in SEQ ID NO: 51 and SEQ ID NO: 52, respectively), and mouse *Mus musculus* RXRα (MmRXRα; full length polynucleotide and amino acid sequences are set forth in SEQ ID NO: 53 and SEQ ID NO: 54, respectively). The prepared receptor constructs comprise a ligand binding domain of EcR and of RXR or of USP; a DNA binding domain of GAL4 or of EcR; and an activation domain of VP16. The reporter constructs include a reporter gene, luciferase or LacZ, operably linked to a synthetic promoter construct that comprises either GAL4 or EcR/USP binding sites (response elements). Various combinations of these receptor and reporter constructs were cotransfected into CHO, NIH3T3, CV1 and 293 cells. Gene induction potential (magnitude of induction) and ligand specificity and sensitivity were examined using four different ligands: two steroidal ligands (ponasterone A and muristerone A) and two non-steroidal ligands (N-(2-ethyl-3-methoxybenzoyl)-N'-(3,5-dimethylbenzoyl)-N'-tert-butylhydrazine and N-(3,4-(1,2-ethylenedioxy)-2-methylbenzoyl)-N'-(3,5-dimethylbenzoyl)-N'-tert-butylhydrazine) in a dose-dependent induction of reporter gene expression in the transfected cells. Reporter gene expression activities were assayed at 24 hr or 48 hr after ligand addition.

Gene Expression Cassettes:

Ecdysone receptor-based, chemically inducible gene expression cassettes (switches) were constructed as followed, using standard cloning methods available in the art. The following is brief description of preparation and composition of each switch.

1.1—GAL4EcR/VP16RXR:

The D, E, and F domains from spruce budworm *Choristoneura fumiferana* EcR ("CfEcRDEF"; SEQ ID NO: 3) were fused to GAL4 DNA binding domain ("DNABD"; SEQ ID NO: 41) and placed under the control of an SV40e promoter (SEQ ID NO: 55). The DEF domains from mouse (*Mus musculus*) RXR ("MmRXRDEF"; SEQ ID NO: 22) were fused to the activation domain from VP16 ("VP16AD"; SEQ ID NO: 45) and placed under the control of an SV40e promoter (SEQ ID NO: 55). Five consensus GAL4 binding sites ("5XGAL4RE"; comprising 5, GAL4RE comprising SEQ ID NO: 47) were fused to a synthetic E1b minimal promoter (SEQ ID NO: 56) and placed upstream of the luciferase gene (SEQ ID NO: 57).

1.2—GAL4EcR/VP16USP:

This construct was prepared in the same way as in switch 1.1 above except MmRXRDEF was replaced with the D, E and F domains from spruce budworm USP ("CfUSPDEF"; SEQ ID NO: 58). The constructs used in this example are similar to those disclosed in U.S. Pat. No. 5,880,333 except that *Choristoneura fumiferana* USP rather than *Drosophila melanogaster* USP was utilized.

1.3—GAL4RXR/VP16CfEcR:

MmRXRDEF (SEQ ID NO: 22) was fused to a GAL4DNABD (SEQ ID NO: 41) and CfEcRCDEF (SEQ ID NO: 1) was fused to a VP16AD (SEQ ED NO: 45).

1.4—GAL4RXR/VP16DmEcR:

This construct was prepared in the same way as switch 1.3 except CfEcRCDEF was replaced with DmEcRCDEF (SEQ ID NO: 6).

1.5—GAL4USP/VP16CfEcR:

This construct was prepared in the same way as switch 1.3 except MmRXRDEF was replaced with CfUSPDEF (SEQ ID NO: 58).

1.6—GAL4RXRCfEcRVP16:

This construct was prepared so that both the GAL4 DNABD and the VP16AD were placed on the same molecule. GAL4DNABD (SEQ ID NO: 41) and VP16AD (SEQ ID NO: 45) were fused to CfEcRDEF (SEQ ID NO: 3) at N- and C-termini respectively. The fusion was placed under the control of an SV40e promoter (SEQ ID NO: 55).

1.7—VP16CfEcR:

This construct was prepared such that CfEcRCDEF (SEQ ID NO: 1) was fused to VP16AD (SEQ ID NO: 45) and placed under the control of an SV40e promoter (SEQ ID NO: 55). Six ecdysone response elements ("EcRE"; SEQ ID NO: 59) from the hsp27 gene were placed upstream of the promoter and a luciferase gene (SEQ ID NO: 57). This switch most probably uses endogenous RXR.

1.8—DmVgRXR:

This system was purchased from Invitrogen Corp., Carlsbad, Calif. It comprises a *Drosophila melanogaster* EcR ("DmEcR") with a modified DNABD fused to VP16AD and placed under the control of a CMV promoter (SEQ ID NO: 60). Full length MmRXR (SEQ ID NO: 53) was placed under the control of the RSV promoter (SEQ ID NO: 61). The reporter, pIND(SP1)LacZ, contains five copies of a modified ecdysone response element ("EcRE", E/GRE), three copies of an SP1 enhancer, and a minimal heat shock promoter, all of which were placed upstream to the LacZ reporter gene.

1.9—CfVgRXR:

This example was prepared in the same way as switch 1.8 except DinEcR was replaced with a truncated CfEcR comprising a partial A/B domain and the complete CDEF domains [SEQ ID NO: 62 (polynucleotide) and SEQ ID NO: 63 (polypeptide)].

1.10—CfVgRXRdel:

This example was prepared in the same way as switch 1.9 except MmRXR (SEQ ID NO: 53) was deleted.

Cell Lines:

Four cell lines: CHO, Chinese hamster *Cricetulus griseus* ovarian cell line; NIH3T3 (3T3) mouse *Mus musculus* cell line; 293 human *Homo sapiens* kidney cell line, and CV1 African green monkey kidney cell line were used in these experiments. Cells were maintained in their respective media and were subcultured when they reached 60% confluency. Standard methods for culture and maintenance of the cells were followed.

Transfections:

Several commercially available lipofactors as well as electroporation methods were evaluated and the best conditions for transfection of each cell line were developed. CHO, NIH3T3, 293 and CV1 cells were grown to 60% confluency. DNAs corresponding, to the various switch constructs outlined in Examples 1.1 through 1.10 were transfected into CHO cells, NIH3T3 cells, 293 cells, or CV1 cells as follows.

CHO Cells:

Cells were harvested when they reach 60-80% confluency and plated in 6- or 12- or 24-well plates at 250,000, 100,000, or 50,000 cells in 2.5, 1.0, or 0.5 ml of growth medium containing 10% Fetal bovine serum respectively. The next day, the cells were rinsed with growth medium and transfected for four hours. LipofectAMINE™ 2000 (Life Technologies Inc,) was found to be the best transfection reagent for these cells. For 12-well plates, 4 µl of LipofectAMINE™ 2000 was mixed with 100 µl of growth medium. 1.0 µg of reporter construct and 0.25 µg of receptor construct(s) were added to the transfection mix. A second reporter construct was added [pTKRL (Promega), 0.1 µg/transfection mix] and comprised a *Renilla* luciferase gene (SEQ ID NO: 64) operably linked and placed under the control of a thymidine kinase (TK) constitutive promoter and was used for normalization. The contents of the transfection mix were mixed in a vortex mixer and let stand at room temperature for 30 min. At the end of incubation, the transfection mix was added to the cells maintained in 400 µl growth medium. The cells were maintained at 37° C. and 5% $CO_2$ for four hours. At the end of incubation, 500 µl of growth medium containing 20% FBS and either DMSO (control) or a DMSO solution of appropriate ligands were added and the cells were maintained at 37° C. and 5% $CO_2$ for 24-48 hr. The cells were harvested and reporter activity was assayed. The same procedure was followed for 6 and 24 well plates as well except all the reagents were doubled for 6 well plates and reduced to half for 24-well plates.

NIH3T3 Cells:

Superfect™ (Qiagen Inc.) was found to be the best transfection reagent for 3T3 cells. The same procedures described for CHO cells were followed for 3T3 cells as well with two modifications. The cells were plated when they reached 50% confluency. 125,000 or 50,000 or 25,000 cells were plated per well of 6- or 12- or 24-well plates respectively. The GAl4EcR/VP16RXR and reporter vector DNAs were transfected into NIH3T3 cells, the transfected cells were grown in medium containing PonA, MurA, N-(2-ethyl-3-methoxybenzoyl)-N'-(3,5-dimethylbenzoyl)-N'-t-butylhydrazine, or N-(3,4-(1,2-ethylenedioxy)-2-methylbenzoyl)-N'-(3,5-dimethylbenzoyl)-N'-tert-butylhydrazine for 48 hr. The ligand treatments were performed as described in the CHO cell section above.

293 Cells:

LipofectAMINE™ 2000 (Life Technologies) was found to be the best lipofactor for 293 cells. The same procedures described for CHO were followed for 293 cells except that the cells were plated in biocoated plates to avoid clumping. The ligand treatments were performed as described in the CHO cell section above.

CV1 Cells:

LipofectAMINE™ plus (Life Technologies) was found to be the best lipofactor for CV1 cells. The same procedures described for NIH3T3 cells were followed for CV1 cells Ligands:

Ponasterone A and Muristerone A were purchased from Sigma Chemical Company. The two non-steroids N-(2-ethyl-3-methoxybenzoyl)-N'-(3,5-dimethylbenzoyl)-N'-t-butylhydrazine, or N-(3,4-(1,2-ethylenedioxy)-2-methylbenzoyl)-N'-(3,5-dimethylbenzoyl)-N'-tert-butylhydrazine are synthetic stable ecdysteroids synthesized at Rohm and Haas Company. All ligands were dissolved in DMSO and the final concentration of DMSO was maintained at 0.1% in both controls and treatments.

Reporter Assays:

Cells were harvested 24-48 hr after adding ligands. 125, 250, or 500 µl of passive lysis buffer (part of Dual-luciferase™ reporter assay system from Promega Corporation) were added to each well of 24- or 12- or 24-well plates respectively. The plates were placed on a rotary shaker for 15 min. Twenty µl of lysate was assayed. Luciferase activity was measured using Dual-luciferase™ reporter assay system from Promega Corporation following the manufacturer's instructions. β-Galactosidase was measured using Galacto-Star™ assay kit from TROPIX following the manufacturer's instructions. All luciferase and β-galactosidase activities were normalized using *Renilla* luciferase as a standard. Fold activities were calculated by dividing normalized relative light units ("RLU") in ligand treated cells with normalized RLU in DMSO treated cells (untreated control).

The results of these experiments are provided in the following tables.

TABLE 1

Transactivation of reporter genes through various switches in CHO cells

| Composition of Switch | Mean Fold Activation with 50 µM N-(2-ethyl-3-methoxybenzoyl)-N'-(3,5-dimethylbenzoyl)-N'-t-butylhydrazine |
|---|---|
| 1.1 GAL4EcR + VP16RXR pGAL4RELuc | 267 |
| 1.2 GAL4EcR + VP16USP pGAL4RELuc | 2 |
| 1.3 GAL4RXR + VP16CfEcR pGAL4RELuc | 85 |
| 1.4 GAL4RXR + VP16DmEcR pGAL4RELuc | 312 |
| 1.5 GAL4USP + VP16CfEcR pGAL4RELuc | 2 |
| 1.6 GAL4CfEcRVP16 pGAL4RELuc | 9 |
| 1.7 VP16CfEcR pEcRELuc | 36 |
| 1.8 DmVgRXR + MmRXR pIND(SP1)LacZ | 14 |
| 1.9 CfVgRXR + MmRXR pIND(SP1)LacZ | 27 |
| 1.10 CfVgRXR pIND(SP1)LacZ | 29 |

TABLE 2

Transactivation of reporter genes through various switches in 3T3 cells

| Composition of Switch | Mean Fold Activation Through N-(2-ethyl-3-methoxybenzoyl)-N'-(3,5-dimethylbenzoyl)-N'-t-butylhydrazine |
|---|---|
| 1.1 GAL4EcR + VP16RXR pGAL4RELuc | 1118 |
| 1.2 GAL4EcR + VP16USP pGAL4RELuc | 2 |
| 1.3 GAL4RXR + VP16CfEcR pGAL4RELuc | 47 |
| 1.4 GAL4RXR + VP16DmEcR pGAL4RELuc | 269 |
| 1.5 GAL4USP + VP16CfEcR pGAL4RELuc | 3 |
| 1.6 GAL4CfEcRVP16 pGAL4RELuc | 7 |
| 1.7 VP16CfEcR pEcRELuc | 1 |
| 1.8 DmVgRXR + MmRXR pIND(SP1)LacZ | 21 |
| 1.9 CfVgRXR + MmRXR pIND(SP1)LacZ | 19 |
| 1.10 CfVgRXR pIND(SP1)LacZ | 2 |

TABLE 3

Transactivation of reporter genes through various switches in 293 cells

| Composition of Switch | Mean Fold Activation Through N-(2-ethyl-3-methoxybenzoyl)-N'-(3,5-dimethylbenzoyl)-N'-t-butylhydrazine |
|---|---|
| 1.1 GAL4EcR + VP16RXR pGAL4RELuc | 125 |
| 1.2 GAL4EcR + VP16USP pGAL4RELuc | 2 |
| 1.3 GAL4RXR + VP16CfEcR pGAL4RELuc | 17 |
| 1.4 GAL4RXR + VP16DmEcR pGAL4RELuc | 3 |
| 1.5 GAL4USP + VP16CfEcR pGAL4RELuc | 2 |
| 1.6 GAL4CfEcRVP16 pGAL4RELuc | 3 |
| 1.7 VP16CfEcR pEcRELuc | 2 |

TABLE 3-continued

Transactivation of reporter genes through various switches in 293 cells

| Composition of Switch | Mean Fold Activation Through N-(2-ethyl-3-methoxybenzoyl)-N'-(3,5-dimethylbenzoyl)-N'-t-butylhydrazine |
|---|---|
| 1.8 DmVgRXR + MmRXR pIND(SP1)LacZ | 21 |
| 1.9 CfVgRXR + MmRXR pIND(SP1)LacZ | 12 |
| 1.10 CfVgRXR pIND(SP1)LacZ | 3 |

TABLE 4

Transactivation of reporter genes through various switches in CV1 cells

| Composition of Switch | Mean Fold Activation Through N-(2-ethyl-3-methoxybenzoyl)-N'-(3,5-dimethylbenzoyl)-N'-t-butylhydrazine |
|---|---|
| 1.1 GAL4EcR + VP16RXR pGAL4RELuc | 279 |
| 1.2 GAL4EcR + VP16USP pGAL4RELuc | 2 |
| 1.3 GAL4RXR + VP16CfEcR pGAL4RELuc | 25 |
| 1.4 GAL4RXR + VP16DmEcR pGAL4RELuc | 80 |
| 1.5 GAL4USP + VP16CfEcR pGAL4RELuc | 3 |
| 1.6 GAL4CfEcRVP16 pGAL4RELuc | 6 |
| 1.7 VP16CfEcR pEcRELuc | 1 |
| 1.8 DmVgRXR + MmRXR pIND(SP1)LacZ | 12 |
| 1.9 CfVgRXR + MmRXR pIND(SP1)LacZ | 7 |
| 1.10 CfVgRXR pIND(SP1)LacZ | 1 |

TABLE 5

Transactivation of reporter gene GAL4CfEcRDEF/VP16MmRXRDEF (switch 1.1) through steroids and non-steroids in 3T3 cells.

| Ligand | Mean Fold Induction at 1.0 µM Concentration |
|---|---|
| 1. Ponasterone A | 1.0 |
| 2. Muristerone A | 1.0 |
| 3. N-(2-ethyl-3-methoxybenzoyl)-N'-(3,5-dimethylbenzoyl)-N'-tert-butylhydrazine | 116 |
| 4. N'-(3,4-(1,2-ethylenedioxy)-2-methylbenzoyl)-N'-(3,5-dimethylbenzoyl)-N'-tert-butylhydrazine | 601 |

TABLE 6

Transactivation of reporter gene GAL4MmRXRDEF/VP16CfEcRCDEF (switch 1.3) through steroids and non-steroids in 3T3 cells.

| Ligand | Mean Fold Induction at 1.0 µM Concentration |
|---|---|
| 1. Ponasterone A | 1.0 |
| 2. Muristerone A | 1.0 |
| 3. N-(2-ethyl-3-methoxybenzoyl)-N'-(3,5-dimethylbenzoyl)-N'-tert-butylhydrazine | 71 |
| 4. N'-(3,4-(1,2-ethylenedioxy)-2-methylbenzoyl)-N'-(3,5-dimethylbenzoyl)-N'-tert-butylhydrazine | 54 |

Applicants' results demonstrate that the non-steroidal ecdysone agonists, N-(2-ethyl-3-methoxybenzoyl)-N'-(3,5-dimethylbenzoyl)-N'-tert-butylhydrazine and N'-(3,4-(1,2-ethylenedioxy)-2-methylbenzoyl)-N'-(3,5-dimethylbenzoyl)-N'-tert-butylhydrazine, were more potent activators of CfEcR as compared to *Drosophila melanogaster* EcR (DmEcR). (see Tables 1-4). Also, in the mammalian cell lines tested, MmRXR performed better than CfUSP as a heterodimeric partner for CfEcR. (see Tables 1-4). Additionally, Applicants' inducible gene expression modulation system performed better when exogenous MmRXR was used than when the system relied only on endogenous RXR levels (see Tables 1-4).

Applicants' results also show that in a CfEcR-based inducible gene expression system, the non-steroidal ecdysone agonists induced reporter gene expression at a lower concentration (i.e., increased ligand sensitivity) as compared to the steroid ligands, ponasterone A and muristerone A (see Tables 5 and 6).

Out of 10 EcR based gene switches tested, the GAL4EcR/VP16RXR switch (Switch 1.1) performed better than any other switch in all four cell lines examined and was more sensitive to non-steroids than steroids. The results also demonstrate that placing the activation domain (AD) and DNA binding domain (DNABD) on each of the two partners reduced background when compared to placing both AD and DNABD together on one of the two partners. Therefore, a switch format where the AD and DNABD are separated between two partners, works well for EcR-based gene switch applications.

In addition, the MmRXR/EcR-based switches performed better than CfUSP/EcR-based switches, which have a higher background activity than the MmRXR/EcR switches in the absence of ligand Finally, the GAL4EcR/VP16RXR switch (Switch 1.1) was more sensitive to non-steroid ligands than to the steroid ligands (see Tables 5 and 6). In particular, steroid ligands initiated transactivation at concentrations of 50 µM, whereas the non-steroid ligands initiated transactivation at less than 1 µM (submicromolar) concentration.

Example 2

This Example describes Applicants' further analysis of truncated EcR and RXR polypeptides in the improved EcP-based inducible gene expression system of the invention. To identify the best combination and length of two receptors that give a switch with a) maximum induction in the presence of ligand; b) minimum background in the absence of ligand; c) highly sensitive to ligand concentration; and d) minimum cross-talk among ligands and receptors, Applicants made and analyzed several truncation mutations of the CfEcR and MmRXR receptor polypeptides in NIH3T3 cells.

Briefly, polynucleotides encoding EcR or RXR receptors were truncated at the junctions of A/B, C, D, E and F domains and fused to either a GAL4 DNA binding domain encoding polynucleotide (SEQ ID NO: 41) for CfEcR, or a VP16 activation domain encoding polynucleotide (SEQ ID NO: 45) for MmRXR as described in Example 1. The resulting receptor truncation/fusion polypeptides were assayed in NIH3T3 cells. Plasmid pFRLUC (Stratagene) encoding a luciferase polypeptide was used as a reporter gene construct and pTKRL (Promega) encoding a *Renilla* luciferase polypeptide under the control of the constitutive TK promoter was used to normalize the transfections as described above. The analysis was performed in triplicates and mean luciferase counts were determined as described above.

Gene Expression Cassettes Encoding Truncated Ecdysone Receptor Polypeptides

Figure 11:
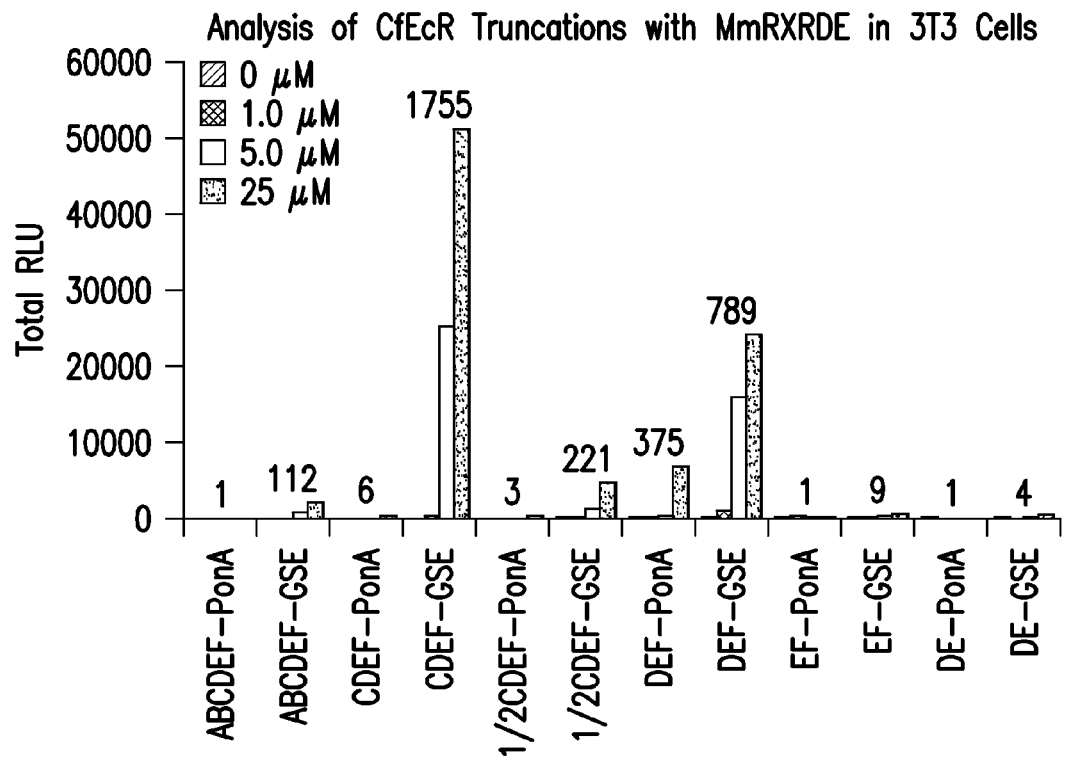
FIG. 11: Expression data of GAL4CfEcRA/BCDEF, GAL4CfEcRCDEF, GAL4CfEcR1/2CDEF, GAL4CfEcRDEF, GAL4CfEcREF, GAL4CfEcRDE truncation mutants transfected into NIH3T3 cells along with VP16MmRXRDE, pFRLUc and pTKRL plasmid DNAs.
Figure 12:
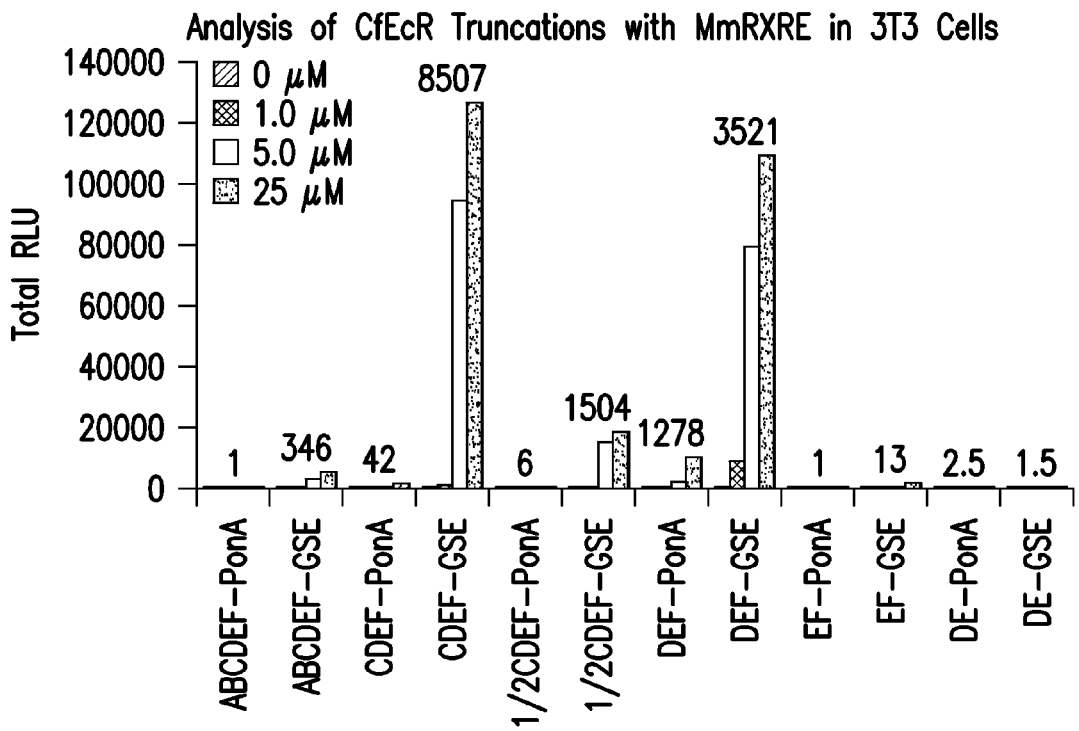
FIG. 12: Expression data of GAL4CfEcRA/BCDEF, GAL4CfEcRCDEF, GAL4CfEcR1/2CDEF, GAL4CfEcRDEF, GAL4CfEcREF, GAL4CfEcRDE truncation mutants transfected into 3T3 cells along with VP16MmRXRE, pFRLUc and pTKRL plasmid DNAs.

Gene expression cassettes comprising polynucleotides encoding either full length or truncated CfEcR polypeptides fused to a GAL4. DNA binding domain (SEQ ID NO: 41): GAL4CfEcRA/BCDEF (full length CfEcRA/BCDEF; SEQ ID NO: 49), GAL4CfEcRCDEF (CfEcRCDEF; SEQ ID NO: 1), GAL4CfEcR1/2CDEF (CfEcR1/2CDEF; SEQ ID NO: 2), GAL4CfEcRDEF (CfEcRDEF; SEQ ID NO: 3), GAL4CfEcREF (CfEcREF; SEQ ID NO: 4), and GAL4CfEcRDE (CfEcRDE; SEQ ID NO: 5) were transfected into NIH3T3 cells along with VP16MmRXRDEF (constructed as in Example 1.1; FIG. 11) or VP16MmRXREF [constructed as in Example 1.1 except that MmRXRDEF was replaced with MmRXREF (SEQ ID NO: 23); FIG. 12], and pFRLUc and pTKRL plasmid DNAs. The transfected cells were grown in the presence 0, 1, 5 or 25 uM of N-(2-ethyl-3-methoxybenzoyl)-N'-(3,5-dimethylbenzoyl)-N'-tert-butylhydrazine or PonA for 48 hr. The cells were harvested, lysed and luciferase reporter activity was measured in the cell lysates. Total fly luciferase relative light units are presented. The number on the top of each bar is the maximum fold induction for that treatment.

Applicants' results show that the EF domain of MmRXR is sufficient and performs better than DEF domains of this receptor (see FIGS. 11 and 12). Applicants have also shown that, in general, EcR/RXR receptor combinations are insensitive to PonA (see FIGS. 11 and 12). As shown in the FIGS. 11 and 12, the GAL4CfEcRCDEF hybrid polypeptide (SEQ ID NO: 7) performed better than any other CfEcR hybrid polypeptide.

Gene Expression Cassettes Encoding Truncated Retinoid X Receptor Polypeptides

Figure 13:
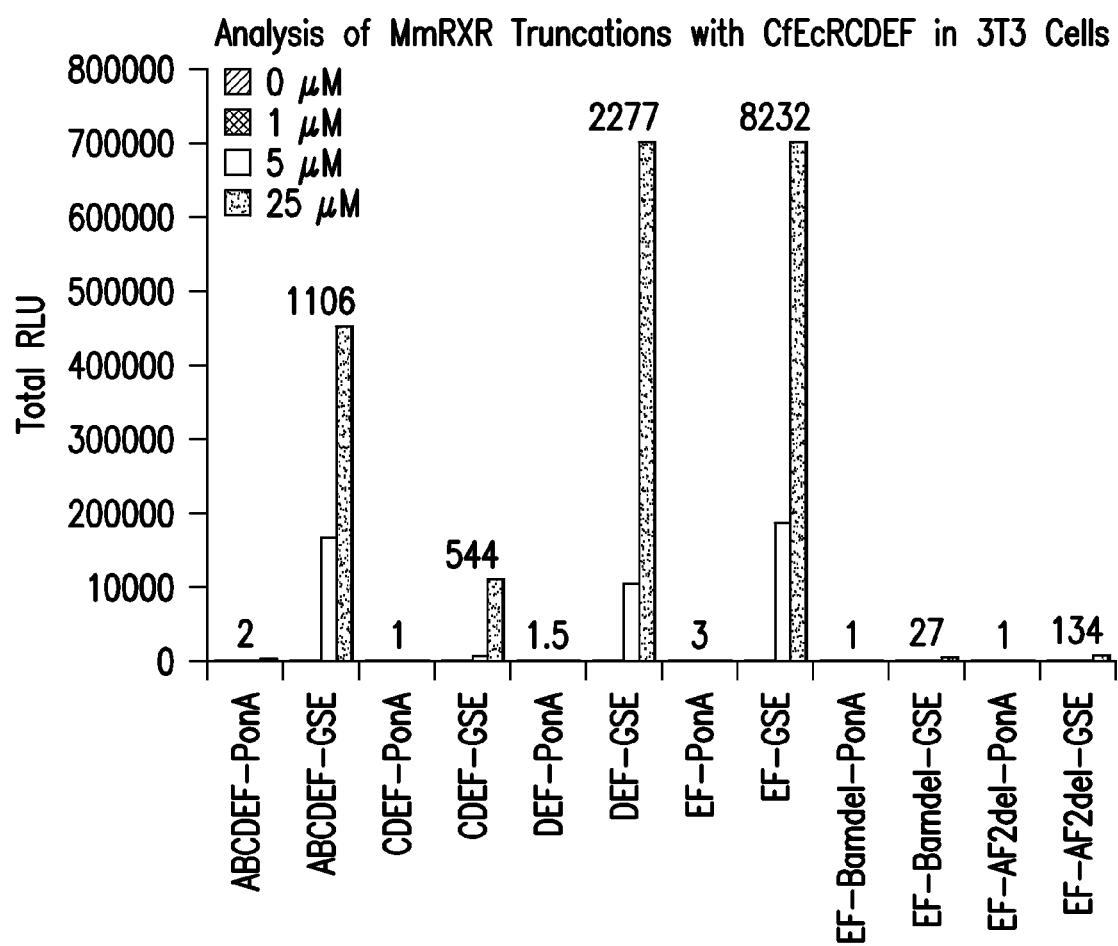
FIG. 13: Expression data of VP16MmRXRA/BCDEF, VP16MmRXRCDEF, VP16MmRXRDEF, VP16MmRXREF, VP16MmRXRBam-EF, VP16MmRXRAF2del constructs transfected into NIH3T3 cells along with GAL4CfEcRCDEF, pFRLUc and pTKRL plasmid DNAs.
Figure 14:
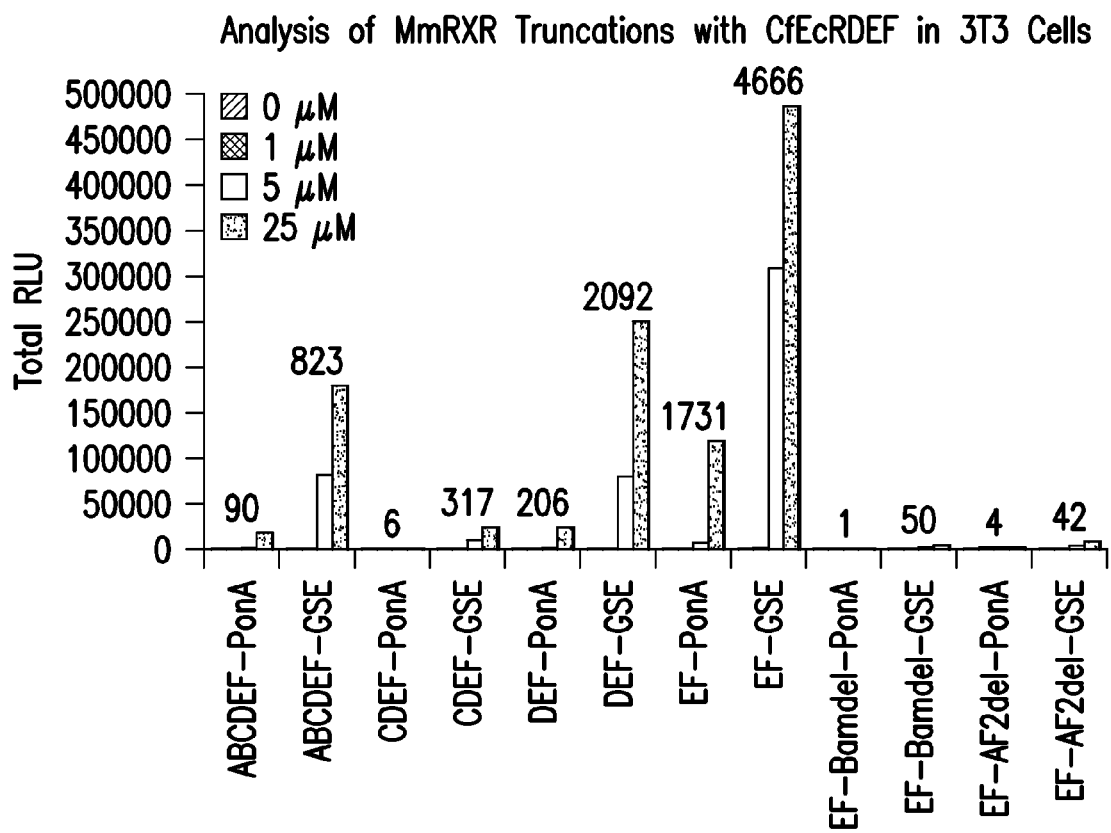
FIG. 14: Expression data of VP16MmRXRA/BCDEF, VP16MmRXRCDEF, VP16MmRXRDEF, VP16MmRXREF, VP16MmRXRBam-EF, VP16MmRXRAF2del constructs transfected into NIH3T3 cells along with GAL4CfEcRDEF, pFRLUc and pTKRL plasmid DNAs.

Gene expression cassettes comprising polynucleotides encoding either full length or truncated MmRXR polypeptides fused to a VP16 transactivation domain (SEQ ID NO: 45): VP16MmRXRA/BCDEF (full length MmRXRA/BCDEF; SEQ ID NO: 53), VP16MmRXRCDEF (MmRXRCDEF; SEQ ID NO: 21), VP16MmRXRDEF (MmRXRDEF; SEQ ID NO: 22). VP16MmRXREF (MmRXREF, SEQ ID NO: 23), VP16MmRXRBam-EF ("MmRXRBam-EF" or "MmRXR-truncatedEF"; SEQ ID NO: 24), and VP16MmRXRAF2del ("MmRXRAF2del" or "MmRXR-E"; SEQ ID NO: 25) constructs were transfected into NIH3T3 cells along with GAl4CfEcRCDEF (constructed as in Example 1.1; FIG. 13) or GAL4CfEcRDEF [constructed as in Example 1.1 except CfEcRCDEF was replaced with CfEcRDEF (SEQ ID NO: 3); FIG. 14], pFRLUc and pTKRL plasmid DNAs as described above. The transfected cells were grown in the presence 0, 1, 5 and 25 uM of N-(2-ethyl-3-methoxybenzoyl)-N'-(3,5-dimethylbenzoyl)-N'-tert-butylhydrazine or PonA for 48 hr. The cells were harvested and lysed and reporter activity was measured in the cell lysate. Total fly luciferase relative light units are presented. The number on top of each bar is the maximum fold induction in that treatment.

Of all the truncations of MmRXR tested, Applicants' results show that the MmRXREF receptor was the best partner for CfEcR (FIGS. 13 and 14). CfEcRCDEF showed better induction than CfEcRDEF using MmRXREF. Deleting AF2 (abbreviated "EF-AF2del") or helices 1-3 of the E domain (abbreviated "EF-Barndel") resulted in an RXR receptor that reduced gene induction and ligand sensitivity when partnered with either CfEcRCDEF (FIG. 13) or CfEcRDEF (FIG. 14) in NIH3T3 cells. In general, the CfEcR/RXR-based switch was much more sensitive to the non-steroid N-(2-ethyl-3-methoxybenzoyl)-N'-(3,5-dimethylbenzoyl)-N'-tert-butylhydrazine than to the steroid PonA.

Example 3

This Example describes Applicants' further analysis of gene expression cassettes encoding truncated EcR or RXR receptor polypeptides that affect either ligand binding activity or ligand sensitivity, or both. Briefly, six different combinations of chimeric receptor pairs, constructed as described in Examples 1 and 2, were further analyzed in a single experiment in NIH3T3 cells. These six receptor pair combinations and their corresponding sample numbers are depicted in Table 7.

TABLE 7

CfEcR + MmRXR Truncation Receptor Combinations in NIH3T3 Cells

Figure 15:
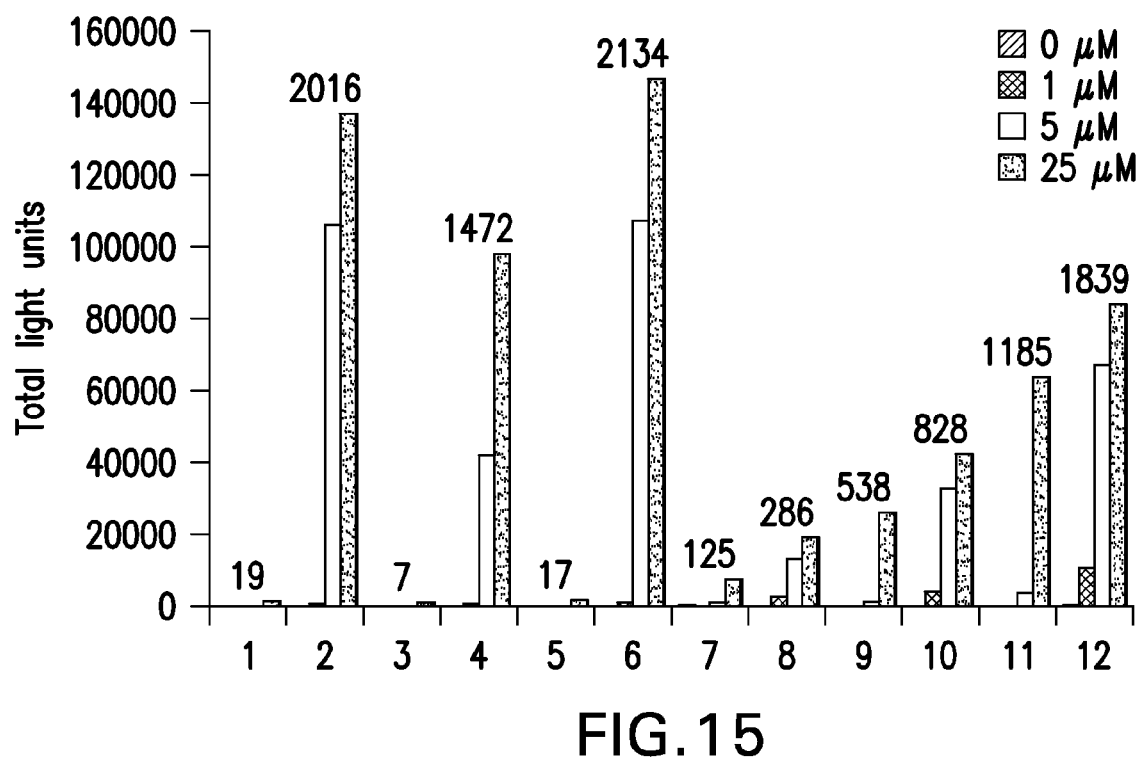
FIG. 15: Expression data of various truncated CfEcR and MmRXR receptor pairs transfected into NIH3T3 cells along with GAL4CfEcRDEF, pFRLUc and pTKRL plasmid DNAs.

| FIG. 15<br>X-Axis Sample No. | EcR Polypeptide<br>Construct | RXR Polypeptide<br>Construct |
|---|---|---|
| Samples 1 and 2 | GAL4CfEcRCDEF | VP16RXRA/BCDEF<br>(Full length) |
| Samples 3 and 4 | GAL4CfEcRCDEF | VP16RXRDEF |
| Samples 5 and 6 | GAL4CfEcRCDEF | VP16RXREF |
| Samples 7 and 8 | GAL4CfEcRDEF | VP16RXRA/BCDEF<br>(Full length) |
| Samples 9 and 10 | GAL4CfEcRDEF | VP16RXRDEF |
| Samples 11 and 12 | GAL4CfEcRDEF | VP16RXREF |

The above receptor construct pairs, along with the reporter plasmid pFRLuc were transfected into NIH3T3 cells as described above. The six CfEcR truncation receptor combinations were duplicated into two groups and treated with either steroid (odd numbers on x-axis of FIG. 15) or non-steroid (even numbers on x-axis of FIG. 15). In particular, the cells were grown in media containing 0, 1, 5 or 25 uM PonA (steroid) or N-(2-ethyl-3-methoxybenzoyl)-N'-(3,5-dimethylbenzoyl)-N'-tert-butylhydrazine (non-steroid) ligand. The reporter gene activity was measured and total RLU are shown. The number on top of each bar is the maximum fold induction for that treatment and is the mean of three replicates.

As shown in FIG. 15, the CfEcRCDEF/MmRXREF receptor combinations were the best switch pairs both in terms of total RLU and fold induction (compare columns 1-6 to columns 7-12). This confirms Applicants' earlier findings as described in Example 2 (FIGS. 11-14). The same gene expression cassettes encoding the truncated EcR and RXR polypeptides were also assayed in a human lung carcinoma cell line A549 (ATCC) and similar results were observed (data not shown).

We claim:

1. A transgenic, non-human animal whose genome comprises an ecdysone receptor-based gene expression modulation system comprising:
   (a) a first gene expression cassette that is capable of being expressed in a cell of said animal, said gene expression cassette comprising a polynucleotide sequence that encodes a first polypeptide comprising:
      (i) a DNA binding domain that recognizes a response element associated with a gene whose expression is to be modulated; and
      (ii) an ecdysone receptor ligand binding domain; and
   (b) a second gene expression cassette that is capable of being expressed in said animal, said gene expression cassette comprising a polynucleotide sequence that encodes a second polypeptide comprising:
      (i) a transactivation domain; and
      (ii) a retinoid X receptor ligand binding domain; and
   (c) a third gene expression cassette comprising;
      (i) a response element to which the DNA-binding domain binds;
      (iii) a promoter that is activated by the transactivation domain; and
      (viii) a gene whose expression is to be modulated;
   wherein the ligand binding domains from the first polypeptide and the second polypeptide are different and dimerize wherein at least one of the first polypeptide and the second polypeptide does not contain the A and B domains of the corresponding ecdysone receptor or retinoid X receptor,
   wherein the gene expression modulation system is more sensitive to a diacylhydrazine ligand than to a steroid ligand.

2. The transgenic, non-human animal of claim 1, wherein the diacylhydrazine ligand is a compound of the formula:

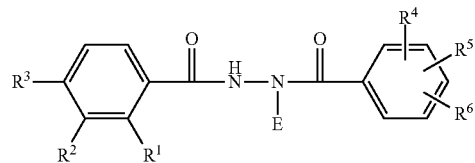

wherein:
E is a $(C_4-C_6)$alkyl containing a tertiary carbon or a cyano $(C_3-C_5)$alkyl containing a tertiary carbon;
$R^1$ is H, Me, Et, i-Pr, F, formyl, $CF_3$, $CHF_2$, $CHCl_2$, $CH_2F$, $CH_2Cl$, $CH_2OH$, $CH_2OMe$, $CH_2CN$, CN, C≡CH, 1-propynyl, 2-propynyl, vinyl, OH, OMe, OEt, cyclopropyl, $CF_2CF_3$, CH=CHCN, allyl, azido, SCN, or $SCHF_2$;

R² is H, Me, Et, n-Pr, i-Pr, formyl, CF₃, CHF₂, CHCl₂, CH₂F, CH₂Cl, CH₂OH, CH₂OMe, CH₂CN, CN, CCH, 1-propynyl, 2-propynyl, vinyl, Ac, F, Cl, OH, OMe, OEt, O-n-Pr, OAc, NMe₂, NEt₂, SMe, SEt, SOCF₃, OCF₂CF₂H, COEt, cyclopropyl, CF₂CF₃, CH=CHCN, allyl, azido, OCF₃, OCHF₂, O-i-Pr, SCN, SCHF₂, SOMe, NH—CN, or joined with R³ and the phenyl carbons to which R² and R³ are attached to form an ethylenedioxy, a dihydrofuryl ring with the oxygen adjacent to a phenyl carbon, or a dihydropyryl ring with the oxygen adjacent to a phenyl carbon;

R³ is H, Et, or joined with R² and the phenyl carbons to which R² and R³ are attached to form an ethylenedioxy, a dihydrofuryl ring with the oxygen adjacent to a phenyl carbon, or a dihydropyryl ring with the oxygen adjacent to a phenyl carbon;

R⁴, R⁵, and R⁶ are independently H, Me, Et, F, Cl, Br, formyl, CF₃, CHF₂, CHCl₂, CH₂F, CH₂Cl, CH₂OH, CN, CCH, 1-propynyl, 2-propynyl, vinyl, OMe, OEt, SMe, or SEt.

3. The transgenic, non-human animal organism of claim 1, wherein the ecdysone receptor ligand binding domain of the first polypeptide is encoded by a polynucleotide comprising a nucleic acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

4. The transgenic, non-human animal of claim 1, wherein the ecdysone receptor ligand binding domain of the first polypeptide comprises an amino acid sequence selected from the group consisting of SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:20.

5. The transgenic, non-human animal of claim 1, wherein the retinoic X receptor ligand binding domain of the second polypeptide is encoded by a polynucleotide comprising a nucleic acid sequence selected from the group consisting of SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, and SEQ ID NO:30.

6. The transgenic, non-human animal of claim 1, wherein the retinoic X receptor ligand binding domain of the second polypeptide comprises an amino acid sequence selected from the group consisting of SEQ ID NO:31, SEQ ID NO:32, SEQ ID NO:33, SEQ ID NO:34, SEQ ID NO:35, SEQ ID NO:36, SEQ ID NO37, SEQ ID NO:38, SEQ ID NO:39, and SEQ ID NO:40.

7. The transgenic, non-human animal of claim 1, wherein the ecdysone receptor ligand binding domain is selected from the group consisting of a Lepidopteran ecdysone receptor ligand binding domain, a Dipteran ecdysone receptor ligand binding domain, an Arthropod ecdysone receptor ligand binding domain, a Homopteran ecdysone receptor ligand binding domain, a spruce budworm *Choristoneura fumiferana* ecdysone receptor ligand binding domain, a *Tenebrio molitor* ecdysone receptor ligand binding domain, a *Manduca sexta* ecdysone receptor ligand binding domain, a *Heliothies virescens* ecdysone receptor ligand binding domain, a silk moth *Bombyx mori* ecdysone receptor ligand binding domain, a fruit fly *Drosophila melanogaster* ecdysone receptor ligand binding domain, a mosquito *Aedes aegypti* ecdysone receptor ligand binding domain, a blowfly *Lucilia capitata* ecdysone receptor ligand binding domain, a Mediterranean fruit fly *Ceratitis capitata* ecdysone receptor ligand binding domain, a locust *Locusta migratoria* ecdysone receptor ligand binding domain, an aphid *Myzus persicae* ecdysone receptor ligand binding domain, a fiddler crab *Uca pugilator* ecdysone receptor ligand binding domain, and an ixodid tick *Amblyomma americanum* ecdysone receptor ligand binding domain.

8. The transgenic, non-human animal of claim 7, wherein the ecdysone receptor ligand binding domain is a *Choristoneura fumiferana* ecdysone receptor ligand binding domain.

9. The transgenic, non-human animal of claim 1, wherein the expression of the gene whose expression is to be modulated is tissue-specific expression.

10. The transgenic, non-human animal of claim 1, wherein said first polypeptide does not contain the A and B domains of the ecdysone receptor.

11. The transgenic, non-human animal of claim 1, wherein said second polypeptide does not contain the A and B domains of the retinoid X receptor.

12. The transgenic, non-human animal of claim 1, wherein said gene expression modulation system is more sensitive to a diacylhydrazine ligand than to a steroid ligand when expressed in a mammalian cell.

13. The transgenic, non-human animal of claim 1, wherein said DNA binding domain is selected from the group consisting of a GAL4 DNA binding domain, a LexA DNA binding domain, a transcription factor DNA binding domain, a steroid/thyroid hormone nuclear receptor superfamily member DNA binding domain and a bacterial LacZ DNA binding domain.

14. The transgenic, non-human animal of claim 1, wherein said transactivation domain is selected from the group consisting of a steroid/thyroid hormone nuclear receptor transactivation domain, a polyglutamine transactivation domain, a basic or acidic amino acid transactivation domain, a VP16 transactivation domain, a GAL4 transactivation domain, an NF-κB transactivation domain and a BP64 transactivation domain.

15. The transgenic, non-human animal of claim 1, wherein said retinoic X receptor ligand binding domain of the second polypeptide is selected from the group consisting of a mouse *Mus musculus* retinoic X receptor ligand binding domain, a human *Homo sapiens* retinoic X receptor ligand binding domain.

16. The transgenic, non-human animal of claim 1, wherein said retinoic X receptor ligand binding domain of the second polypeptide is selected from the group consisting of an RXRα ligand binding domain, an RXRβ ligand binding domain and an RXRγ ligand binding domain.

17. The transgenic, non-human animal of claim 1, wherein said animal is a mammal.

18. The transgenic, non-human animal of claim 17, wherein said mammal is selected from the group consisting of a hamster, a mouse, a rat, a rabbit, a cat, a dog, a bovine, a goat, a cow, a pig, a horse, a sheep, a monkey, and a chimpanzee.

* * * * *

UNITED STATES PATENT AND TRADEMARK OFFICE
CERTIFICATE OF CORRECTION

PATENT NO. : 8,822,754 B2  
APPLICATION NO. : 13/463527  
DATED : September 2, 2014  
INVENTOR(S) : Palli et al.

Page 1 of 1

It is certified that error appears in the above-identified patent and that said Letters Patent is hereby corrected as shown below:

In the Claims

Column 143
Line 63, Claim 1, "(iii) a promoter" should be replaced with --(ii) a promoter--.

Column 143
Line 65, Claim 1, "(viii) a gene" should be replaced with --(iii) a gene--.

Column 145
Line 2, Claim 2, "CN, CCH," should be replaced with --CN, C≡CH,--.

Column 145
Line 19, Claim 2, "CN, CCH," should be replaced with --CN, C≡CH,--.

Signed and Sealed this  
Nineteenth Day of May, 2015

Michelle K. Lee  
*Director of the United States Patent and Trademark Office*

SEQUENCE LISTING

<160> NUMBER OF SEQ ID NOS: 64

<210> SEQ ID NO 1
<211> LENGTH: 1288
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 1

```
aagggccctg cgccccgtca gcaagaggaa ctgtgtctgg tatgcgggga cagagcctcc      60
ggataccact acaatgcgct cacgtgtgaa gggtgtaaag ggttcttcag acggagtgtt     120
accaaaaatg cggtttatat ttgtaaattc ggtcacgctt gcgaaatgga catgtacatg     180
cgacggaaat gccaggagtg ccgcctgaag aagtgcttag ctgtaggcat gaggcctgag     240
tgcgtagtac ccgagactca gtgcgccatg aagcggaaag agaagaaagc acagaaggag     300
aaggacaaac tgcctgtcag cacgacgacg gtggacgacc acatgccgcc cattatgcag     360
tgtgaacctc cacctcctga agcagcaagg attcacgaag tggtcccaag gtttctctcc     420
gacaagctgt tggagacaaa ccggcagaaa acatccccc agttgacagc caaccagcag     480
ttccttatcg ccaggctcat ctggtaccag gacgggtacg agcagccttc tgatgaagat     540
ttgaagagga ttacgcagac gtggcagcaa gcggacgatg aaaacgaaga gtctgacact     600
cccttccgcc agatcacaga gatgactatc ctcacggtcc aacttatcgt ggagttcgcg     660
aagggattgc cagggttcgc caagatctcg cagcctgatc aaattacgct gcttaaggct     720
tgctcaagtg aggtaatgat gctccgagtc gcgcgacgat acgatgcggc ctcagacagt     780
gttctgttcg cgaacaacca agcgtacact cgcgacaact accgcaaggc tggcatggcc     840
tacgtcatcg aggatctact gcacttctgc cggtgcatgt actctatggc gttggacaac     900
atccattacg cgctgctcac ggctgtcgtc atctttctg accggccagg gttggagcag     960
ccgcaactgg tggaagaaat ccagcggtac tacctgaata cgctccgcat ctatatcctg    1020
aaccagctga gcgggtcggc gcgttcgtcc gtcatatacg gcaagatcct ctcaatcctc    1080
tctgagctac gcacgctcgg catgcaaaac tccaacatgt gcatctccct caagctcaag    1140
aacagaaagc tgccgccttt cctcgaggag atctgggatg tggcggacat gtcgcacacc    1200
caaccgccgc ctatcctcga gtcccccacg aatctctagc ccctgcgcgc acgcatcgcc    1260
gatgccgcgt ccggccgcgc tgctctga                                      1288
```

<210> SEQ ID NO 2
<211> LENGTH: 1110
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 2

```
gcggtttata tttgtaaatt cggtcacgct tgcgaaatgg acatgtacat gcgacggaaa      60
tgccaggagt ccgcctgaa gaagtgctta gctgtaggca tgaggcctga gtgcgtagta     120
cccgagactc agtgcgccat gaagcggaaa gagaagaaag cacagaagga aggacaaa     180
ctgcctgtca gcacgacgac ggtggacgac cacatgccgc ccattatgca gtgtgaacct     240
ccacctcctg aagcagcaag gattcacgaa gtggtcccaa gtttctctc cgacaagctg     300
ttggagacaa accggcagaa aacatccccc cagttgacag ccaaccagca gttccttatc     360
```

-continued

```
gccaggctca tctggtacca ggacgggtac gagcagcctt ctgatgaaga tttgaagagg      420
attacgcaga cgtggcagca agcggacgat gaaaacgaag agtctgacac tcccttccgc      480
cagatcacag agatgactat cctcacggtc caacttatcg tggagttcgc gaagggattg      540
ccagggttcg ccaagatctc gcagcctgat caaattacgc tgcttaaggc ttgctcaagt      600
gaggtaatga tgctccgagt cgcgcgacga tacgatgcgg cctcagacag tgttctgttc      660
gcgaacaacc aagcgtacac tcgcgacaac taccgcaagg ctggcatggc ctacgtcatc      720
gaggatctac tgcacttctg ccggtgcatg tactctatgg cgttggacaa catccattac      780
gcgctgctca cggctgtcgt catctttttct gaccggccag ggttggagca gccgcaactg      840
gtggaagaaa tccagcggta ctacctgaat acgctccgca tctatatcct gaaccagctg      900
agcgggtcgg cgcgttcgtc cgtcatatac ggcaagatcc tctcaatcct ctctgagcta      960
cgcacgctcg gcatgcaaaa ctccaacatg tgcatctccc tcaagctcaa gaacagaaag     1020
ctgccgcctt tcctcgagga gatctgggat gtggcggaca tgtcgcacac ccaaccgccg     1080
cctatcctcg agtcccccac gaatctctag                                     1110
```

<210> SEQ ID NO 3
<211> LENGTH: 1054
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 3

```
cctgagtgcg tagtacccga gactcagtgc gccatgaagc ggaaagagaa gaaagcacag        60
aaggagaagg acaaactgcc tgtcagcacg acgacggtgg acgaccacat gccgcccatt       120
atgcagtgtg aacctccacc tcctgaagca gcaaggattc acgaagtggt cccaaggttt       180
ctctccgaca gctgttgga gacaaaccgg cagaaaaaca tcccccagtt gacagccaac        240
cagcagttcc ttatcgccag gctcatctgg taccaggacg ggtacgagca gccttctgat       300
gaagatttga gaggattac gcagacgtgg cagcaagcgg acgatgaaaa cgaagagtct       360
gacactccct tccgccagat cacagagatg actatcctca cggtccaact tatcgtggag       420
ttcgcgaagg gattgccagg gttcgccaag atctcgcagc ctgatcaaat tacgctgctt       480
aaggcttgct caagtgaggt aatgatgctc cgagtcgcgc gacgatacga tgcggcctca       540
gacagtgttc tgttcgcgaa caaccaagcg tacactcgcg acaactaccg caaggctggc       600
atggcctacg tcatcgagga tctactgcac ttctgccggt gcatgtactc tatggcgttg       660
gacaacatcc attacgcgct gctcacggct gtcgtcatct ttctgaccg gccagggttg       720
gagcagccgc aactggtgga agaaatccag cggtactacc tgaatacgct ccgcatctat       780
atcctgaacc agctgagcgg gtcggcgcgt tcgtccgtca tatacggcaa gatcctctca       840
atcctctctg agctacgcac gctcggcatg caaaactcca acatgtgcat ctcccctcaag       900
ctcaagaaca gaaagctgcc gcctttcctc gaggagatct gggatgtggc ggacatgtcg       960
cacacccaac cgccgcctat cctcgagtcc ccacgaatc tctagcccct gcgcgcacgc      1020
atcgccgatg ccgcgtccgg ccgcgctgct ctga                                 1054
```

<210> SEQ ID NO 4
<211> LENGTH: 735
<212> TYPE: DNA
<213> ORGANISM: Artificial Sequence

```
<220> FEATURE:
<221> NAME/KEY: misc_feature
<223> OTHER INFORMATION: Novel Sequence

<400> SEQUENCE: 4
taccaggacg ggtacgagca gccttctgat gaagatttga agaggattac gcagacgtgg      60
cagcaagcgg acgatgaaaa cgaagagtct gacactccct tccgccagat cacagagatg     120
actatcctca cggtccaact tatcgtggag ttcgcgaagg gattgccagg gttcgccaag     180
atctcgcagc ctgatcaaat tacgctgctt aaggcttgct caagtgaggt aatgatgctc     240
cgagtcgcgc gacgatacga tgcggcctca gacagtgttc tgttcgcgaa caaccaagcg     300
tacactcgcg acaactaccg caaggctggc atggcctacg tcatcgagga tctactgcac     360
ttctgccggt gcatgtactc tatggcgttg gacaacatcc attacgcgct gctcacggct     420
gtcgtcatct tttctgaccg gccagggttg gagcagccgc aactggtgga agaaatccag     480
cggtactacc tgaatacgct ccgcatctat atcctgaacc agctgagcgg gtcggcgcgt     540
tcgtccgtca tatacggcaa gatcctctca atcctctctg agctacgcac gctcggcatg     600
caaaactcca acatgtgcat ctccctcaag ctcaagaaca gaaagctgcc gcctttcctc     660
gaggagatct gggatgtggc ggacatgtcg cacacccaac cgccgcctat cctcgagtcc     720
cccacgaatc tctag                                                      735

<210> SEQ ID NO 5
<211> LENGTH: 960
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 5
cctgagtgcg tagtacccga gactcagtgc gccatgaagc ggaaagagaa gaaagcacag      60
aaggagaagg acaaactgcc tgtcagcacg acgacggtgg acgaccacat gccgcccatt     120
atgcagtgtg aacctccacc tcctgaagca gcaaggattc acgaagtggt cccaaggttt     180
ctctccgaca agctgttgga gacaaaccgg cagaaaaaca tccccagtt gacagccaac     240 cagcagttcc ttatcgccag gctcatctgg taccaggacg ggtacgagca gccttctgat     300
gaagatttga agaggattac gcagacgtgg cagcaagcgg acgatgaaaa cgaagagtct     360
gacactccct tccgccagat cacagagatg actatcctca cggtccaact tatcgtggag     420
ttcgcgaagg gattgccagg gttcgccaag atctcgcagc ctgatcaaat tacgctgctt     480
aaggcttgct caagtgaggt aatgatgctc cgagtcgcgc gacgatacga tgcggcctca     540
gacagtgttc tgttcgcgaa caaccaagcg tacactcgcg acaactaccg caaggctggc     600
atggcctacg tcatcgagga tctactgcac ttctgccggt gcatgtactc tatggcgttg     660
gacaacatcc attacgcgct gctcacggct gtcgtcatct tttctgaccg gccagggttg     720
gagcagccgc aactggtgga agaaatccag cggtactacc tgaatacgct ccgcatctat     780
atcctgaacc agctgagcgg gtcggcgcgt tcgtccgtca tatacggcaa gatcctctca     840
atcctctctg agctacgcac gctcggcatg caaaactcca acatgtgcat ctccctcaag     900
ctcaagaaca gaaagctgcc gcctttcctc gaggagatct gggatgtggc ggacatgtcg     960

<210> SEQ ID NO 6
<211> LENGTH: 1878
<212> TYPE: DNA
```

<213> ORGANISM: Artificial Sequence
<220> FEATURE:
<221> NAME/KEY: misc_feature
<223> OTHER INFORMATION: Novel Sequence

<400> SEQUENCE: 6

| | | | | | |
|---|---|---|---|---|---|
| ggacctgcgc | cacgggtgca | agaggagctg | tgcctggttt | gcggcgacag | ggcctccggc | 60 |
| taccactaca | acgccctcac | ctgtgagggc | tgcaaggggt | tctttcgacg | cagcgttacg | 120 |
| aagagcgccg | tctactgctg | caagttcggg | cgcgcctgcg | aaatggacat | gtacatgagg | 180 |
| cgaaagtgtc | aggagtgccg | cctgaaaaag | tgcctggccg | tgggtatgcg | gccggaatgc | 240 |
| gtcgtcccgg | agaaccaatg | tgcgatgaag | cggcgcgaaa | agaaggccca | gaaggagaag | 300 |
| gacaaaatga | ccacttcgcc | gagctctcag | catggcggca | atggcagctt | ggcctctggt | 360 |
| ggcggccaag | actttgttaa | gaaggagatt | cttgacctta | tgacatgcga | gccgccccag | 420 |
| catgccacta | ttccgctact | acctgatgaa | atattggcca | agtgtcaagc | gcgcaatata | 480 |
| ccttccttaa | cgtacaatca | gttggccgtt | atatacaagt | taatttggta | ccaggatggc | 540 |
| tatgagcagc | catctgaaga | ggatctcagg | cgtataatga | gtcaacccga | tgagaacgag | 600 |
| agccaaacgg | acgtcagctt | tcggcatata | accgagataa | ccatactcac | ggtccagttg | 660 |
| attgttgagt | ttgctaaagg | tctaccagcg | tttacaaaga | taccccagga | ggaccagatc | 720 |
| acgttactaa | aggcctgctc | gtcggaggtg | atgatgctgc | gtatggcacg | acgctatgac | 780 |
| cacagctcgg | actcaatatt | cttcgcgaat | aatagatcat | atacgcggga | ttcttacaaa | 840 |
| atggccggaa | tggctgataa | cattgaagac | ctgctgcatt | tctgccgcca | aatgttctcg | 900 |
| atgaaggtgg | acaacgtcga | atacgcgctt | ctcactgcca | ttgtgatctt | ctcggaccgg | 960 |
| ccgggcctgg | agaaggccca | actagtcgaa | gcgatccaga | gctactacat | cgacacgcta | 1020 |
| cgcatttata | tactcaaccg | ccactgcggc | gactcaatga | gcctcgtctt | ctacgcaaag | 1080 |
| ctgctctcga | tcctcaccga | gctgcgtacg | ctgggcaacc | agaacgccga | gatgtgtttc | 1140 |
| tcactaaagc | tcaaaaaccg | caaactgccc | aagttcctcg | aggagatctg | ggacgttcat | 1200 |
| gccatcccgc | catcggtcca | gtcgcacctt | cagattaccc | aggaggagaa | cgagcgtctc | 1260 |
| gagcgggctg | agcgtatgcg | ggcatcggtt | ggggcgcca | ttaccgccgg | cattgattgc | 1320 |
| gactctgcct | ccacttcggc | ggcggcagcc | gcggcccagc | atcagcctca | gcctcagccc | 1380 |
| cagccccaac | cctcctccct | gacccagaac | gattcccagc | accagacaca | gccgcagcta | 1440 |
| caacctcagc | taccacctca | gctgcaaggt | caactgcaac | cccagctcca | accacagctt | 1500 |
| cagacgcaac | tccagccaca | gattcaacca | cagccacagc | tccttcccgt | ctccgctccc | 1560 |
| gtgcccgcct | ccgtaaccgc | acctggttcc | ttgtccgcgg | tcagtacgag | cagcgaatac | 1620 |
| atgggcggaa | gtgcggccat | aggacccatc | acgccggcaa | ccaccagcag | tatcacggct | 1680 |
| gccgttaccg | ctagctccac | cacatcagcg | gtaccgatgg | caacggagt | tggagtcggt | 1740 |
| gttggggtgg | gcggcaacgt | cagcatgtat | gcgaacgccc | agacggcgat | ggccttgatg | 1800 |
| ggtgtagccc | tgcattcgca | ccaagagcag | cttatcgggg | gagtggcggt | taagtcggag | 1860 |
| cactcgacga | ctgcatag | | | | | 1878 |

<210> SEQ ID NO 7
<211> LENGTH: 1752
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 7

```
gccgtctact gctgcaagtt cgggcgcgcc tgcgaaatgg acatgtacat gaggcgaaag      60
tgtcaggagt gccgcctgaa aaagtgcctg gccgtgggta tgcggccgga atgcgtcgtc     120
ccggagaacc aatgtgcgat gaagcggcgc gaaaagaagg cccagaagga gaaggacaaa     180
atgaccactt cgccgagctc tcagcatggc ggcaatggca gcttggcctc tggtggcggc     240
caagactttg ttaagaagga gattcttgac cttatgacat gcgagccgcc ccagcatgcc     300
actattccgc tactacctga tgaaatattg gccaagtgtc aagcgcgcaa tataccttcc     360
ttaacgtaca atcagttggc cgttatatac aagttaattt ggtaccagga tggctatgag     420
cagccatctg aagaggatct caggcgtata atgagtcaac ccgatgagaa cgagagccaa     480
acggacgtca gctttcggca tataaccgag ataaccatac tcacggtcca gttgattgtt     540
gagtttgcta aggtctacc agcgtttaca agataccc aggaggacca gatcacgtta     600
ctaaaggcct gctcgtcgga ggtgatgatg ctgcgtatgg cacgacgcta tgaccacagc     660
tcggactcaa tattcttcgc gaataataga tcatatacgc gggattctta caaaatggcc     720
ggaatggctg ataacattga agacctgctg catttctgcc gccaaatgtt ctcgatgaag     780
gtggacaacg tcgaatacgc gcttctcact gccattgtga tcttctcgga ccggccgggc     840
ctggagaagg cccaactagt cgaagcgatc cagagctact acatcgacac gctacgcatt     900
tatatactca accgccactg cggcgactca atgagcctcg tcttctacgc aaagctgctc     960
tcgatcctca ccgagctgcg tacgctgggc aaccagaacg ccgagatgtg tttctcacta    1020
aagctcaaaa accgcaaact gcccaagttc ctcgaggaga tctgggacgt tcatgccatc    1080
ccgccatcgg tccagtcgca ccttcagatt acccaggagg agaacgagcg tctcgagcgg    1140
gctgagcgta tgcgggcatc ggttgggggc gccattaccg ccggcattga ttgcgactct    1200
gcctccactt cggcggcggc agccgcggcc cagcatcagc ctcagcctca gcccagccc     1260
caaccctcct ccctgaccca gaacgattcc cagcaccaga cacagccgca gctacaacct    1320
cagctaccac ctcagctgca aggtcaactg caaccccagc tccaaccaca gcttcagacg    1380
caactccagc cacagattca accacagcca cagctccttc ccgtctccgc tcccgtgccc    1440
gcctccgtaa ccgcacctgg ttccttgtcc gcggtcagta cgagcagcga atacatgggc    1500
ggaagtgcgg ccataggacc catcacgccg gcaaccacca gcagtatcac ggctgccgtt    1560
accgctagct ccaccacatc agcggtaccg atgggcaacg gagttggagt cggtgttggg    1620
gtgggcggca acgtcagcat gtatgcgaac gcccagacgg cgatggcctt gatgggtgta    1680
gccctgcatt cgcaccaaga gcagcttatc gggggagtgg cggttaagtc ggagcactcg    1740
acgactgcat ag                                                        1752
```

```
<210> SEQ ID NO 8
<211> LENGTH: 1650
<212> TYPE: DNA
<213> ORGANISM: Artificial Sequence
<220> FEATURE:
<221> NAME/KEY: misc_feature
<223> OTHER INFORMATION: Novel Sequence
```

<400> SEQUENCE: 8

```
cggccggaat gcgtcgtccc ggagaaccaa tgtgcgatga agcggcgcga aaagaaggcc      60
cagaaggaga aggacaaaat gaccacttcg ccgagctctc agcatggcgg caatggcagc     120
ttggcctctg gtggcggcca agactttgtt aagaaggaga ttcttgacct tatgacatgc     180
```
gagccgcccc agcatgccac tattccgcta ctacctgatg aaatattggc caagtgtcaa    240
gcgcgcaata taccttcctt aacgtacaat cagttggccg ttatatacaa gttaatttgg    300
taccaggatg gctatgagca gccatctgaa gaggatctca ggcgtataat gagtcaaccc    360
gatgagaaca gagccaaac ggacgtcagc tttcggcata taaccgagat aaccatactc    420
acggtccagt tgattgttga gtttgctaaa ggtctaccag cgtttacaaa gatacccag    480 gaggaccaga tcacgttact aaaggcctgc tcgtcggagg tgatgatgct gcgtatggca    540
cgacgctatg accacagctc ggactcaata ttcttcgcga ataatagatc atatacgcgg    600
gattcttaca aaatggccgg aatggctgat aacattgaag acctgctgca tttctgccgc    660
caaatgttct cgatgaaggt ggacaacgtc gaatacgcgc ttctcactgc cattgtgatc    720
ttctcggacc ggccgggcct ggagaaggcc caactagtcg aagcgatcca gagctactac    780
atcgacacgc tacgcattta tatactcaac cgccactgcg gcgactcaat gagcctcgtc    840
ttctacgcaa agctgctctc gatcctcacc gagctgcgta cgctgggcaa ccagaacgcc    900
gagatgtgtt tctcactaaa gctcaaaaac cgcaaactgc ccaagttcct cgaggagatc    960
tgggacgttc atgccatccc gccatcggtc cagtcgcacc ttcagattac ccaggaggag   1020
aacgagcgtc tcgagcgggc tgagcgtatg cgggcatcgg ttgggggcgc cattaccgcc   1080
ggcattgatt gcgactctgc ctccacttcg gcggcggcag ccgcggccca gcatcagcct   1140
cagcctcagc cccagcccca accctcctcc ctgacccaga acgattccca gcaccagaca   1200
cagccgcagc tacaacctca gctaccacct cagctgcaag gtcaactgca accccagctc   1260
caaccacagc ttcagacgca actccagcca cagattcaac cacagccaca gctccttccc   1320
gtctccgctc ccgtgcccgc ctccgtaacc gcacctggtt ccttgtccgc ggtcagtacg   1380
agcagcgaat acatgggcgg aagtgcggcc ataggaccca tcacgccggc aaccaccagc   1440
agtatcacgg ctgccgttac cgctagctcc accacatcag cggtaccgat gggcaacgga   1500
gttggagtcg gtgttggggt gggcggcaac gtcagcatgt atgcgaacgc ccagacggcg   1560
atggccttga tgggtgtagc cctgcattcg caccaagagc agcttatcgg gggagtggcg   1620
gttaagtcgg agcactcgac gactgcatag                                    1650

<210> SEQ ID NO 9
<211> LENGTH: 1338
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 9
tatgagcagc catctgaaga ggatctcagg cgtataatga gtcaacccga tgagaacgag     60
agccaaacgg acgtcagctt tcggcatata accgagataa ccatactcac ggtccagttg    120
attgttgagt ttgctaaagg tctaccagcg tttacaaaga tacccaggga ggaccagatc    180
acgttactaa aggcctgctc gtcggaggtg atgatgctgc gtatggcacg acgctatgac    240
cacagctcgg actcaatatt cttcgcgaat aatagatcat atacgcggga ttcttacaaa    300
atggccggaa tggctgataa cattgaagac ctgctgcatt tctgccgcca aatgttctcg    360
atgaaggtgg acaacgtcga atacgcgctt ctcactgcca ttgtgatctt ctcggaccgg    420
ccgggcctga gaaggcccaa ctagtcgaag cgatccagag ctactacatc gacacgcta    480 cgcatttata tactcaaccg ccactgcggc gactcaatga gcctcgtctt ctacgcaaag    540

```
ctgctctcga tcctcaccga gctgcgtacg ctgggcaacc agaacgccga gatgtgtttc    600
tcactaaagc tcaaaaaccg caaactgccc aagttcctcg aggagatctg ggacgttcat    660
gccatcccgc catcggtcca gtcgcacctt cagattaccc aggaggagaa cgagcgtctc    720
gagcgggctg agcgtatgcg ggcatcggtt gggggcgcca ttaccgccgg cattgattgc    780
gactctgcct ccacttcggc ggcggcagcc gcggcccagc atcagcctca gcctcagccc    840
cagccccaac cctcctccct gacccagaac gattcccagc accagacaca gccgcagcta    900
caacctcagc taccacctca gctgcaaggt caactgcaac cccagctcca accacagctt    960
cagacgcaac tccagccaca gattcaacca gcagcccacag tccttcccgt ctccgctccc   1020
gtgcccgcct ccgtaaccgc acctggttcc ttgtccgcgg tcagtacgag cagcgaatac   1080
atgggcggaa gtcggccat aggacccatc acgccgcaa ccaccagcag tatcacggct    1140
gccgttaccg ctagctccac cacatcagcg gtaccgatgg caacggagt tggagtcggt    1200 gttggggtgg gcggcaacgt cagcatgtat gcgaacgccc agacggcgat ggccttgatg   1260
ggtgtagccc tgcattcgca ccaagagcag cttatcgggg gagtggcggt taagtcggag   1320
cactcgacga ctgcatag                                                 1338
```

<210> SEQ ID NO 10
<211> LENGTH: 969
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 10

```
cggccggaat gcgtcgtccc ggagaaccaa tgtgcgatga agcggcgcga aaagaaggcc     60
cagaaggaga aggacaaaat gaccacttcg ccgagctctc agcatggcgg caatggcagc    120
ttggcctctg gtggcggcca agactttgtt aagaaggaga ttcttgacct tatgacatgc    180
gagccgcccc agcatgccac tattccgcta ctacctgatg aaatattggc caagtgtcaa    240
gcgcgcaata taccttcctt aacgtacaat cagttggccg ttatatacaa gttaatttgg    300
taccaggatg gctatgagca gccatctgaa gaggatctca ggcgtataat gagtcaaccc    360
gatgagaacg agagccaaac ggacgtcagc tttcggcata taaccgagat aaccatactc    420
acggtccagt tgattgttga gtttgctaaa ggtctaccag cgtttacaaa gatacccag    480 gaggaccaga tcacgttact aaaggcctgc tcgtcggagg tgatgatgct gcgtatggca    540
cgacgctatg accacagctc ggactcaata ttcttcgcga ataatagatc atatacgcgg    600
gattcttaca aaatggccgg aatggctgat aacattgaag acctgctgca tttctgccgc    660
caaatgttct cgatgaaggt ggacaacgtc gaatacgcgc ttctcactgc cattgtgatc    720
ttctcggacc ggccgggcct ggagaaggcc caactagtcg aagcgatcca gagctactac    780
atcgacacgc tacgcattta tatactcaac cgccactgcg cgactcaat gagcctcgtc    840 ttctacgcaa agctgctctc gatcctcacc gagctgcgta cgctgggcaa ccagaacgcc    900
gagatgtgtt tctcactaaa gctcaaaaac cgcaaactgc caagttcct cgaggagatc    960 tgggacgtt                                                            969
```

<210> SEQ ID NO 11
<211> LENGTH: 412
<212> TYPE: PRT
<213> ORGANISM: Artificial Sequence -continued

```
<220> FEATURE:
<221> NAME/KEY: misc_feature
<223> OTHER INFORMATION: Novel Sequence

<400> SEQUENCE: 11

Lys Gly Pro Ala Pro Arg Gln Gln Glu Glu Leu Cys Leu Val Cys Gly
1               5                   10                  15

Asp Arg Ala Ser Gly Tyr His Tyr Asn Ala Leu Thr Cys Glu Gly Cys
            20                  25                  30

Lys Gly Phe Phe Arg Arg Ser Val Thr Lys Asn Ala Val Tyr Ile Cys
        35                  40                  45

Lys Phe Gly His Ala Cys Glu Met Asp Met Tyr Met Arg Arg Lys Cys
50                  55                  60

Gln Glu Cys Arg Leu Lys Lys Cys Leu Ala Val Gly Met Arg Pro Glu
65                  70                  75                  80

Cys Val Val Pro Glu Thr Gln Cys Ala Met Lys Arg Lys Glu Lys Lys
                85                  90                  95

Ala Gln Lys Glu Lys Asp Lys Leu Pro Val Ser Thr Thr Thr Val Asp
            100                 105                 110

Asp His Met Pro Pro Ile Met Gln Cys Glu Pro Pro Pro Pro Glu Ala
        115                 120                 125

Ala Arg Ile His Glu Val Val Pro Arg Phe Leu Ser Asp Lys Leu Leu
    130                 135                 140

Glu Thr Asn Arg Gln Lys Asn Ile Pro Gln Leu Thr Ala Asn Gln Gln
145                 150                 155                 160

Phe Leu Ile Ala Arg Leu Ile Trp Tyr Gln Asp Gly Tyr Glu Gln Pro
                165                 170                 175

Ser Asp Glu Asp Leu Lys Arg Ile Thr Gln Thr Trp Gln Gln Ala Asp
            180                 185                 190

Asp Glu Asn Glu Glu Ser Asp Thr Pro Phe Arg Gln Ile Thr Glu Met
        195                 200                 205

Thr Ile Leu Thr Val Gln Leu Ile Val Glu Phe Ala Lys Gly Leu Pro
210                 215                 220

Gly Phe Ala Lys Ile Ser Gln Pro Asp Gln Ile Thr Leu Leu Lys Ala
225                 230                 235                 240

Cys Ser Ser Glu Val Met Met Leu Arg Val Ala Arg Arg Tyr Asp Ala
                245                 250                 255

Ala Ser Asp Ser Val Leu Phe Ala Asn Asn Gln Ala Tyr Thr Arg Asp
            260                 265                 270

Asn Tyr Arg Lys Ala Gly Met Ala Tyr Val Ile Glu Asp Leu Leu His
        275                 280                 285

Phe Cys Arg Cys Met Tyr Ser Met Ala Leu Asp Asn Ile His Tyr Ala
    290                 295                 300

Leu Leu Thr Ala Val Val Ile Phe Ser Asp Arg Pro Gly Leu Glu Gln
305                 310                 315                 320

Pro Gln Leu Val Glu Glu Ile Gln Arg Tyr Tyr Leu Asn Thr Leu Arg
                325                 330                 335

Ile Tyr Ile Leu Asn Gln Leu Ser Gly Ser Ala Arg Ser Ser Val Ile
            340                 345                 350

Tyr Gly Lys Ile Leu Ser Ile Leu Ser Glu Leu Arg Thr Leu Gly Met
        355                 360                 365

Gln Asn Ser Asn Met Cys Ile Ser Leu Lys Leu Lys Asn Arg Lys Leu
    370                 375                 380

Pro Pro Phe Leu Glu Glu Ile Trp Asp Val Ala Asp Met Ser His Thr
```

```
385                 390                 395                 400
Gln Pro Pro Pro Ile Leu Glu Ser Pro Thr Asn Leu
                405                 410
```

<210> SEQ ID NO 12
<211> LENGTH: 412
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 12

```
Lys Gly Pro Ala Pro Arg Gln Gln Glu Glu Leu Cys Leu Val Cys Gly
1               5                   10                  15

Asp Arg Ala Ser Gly Tyr His Tyr Asn Ala Leu Thr Cys Glu Gly Cys
            20                  25                  30

Lys Gly Phe Phe Arg Arg Ser Val Thr Lys Asn Ala Val Tyr Ile Cys
        35                  40                  45

Lys Phe Gly His Ala Cys Glu Met Asp Met Tyr Met Arg Arg Lys Cys
    50                  55                  60

Gln Glu Cys Arg Leu Lys Lys Cys Leu Ala Val Gly Met Arg Pro Glu
65                  70                  75                  80

Cys Val Val Pro Glu Thr Gln Cys Ala Met Lys Arg Lys Glu Lys Lys
                85                  90                  95

Ala Gln Lys Glu Lys Asp Lys Leu Pro Val Ser Thr Thr Thr Val Asp
            100                 105                 110

Asp His Met Pro Pro Ile Met Gln Cys Glu Pro Pro Pro Pro Glu Ala
        115                 120                 125

Ala Arg Ile His Glu Val Val Pro Arg Phe Leu Ser Asp Lys Leu Leu
    130                 135                 140

Glu Thr Asn Arg Gln Lys Asn Ile Pro Gln Leu Thr Ala Asn Gln Gln
145                 150                 155                 160

Phe Leu Ile Ala Arg Leu Ile Trp Tyr Gln Asp Gly Tyr Glu Gln Pro
                165                 170                 175

Ser Asp Glu Asp Leu Lys Arg Ile Thr Gln Thr Trp Gln Gln Ala Asp
            180                 185                 190

Asp Glu Asn Glu Glu Ser Asp Thr Pro Phe Arg Gln Ile Thr Glu Met
        195                 200                 205

Thr Ile Leu Thr Val Gln Leu Ile Val Glu Phe Ala Lys Gly Leu Pro
    210                 215                 220

Gly Phe Ala Lys Ile Ser Gln Pro Asp Gln Ile Thr Leu Leu Lys Ala
225                 230                 235                 240

Cys Ser Ser Glu Val Met Met Leu Arg Val Ala Arg Arg Tyr Asp Ala
                245                 250                 255

Ala Ser Asp Ser Val Leu Phe Ala Asn Asn Gln Ala Tyr Thr Arg Asp
            260                 265                 270

Asn Tyr Arg Lys Ala Gly Met Ala Tyr Val Ile Glu Asp Leu Leu His
        275                 280                 285

Phe Cys Arg Cys Met Tyr Ser Met Ala Leu Asp Asn Ile His Tyr Ala
    290                 295                 300

Leu Leu Thr Ala Val Val Ile Phe Ser Asp Arg Pro Gly Leu Glu Gln
305                 310                 315                 320

Pro Gln Leu Val Glu Glu Ile Gln Arg Tyr Tyr Leu Asn Thr Leu Arg
                325                 330                 335
```

```
Ile Tyr Ile Leu Asn Gln Leu Ser Gly Ser Ala Arg Ser Ser Val Ile
            340                 345                 350

Tyr Gly Lys Ile Leu Ser Ile Leu Ser Glu Leu Arg Thr Leu Gly Met
        355                 360                 365

Gln Asn Ser Asn Met Cys Ile Ser Leu Lys Leu Lys Asn Arg Lys Leu
370                 375                 380

Pro Pro Phe Leu Glu Glu Ile Trp Asp Val Ala Asp Met Ser His Thr
385                 390                 395                 400

Gln Pro Pro Pro Ile Leu Glu Ser Pro Thr Asn Leu
                405                 410

<210> SEQ ID NO 13
<211> LENGTH: 334
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 13

Pro Glu Cys Val Val Pro Glu Thr Gln Cys Ala Met Lys Arg Lys Glu
1               5                   10                  15

Lys Lys Ala Gln Lys Glu Lys Asp Lys Leu Pro Val Ser Thr Thr Thr
            20                  25                  30

Val Asp Asp His Met Pro Pro Ile Met Gln Cys Glu Pro Pro Pro Pro
        35                  40                  45

Glu Ala Ala Arg Ile His Glu Val Val Pro Arg Phe Leu Ser Asp Lys
    50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
            100                 105                 110

Ala Asp Asp Glu Asn Glu Glu Ser Asp Thr Pro Phe Arg Gln Ile Thr
        115                 120                 125

Glu Met Thr Ile Leu Thr Val Gln Leu Ile Val Glu Phe Ala Lys Gly
    130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
            180                 185                 190

Arg Asp Asn Tyr Arg Lys Ala Gly Met Ala Tyr Val Ile Glu Asp Leu
        195                 200                 205

Leu His Phe Cys Arg Cys Met Tyr Ser Met Ala Leu Asp Asn Ile His
    210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
            260                 265                 270

Val Ile Tyr Gly Lys Ile Leu Ser Ile Leu Ser Glu Leu Arg Thr Leu
        275                 280                 285
```

```
Gly Met Gln Asn Ser Asn Met Cys Ile Ser Leu Lys Leu Lys Asn Arg
        290                 295                 300

Lys Leu Pro Pro Phe Leu Glu Glu Ile Trp Asp Val Ala Asp Met Ser
305                 310                 315                 320

His Thr Gln Pro Pro Ile Leu Glu Ser Pro Thr Asn Leu
                325                 330
```

<210> SEQ ID NO 14
<211> LENGTH: 244
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 14

```
Tyr Gln Asp Gly Tyr Glu Gln Pro Ser Asp Glu Asp Leu Lys Arg Ile
1               5                   10                  15

Thr Gln Thr Trp Gln Gln Ala Asp Asp Glu Asn Glu Glu Ser Asp Thr
            20                  25                  30

Pro Phe Arg Gln Ile Thr Glu Met Thr Ile Leu Thr Val Gln Leu Ile
        35                  40                  45

Val Glu Phe Ala Lys Gly Leu Pro Gly Phe Ala Lys Ile Ser Gln Pro
50                  55                  60

Asp Gln Ile Thr Leu Leu Lys Ala Cys Ser Ser Glu Val Met Met Leu
65                  70                  75                  80

Arg Val Ala Arg Arg Tyr Asp Ala Ala Ser Asp Ser Val Leu Phe Ala
                85                  90                  95

Asn Asn Gln Ala Tyr Thr Arg Asp Asn Tyr Arg Lys Ala Gly Met Ala
            100                 105                 110

Tyr Val Ile Glu Asp Leu Leu His Phe Cys Arg Cys Met Tyr Ser Met
        115                 120                 125

Ala Leu Asp Asn Ile His Tyr Ala Leu Leu Thr Ala Val Val Ile Phe
    130                 135                 140

Ser Asp Arg Pro Gly Leu Glu Gln Pro Gln Leu Val Glu Glu Ile Gln
145                 150                 155                 160

Arg Tyr Tyr Leu Asn Thr Leu Arg Ile Tyr Ile Leu Asn Gln Leu Ser
                165                 170                 175

Gly Ser Ala Arg Ser Ser Val Ile Tyr Gly Lys Ile Leu Ser Ile Leu
            180                 185                 190

Ser Glu Leu Arg Thr Leu Gly Met Gln Asn Ser Asn Met Cys Ile Ser
        195                 200                 205

Leu Lys Leu Lys Asn Arg Lys Leu Pro Pro Phe Leu Glu Glu Ile Trp
    210                 215                 220

Asp Val Ala Asp Met Ser His Thr Gln Pro Pro Ile Leu Glu Ser
225                 230                 235                 240

Pro Thr Asn Leu
```

<210> SEQ ID NO 15
<211> LENGTH: 320
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 15

```
Pro Glu Cys Val Val Pro Glu Thr Gln Cys Ala Met Lys Arg Lys Glu
 1               5                  10                  15

Lys Lys Ala Gln Lys Gly Lys Asp Lys Leu Pro Val Ser Thr Thr Thr
                20                  25                  30

Val Asp Asp His Met Pro Pro Ile Met Gln Cys Glu Pro Pro Pro
             35                  40                  45

Glu Ala Ala Arg Ile His Glu Val Val Pro Arg Phe Leu Ser Asp Lys
        50                  55                  60

Leu Leu Glu Thr Asn Arg Gln Lys Asn Ile Pro Gln Leu Thr Ala Asn
65                  70                  75                  80

Gln Gln Phe Leu Ile Ala Arg Leu Ile Trp Tyr Gln Asp Gly Tyr Glu
                85                  90                  95

Gln Pro Ser Asp Glu Asp Leu Lys Arg Ile Thr Gln Thr Trp Gln Gln
                100                 105                 110

Ala Asp Asp Glu Asn Glu Glu Ser Asp Thr Pro Phe Arg Gln Ile Thr
                115                 120                 125

Glu Met Thr Ile Leu Thr Val Gln Leu Ile Val Glu Phe Ala Lys Gly
                130                 135                 140

Leu Pro Gly Phe Ala Lys Ile Ser Gln Pro Asp Gln Ile Thr Leu Leu
145                 150                 155                 160

Lys Ala Cys Ser Ser Glu Val Met Met Leu Arg Val Ala Arg Arg Tyr
                165                 170                 175

Asp Ala Ala Ser Asp Ser Val Leu Phe Ala Asn Asn Gln Ala Tyr Thr
                180                 185                 190

Arg Asp Asn Tyr Arg Lys Ala Gly Met Ala Tyr Val Ile Glu Asp Leu
                195                 200                 205

Leu His Phe Cys Arg Cys Met Tyr Ser Met Ala Leu Asp Asn Ile His
                210                 215                 220

Tyr Ala Leu Leu Thr Ala Val Val Ile Phe Ser Asp Arg Pro Gly Leu
225                 230                 235                 240

Glu Gln Pro Gln Leu Val Glu Glu Ile Gln Arg Tyr Tyr Leu Asn Thr
                245                 250                 255

Leu Arg Ile Tyr Ile Leu Asn Gln Leu Ser Gly Ser Ala Arg Ser Ser
                260                 265                 270

Val Ile Tyr Gly Lys Ile Leu Ser Ile Leu Ser Glu Leu Arg Thr Leu
                275                 280                 285

Gly Met Gln Asn Ser Asn Met Cys Ile Ser Leu Lys Leu Lys Asn Arg
                290                 295                 300

Lys Leu Pro Pro Phe Leu Glu Glu Ile Trp Asp Val Ala Asp Met Ser
305                 310                 315                 320

<210> SEQ ID NO 16
<211> LENGTH: 625
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 16

Gly Pro Ala Pro Arg Val Gln Glu Glu Leu Cys Leu Val Cys Gly Asp
 1               5                  10                  15

Arg Ala Ser Gly Tyr His Tyr Asn Ala Leu Thr Cys Glu Gly Cys Lys
                20                  25                  30

Gly Phe Phe Arg Arg Ser Val Thr Lys Ser Ala Val Tyr Cys Cys Lys
                35                  40                  45
```

```
Phe Gly Arg Ala Cys Glu Met Asp Met Tyr Met Arg Arg Lys Cys Gln
    50                  55                  60
Glu Cys Arg Leu Lys Lys Cys Leu Ala Val Gly Met Arg Pro Glu Cys
65                  70                  75                  80
Val Val Pro Glu Asn Gln Cys Ala Met Lys Arg Arg Glu Lys Lys Ala
                85                  90                  95
Gln Lys Glu Lys Asp Lys Met Thr Thr Ser Pro Ser Ser Gln His Gly
            100                 105                 110
Gly Asn Gly Ser Leu Ala Ser Gly Gly Gly Gln Asp Phe Val Lys Lys
        115                 120                 125
Glu Ile Leu Asp Leu Met Thr Cys Glu Pro Pro Gln His Ala Thr Ile
    130                 135                 140
Pro Leu Leu Pro Asp Glu Ile Leu Ala Lys Cys Gln Ala Arg Asn Ile
145                 150                 155                 160
Pro Ser Leu Thr Tyr Asn Gln Leu Ala Val Ile Tyr Lys Leu Ile Trp
                165                 170                 175
Tyr Gln Asp Gly Tyr Glu Gln Pro Ser Glu Glu Asp Leu Arg Arg Ile
            180                 185                 190
Met Ser Gln Pro Asp Glu Asn Glu Ser Gln Thr Asp Val Ser Phe Arg
    195                 200                 205
His Ile Thr Glu Ile Thr Ile Leu Thr Val Gln Leu Ile Val Glu Phe
210                 215                 220
Ala Lys Gly Leu Pro Ala Phe Thr Lys Ile Pro Gln Glu Asp Gln Ile
225                 230                 235                 240
Thr Leu Leu Lys Ala Cys Ser Ser Glu Val Met Met Leu Arg Met Ala
                245                 250                 255
Arg Arg Tyr Asp His Ser Ser Asp Ser Ile Phe Phe Ala Asn Asn Arg
            260                 265                 270
Ser Tyr Thr Arg Asp Ser Tyr Lys Met Ala Gly Met Ala Asp Asn Ile
        275                 280                 285
Glu Asp Leu Leu His Phe Cys Arg Gln Met Phe Ser Met Lys Val Asp
    290                 295                 300
Asn Val Glu Tyr Ala Leu Leu Thr Ala Ile Val Ile Phe Ser Asp Arg
305                 310                 315                 320
Pro Gly Leu Glu Lys Ala Gln Leu Val Glu Ala Ile Gln Ser Tyr Tyr
                325                 330                 335
Ile Asp Thr Leu Arg Ile Tyr Ile Leu Asn Arg His Cys Gly Asp Ser
            340                 345                 350
Met Ser Leu Val Phe Tyr Ala Lys Leu Leu Ser Ile Leu Thr Glu Leu
        355                 360                 365
Arg Thr Leu Gly Asn Gln Asn Ala Glu Met Cys Phe Ser Leu Lys Leu
    370                 375                 380
Lys Asn Arg Lys Leu Pro Lys Phe Leu Glu Glu Ile Trp Asp Val His
385                 390                 395                 400
Ala Ile Pro Pro Ser Val Gln Ser His Leu Gln Ile Thr Gln Glu Glu
                405                 410                 415
Asn Glu Arg Leu Glu Arg Ala Glu Arg Met Arg Ala Ser Val Gly Gly
            420                 425                 430
Ala Ile Thr Ala Gly Ile Asp Cys Asp Ser Ala Ser Thr Ser Ala Ala
        435                 440                 445
Ala Ala Ala Ala Gln His Gln Pro Gln Pro Gln Pro Gln Pro Gln Pro
    450                 455                 460
```

Ser Ser Leu Thr Gln Asn Asp Ser Gln His Gln Thr Gln Pro Gln Leu
465                 470                 475                 480

Gln Pro Gln Leu Pro Gln Leu Gln Gly Gln Leu Gln Pro Gln Leu
        485                 490                 495

Gln Pro Gln Leu Gln Thr Gln Leu Gln Pro Gln Ile Gln Pro Gln Pro
            500                 505                 510

Gln Leu Leu Pro Val Ser Ala Pro Val Pro Ala Ser Val Thr Ala Pro
        515                 520                 525

Gly Ser Leu Ser Ala Val Ser Thr Ser Ser Glu Tyr Met Gly Gly Ser
    530                 535                 540

Ala Ala Ile Gly Pro Ile Thr Pro Ala Thr Thr Ser Ser Ile Thr Ala
545                 550                 555                 560

Ala Val Thr Ala Ser Ser Thr Thr Ser Ala Val Pro Met Gly Asn Gly
                565                 570                 575

Val Gly Val Gly Val Gly Val Gly Gly Asn Val Ser Met Tyr Ala Asn
            580                 585                 590

Ala Gln Thr Ala Met Ala Leu Met Gly Val Ala Leu His Ser His Gln
        595                 600                 605

Glu Gln Leu Ile Gly Gly Val Ala Val Lys Ser Glu His Ser Thr Thr
    610                 615                 620

Ala
625

<210> SEQ ID NO 17
<211> LENGTH: 583
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 17

Ala Val Tyr Cys Cys Lys Phe Gly Arg Ala Cys Glu Met Asp Met Tyr
1               5                   10                  15

Met Arg Arg Lys Cys Gln Glu Cys Arg Leu Lys Lys Cys Leu Ala Val
            20                  25                  30

Gly Met Arg Pro Glu Cys Val Val Pro Glu Asn Gln Cys Ala Met Lys
        35                  40                  45

Arg Arg Glu Lys Lys Ala Gln Lys Glu Lys Asp Lys Met Thr Thr Ser
50                  55                  60

Pro Ser Ser Gln His Gly Gly Asn Gly Ser Leu Ala Ser Gly Gly Gly
65                  70                  75                  80

Gln Asp Phe Val Lys Lys Glu Ile Leu Asp Leu Met Thr Cys Glu Pro
                85                  90                  95

Pro Gln His Ala Thr Ile Pro Leu Leu Pro Asp Glu Ile Leu Ala Lys
            100                 105                 110

Cys Gln Ala Arg Asn Ile Pro Ser Leu Thr Tyr Asn Gln Leu Ala Val
        115                 120                 125

Ile Tyr Lys Leu Ile Trp Tyr Gln Asp Gly Tyr Glu Gln Pro Ser Glu
    130                 135                 140

Glu Asp Leu Arg Arg Ile Met Ser Gln Pro Asp Glu Asn Glu Ser Gln
145                 150                 155                 160

Thr Asp Val Ser Phe Arg His Ile Thr Glu Ile Thr Ile Leu Thr Val
                165                 170                 175

Gln Leu Ile Val Glu Phe Ala Lys Gly Leu Pro Ala Phe Thr Lys Ile
            180                 185                 190

Pro Gln Glu Asp Gln Ile Thr Leu Leu Lys Ala Cys Ser Ser Glu Val
            195                 200                 205

Met Met Leu Arg Met Ala Arg Arg Tyr Asp His Ser Ser Asp Ser Ile
210                 215                 220

Phe Phe Ala Asn Asn Arg Ser Tyr Thr Arg Asp Ser Tyr Lys Met Ala
225                 230                 235                 240

Gly Met Ala Asp Asn Ile Glu Asp Leu Leu His Phe Cys Arg Gln Met
                245                 250                 255

Phe Ser Met Lys Val Asp Asn Val Glu Tyr Ala Leu Leu Thr Ala Ile
                260                 265                 270

Val Ile Phe Ser Asp Arg Pro Gly Leu Glu Lys Ala Gln Leu Val Glu
            275                 280                 285

Ala Ile Gln Ser Tyr Tyr Ile Asp Thr Leu Arg Ile Tyr Ile Leu Asn
            290                 295                 300

Arg His Cys Gly Asp Ser Met Ser Leu Val Phe Tyr Ala Lys Leu Leu
305                 310                 315                 320

Ser Ile Leu Thr Glu Leu Arg Thr Leu Gly Asn Gln Asn Ala Glu Met
                325                 330                 335

Cys Phe Ser Leu Lys Leu Lys Asn Arg Lys Leu Pro Lys Phe Leu Glu
                340                 345                 350

Glu Ile Trp Asp Val His Ala Ile Pro Pro Ser Val Gln Ser His Leu
            355                 360                 365

Gln Ile Thr Gln Glu Glu Asn Glu Arg Leu Glu Arg Ala Glu Arg Met
            370                 375                 380

Arg Ala Ser Val Gly Gly Ala Ile Thr Ala Gly Ile Asp Cys Asp Ser
385                 390                 395                 400

Ala Ser Thr Ser Ala Ala Ala Ala Ala Gln His Gln Pro Gln Pro
                405                 410                 415

Gln Pro Gln Pro Gln Pro Ser Ser Leu Thr Gln Asn Asp Ser Gln His
            420                 425                 430

Gln Thr Gln Pro Gln Leu Gln Pro Gln Leu Pro Pro Gln Leu Gln Gly
            435                 440                 445

Gln Leu Gln Pro Gln Leu Gln Pro Gln Leu Gln Thr Gln Leu Gln Pro
450                 455                 460

Gln Ile Gln Pro Gln Pro Gln Leu Leu Pro Val Ser Ala Pro Val Pro
465                 470                 475                 480

Ala Ser Val Thr Ala Pro Gly Ser Leu Ser Ala Val Ser Thr Ser Ser
            485                 490                 495

Glu Tyr Met Gly Gly Ser Ala Ala Ile Gly Pro Ile Thr Pro Ala Thr
                500                 505                 510

Thr Ser Ser Ile Thr Ala Ala Val Thr Ala Ser Ser Thr Thr Ser Ala
            515                 520                 525

Val Pro Met Gly Asn Gly Val Gly Val Gly Val Gly Val Gly Gly Asn
530                 535                 540

Val Ser Met Tyr Ala Asn Ala Gln Thr Ala Met Ala Leu Met Gly Val
545                 550                 555                 560

Ala Leu His Ser His Gln Glu Gln Leu Ile Gly Gly Val Ala Val Lys
                565                 570                 575

Ser Glu His Ser Thr Thr Ala
            580

<210> SEQ ID NO 18
<211> LENGTH: 549

<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 18

| Arg | Pro | Glu | Cys | Val | Val | Pro | Glu | Asn | Gln | Cys | Ala | Met | Lys | Arg | Arg |
|---|---|---|---|---|---|---|---|---|---|---|---|---|---|---|---|
| 1 | | | | 5 | | | | | 10 | | | | | 15 | |

| Glu | Lys | Lys | Ala | Gln | Lys | Glu | Lys | Asp | Lys | Met | Thr | Thr | Ser | Pro | Ser |
|---|---|---|---|---|---|---|---|---|---|---|---|---|---|---|---|
| | | | 20 | | | | 25 | | | | | 30 | | | |

| Ser | Gln | His | Gly | Gly | Asn | Gly | Ser | Leu | Ala | Ser | Gly | Gly | Gly | Gln | Asp |
|---|---|---|---|---|---|---|---|---|---|---|---|---|---|---|---|
| | | 35 | | | | | 40 | | | | | 45 | | | |

| Phe | Val | Lys | Lys | Glu | Ile | Leu | Asp | Leu | Met | Thr | Cys | Glu | Pro | Pro | Gln |
|---|---|---|---|---|---|---|---|---|---|---|---|---|---|---|---|
| | 50 | | | | | 55 | | | | | 60 | | | | |

| His | Ala | Thr | Ile | Pro | Leu | Leu | Pro | Asp | Glu | Ile | Leu | Ala | Lys | Cys | Gln |
|---|---|---|---|---|---|---|---|---|---|---|---|---|---|---|---|
| 65 | | | | | 70 | | | | | 75 | | | | | 80 |

| Ala | Arg | Asn | Ile | Pro | Ser | Leu | Thr | Tyr | Asn | Gln | Leu | Ala | Val | Ile | Tyr |
|---|---|---|---|---|---|---|---|---|---|---|---|---|---|---|---|
| | | | | 85 | | | | | 90 | | | | | 95 | |

| Lys | Leu | Ile | Trp | Tyr | Gln | Asp | Gly | Tyr | Glu | Gln | Pro | Ser | Glu | Glu | Asp |
|---|---|---|---|---|---|---|---|---|---|---|---|---|---|---|---|
| | | | 100 | | | | | 105 | | | | | 110 | | |

| Leu | Arg | Arg | Ile | Met | Ser | Gln | Pro | Asp | Glu | Asn | Glu | Ser | Gln | Thr | Asp |
|---|---|---|---|---|---|---|---|---|---|---|---|---|---|---|---|
| | | 115 | | | | | 120 | | | | | 125 | | | |

| Val | Ser | Phe | Arg | His | Ile | Thr | Glu | Ile | Thr | Ile | Leu | Thr | Val | Gln | Leu |
|---|---|---|---|---|---|---|---|---|---|---|---|---|---|---|---|
| | 130 | | | | | 135 | | | | | 140 | | | | |

| Ile | Val | Glu | Phe | Ala | Lys | Gly | Leu | Pro | Ala | Phe | Thr | Lys | Ile | Pro | Gln |
|---|---|---|---|---|---|---|---|---|---|---|---|---|---|---|---|
| 145 | | | | | 150 | | | | | 155 | | | | | 160 |

| Glu | Asp | Gln | Ile | Thr | Leu | Leu | Lys | Ala | Cys | Ser | Ser | Glu | Val | Met | Met |
|---|---|---|---|---|---|---|---|---|---|---|---|---|---|---|---|
| | | | | 165 | | | | | 170 | | | | | 175 | |

| Leu | Arg | Met | Ala | Arg | Arg | Tyr | Asp | His | Ser | Ser | Asp | Ser | Ile | Phe | Phe |
|---|---|---|---|---|---|---|---|---|---|---|---|---|---|---|---|
| | | | 180 | | | | | 185 | | | | | 190 | | |

| Ala | Asn | Asn | Arg | Ser | Tyr | Thr | Arg | Asp | Ser | Tyr | Lys | Met | Ala | Gly | Met |
|---|---|---|---|---|---|---|---|---|---|---|---|---|---|---|---|
| | | 195 | | | | | 200 | | | | | 205 | | | |

| Ala | Asp | Asn | Ile | Glu | Asp | Leu | Leu | His | Phe | Cys | Arg | Gln | Met | Phe | Ser |
|---|---|---|---|---|---|---|---|---|---|---|---|---|---|---|---|
| 210 | | | | | 215 | | | | | 220 | | | | | |

| Met | Lys | Val | Asp | Asn | Val | Glu | Tyr | Ala | Leu | Leu | Thr | Ala | Ile | Val | Ile |
|---|---|---|---|---|---|---|---|---|---|---|---|---|---|---|---|
| 225 | | | | | 230 | | | | | 235 | | | | | 240 |

| Phe | Ser | Asp | Arg | Pro | Gly | Leu | Glu | Lys | Ala | Gln | Leu | Val | Glu | Ala | Ile |
|---|---|---|---|---|---|---|---|---|---|---|---|---|---|---|---|
| | | | 245 | | | | | 250 | | | | | 255 | | |

| Gln | Ser | Tyr | Tyr | Ile | Asp | Thr | Leu | Arg | Ile | Tyr | Ile | Leu | Asn | Arg | His |
|---|---|---|---|---|---|---|---|---|---|---|---|---|---|---|---|
| | | | 260 | | | | | 265 | | | | | 270 | | |

| Cys | Gly | Asp | Ser | Met | Ser | Leu | Val | Phe | Tyr | Ala | Lys | Leu | Leu | Ser | Ile |
|---|---|---|---|---|---|---|---|---|---|---|---|---|---|---|---|
| | | 275 | | | | | 280 | | | | | 285 | | | |

| Leu | Thr | Glu | Leu | Arg | Thr | Leu | Gly | Asn | Gln | Asn | Ala | Glu | Met | Cys | Phe |
|---|---|---|---|---|---|---|---|---|---|---|---|---|---|---|---|
| | 290 | | | | | 295 | | | | | 300 | | | | |

| Ser | Leu | Lys | Leu | Lys | Asn | Arg | Lys | Leu | Pro | Lys | Phe | Leu | Glu | Glu | Ile |
|---|---|---|---|---|---|---|---|---|---|---|---|---|---|---|---|
| 305 | | | | | 310 | | | | | 315 | | | | | 320 |

| Trp | Asp | Val | His | Ala | Ile | Pro | Pro | Ser | Val | Gln | Ser | His | Leu | Gln | Ile |
|---|---|---|---|---|---|---|---|---|---|---|---|---|---|---|---|
| | | | | 325 | | | | | 330 | | | | | 335 | |

| Thr | Gln | Glu | Glu | Asn | Glu | Arg | Leu | Glu | Arg | Ala | Glu | Arg | Met | Arg | Ala |
|---|---|---|---|---|---|---|---|---|---|---|---|---|---|---|---|
| | | | 340 | | | | | 345 | | | | | 350 | | |

| Ser | Val | Gly | Gly | Ala | Ile | Thr | Ala | Gly | Ile | Asp | Cys | Asp | Ser | Ala | Ser |
|---|---|---|---|---|---|---|---|---|---|---|---|---|---|---|---|
| | | 355 | | | | | 360 | | | | | 365 | | | |

| Thr | Ser | Ala | Ala | Ala | Ala | Ala | Gln | His | Gln | Pro | Gln | Pro | Gln | Pro |
|---|---|---|---|---|---|---|---|---|---|---|---|---|---|---|
| 370 | | | | | 375 | | | | | 380 | | | | |

-continued

```
Gln Pro Gln Pro Ser Ser Leu Thr Gln Asn Asp Ser Gln His Gln Thr
385                 390                 395                 400

Gln Pro Gln Leu Gln Pro Leu Pro Pro Gln Leu Gln Gly Gln Leu
            405                 410                 415

Gln Pro Gln Leu Gln Pro Gln Leu Gln Thr Gln Leu Gln Pro Gln Ile
            420                 425                 430

Gln Pro Gln Pro Gln Leu Leu Pro Val Ser Ala Pro Val Pro Ala Ser
            435                 440                 445

Val Thr Ala Pro Gly Ser Leu Ser Ala Val Ser Thr Ser Ser Glu Tyr
450                 455                 460

Met Gly Gly Ser Ala Ala Ile Gly Pro Ile Thr Pro Ala Thr Thr Ser
465                 470                 475                 480

Ser Ile Thr Ala Ala Val Thr Ala Ser Ser Thr Thr Ser Ala Val Pro
                485                 490                 495

Met Gly Asn Gly Val Gly Val Gly Val Gly Val Gly Gly Asn Val Ser
                500                 505                 510

Met Tyr Ala Asn Ala Gln Thr Ala Met Ala Leu Met Gly Val Ala Leu
            515                 520                 525

His Ser His Gln Glu Gln Leu Ile Gly Gly Val Ala Val Lys Ser Glu
            530                 535                 540

His Ser Thr Thr Ala
545

<210> SEQ ID NO 19
<211> LENGTH: 445
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 19

Tyr Glu Gln Pro Ser Glu Glu Asp Leu Arg Arg Ile Met Ser Gln Pro
1               5                   10                  15

Asp Glu Asn Glu Ser Gln Thr Asp Val Ser Phe Arg His Ile Thr Glu
                20                  25                  30

Ile Thr Ile Leu Thr Val Gln Leu Ile Val Glu Phe Ala Lys Gly Leu
            35                  40                  45

Pro Ala Phe Thr Lys Ile Pro Gln Glu Asp Gln Ile Thr Leu Leu Lys
        50                  55                  60

Ala Cys Ser Ser Glu Val Met Met Leu Arg Met Ala Arg Arg Tyr Asp
65                  70                  75                  80

His Ser Ser Asp Ser Ile Phe Phe Ala Asn Asn Arg Ser Tyr Thr Arg
                85                  90                  95

Asp Ser Tyr Lys Met Ala Gly Met Ala Asp Asn Ile Glu Asp Leu Leu
            100                 105                 110

His Phe Cys Arg Gln Met Phe Ser Met Lys Val Asp Asn Val Glu Tyr
        115                 120                 125

Ala Leu Leu Thr Ala Ile Val Ile Phe Ser Asp Arg Pro Gly Leu Glu
    130                 135                 140

Lys Ala Gln Leu Val Glu Ala Ile Gln Ser Tyr Tyr Ile Asp Thr Leu
145                 150                 155                 160

Arg Ile Tyr Ile Leu Asn Arg His Cys Gly Asp Ser Met Ser Leu Val
                165                 170                 175

Phe Tyr Ala Lys Leu Leu Ser Ile Leu Thr Glu Leu Arg Thr Leu Gly
```

```
                 180                 185                 190
Asn Gln Asn Ala Glu Met Cys Phe Ser Leu Lys Leu Lys Asn Arg Lys
            195                 200                 205

Leu Pro Lys Phe Leu Glu Glu Ile Trp Asp Val His Ala Ile Pro Pro
        210                 215                 220

Ser Val Gln Ser His Leu Gln Ile Thr Gln Glu Asn Glu Arg Leu
225                 230                 235                 240

Glu Arg Ala Glu Arg Met Arg Ala Ser Val Gly Gly Ala Ile Thr Ala
                245                 250                 255

Gly Ile Asp Cys Asp Ser Ala Ser Thr Ser Ala Ala Ala Ala Ala
            260                 265                 270

Gln His Gln Pro Gln Pro Gln Pro Gln Pro Ser Ser Leu Thr
        275                 280                 285

Gln Asn Asp Ser Gln His Gln Thr Gln Pro Gln Leu Gln Pro Gln Leu
            290                 295                 300

Pro Pro Gln Leu Gln Gly Gln Leu Gln Pro Gln Leu Gln Pro Gln Leu
305                 310                 315                 320

Gln Thr Gln Leu Gln Pro Gln Ile Gln Pro Gln Leu Leu Pro
                325                 330                 335

Val Ser Ala Pro Val Pro Ala Ser Val Thr Ala Pro Gly Ser Leu Ser
            340                 345                 350

Ala Val Ser Thr Ser Ser Glu Tyr Met Gly Gly Ser Ala Ala Ile Gly
            355                 360                 365

Pro Ile Thr Pro Ala Thr Thr Ser Ser Ile Thr Ala Ala Val Thr Ala
        370                 375                 380

Ser Ser Thr Thr Ser Ala Val Pro Met Gly Asn Gly Val Gly Val Gly
385                 390                 395                 400

Val Gly Val Gly Gly Asn Val Ser Met Tyr Ala Asn Ala Gln Thr Ala
                405                 410                 415

Met Ala Leu Met Gly Val Ala Leu His Ser His Gln Glu Gln Leu Ile
            420                 425                 430

Gly Gly Val Ala Val Lys Ser Glu His Ser Thr Thr Ala
        435                 440                 445

<210> SEQ ID NO 20
<211> LENGTH: 323
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 20

Arg Pro Glu Cys Val Val Pro Glu Asn Gln Cys Ala Met Lys Arg Arg
1               5                   10                  15

Glu Lys Lys Ala Gln Lys Glu Lys Asp Lys Met Thr Thr Ser Pro Ser
            20                  25                  30

Ser Gln His Gly Gly Asn Gly Ser Leu Ala Ser Gly Gly Gly Gln Asp
        35                  40                  45

Phe Val Lys Lys Glu Ile Leu Asp Leu Met Thr Cys Glu Pro Pro Gln
    50                  55                  60

His Ala Thr Ile Pro Leu Leu Pro Asp Glu Ile Leu Ala Lys Cys Gln
65                  70                  75                  80

Ala Arg Asn Ile Pro Ser Leu Thr Tyr Asn Gln Leu Ala Val Ile Tyr
                85                  90                  95
```

Lys Leu Ile Trp Tyr Gln Asp Gly Tyr Glu Gln Pro Ser Glu Asp
            100                 105                 110

Leu Arg Arg Ile Met Ser Gln Pro Asp Glu Asn Glu Ser Gln Thr Asp
        115                 120                 125

Val Ser Phe Arg His Ile Thr Glu Ile Thr Ile Leu Thr Val Gln Leu
130                 135                 140

Ile Val Glu Phe Ala Lys Gly Leu Pro Ala Phe Thr Lys Ile Pro Gln
145                 150                 155                 160

Glu Asp Gln Ile Thr Leu Leu Lys Ala Cys Ser Ser Glu Val Met Met
                165                 170                 175

Leu Arg Met Ala Arg Arg Tyr Asp His Ser Ser Asp Ser Ile Phe Phe
            180                 185                 190

Ala Asn Asn Arg Ser Tyr Thr Arg Asp Ser Tyr Lys Met Ala Gly Met
        195                 200                 205

Ala Asp Asn Ile Glu Asp Leu Leu His Phe Cys Arg Gln Met Phe Ser
210                 215                 220

Met Lys Val Asp Asn Val Glu Tyr Ala Leu Leu Thr Ala Ile Val Ile
225                 230                 235                 240

Phe Ser Asp Arg Pro Gly Leu Glu Lys Ala Gln Leu Val Glu Ala Ile
                245                 250                 255

Gln Ser Tyr Tyr Ile Asp Thr Leu Arg Ile Tyr Ile Leu Asn Arg His
            260                 265                 270

Cys Gly Asp Ser Met Ser Leu Val Phe Tyr Ala Lys Leu Leu Ser Ile
        275                 280                 285

Leu Thr Glu Leu Arg Thr Leu Gly Asn Gln Asn Ala Glu Met Cys Phe
290                 295                 300

Ser Leu Lys Leu Lys Asn Arg Lys Leu Pro Lys Phe Leu Glu Glu Ile
305                 310                 315                 320

Trp Asp Val

<210> SEQ ID NO 21
<211> LENGTH: 987
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 21
tgtgctatct gtggggaccg ctcctcaggc aaacactatg gggtatacag ttgtgagggc    60
tgcaagggct tcttcaagag gacagtacgc aaagacctga cctacacctg ccgagacaac   120
aaggactgcc tgatcgacaa gagacagcgg aaccggtgtc agtactgccg ctaccagaag   180
tgcctggcca tgggcatgaa gcgggaagct gtgcaggagg agcggcagcg gggcaaggac   240
cggaatgaga acgaggtgga gtccaccagc agtgccaacg aggacatgcc tgtagagaag   300
attctggaag ccgagcttgc tgtcgagccc aagactgaga catacgtgga ggcaaacatg   360
gggctgaacc ccagctcacc aaatgaccct gttaccaaca tctgtcaagc agcagacaag   420
cagctcttca ctcttgtgga gtgggccaag aggatcccac acttttctga gctgcccta    480 gacgaccagg tcatcctgct acgggcaggc tggaacgagc tgctgatcgc ctccttctcc   540
caccgctcca tagctgtgaa agatgggatt ctcctggcca ccggcctgca cgtacaccgg   600
aacagcgctc acagtgctgg ggtgggcgcc atctttgaca gggtgctaac agagctggtg   660
tctaagatgc gtgacatgca gatggacaag acggagctgg gctgcctgcg agccattgtc   720

```
ctgttcaacc ctgactctaa ggggctctca aaccctgctg aggtggaggc gttgagggag    780
aaggtgtatg cgtcactaga agcgtactgc aaacacaagt accctgagca gccgggcagg   840
tttgccaagc tgctgctccg cctgcctgca ctgcgttcca tcgggctcaa gtgcctggag   900
cacctgttct tcttcaagct catcggggac acgcccatcg acaccttcct catggagatg   960
ctggaggcac acatcaagc cacctag                                        987
```

<210> SEQ ID NO 22
<211> LENGTH: 789
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 22

```
aagcgggaag ctgtgcagga ggagcggcag cggggcaagg accggaatga gaacgaggtg    60
gagtccacca gcagtgccaa cgaggacatg cctgtagaga agattctgga agccgagctt   120
gctgtcgagc ccaagactga gacatacgtg gaggcaaaca tggggctgaa ccccagctca   180
ccaaatgacc ctgttaccaa catctgtcaa gcagcagaca agcagctctt cactcttgtg   240
gagtgggcca agaggatccc acactttcct gagctgcccc tagacgacca ggtcatcctg   300
ctacgggcag gctggaacga gctgctgatc gcctccttct cccaccgctc catagctgtg   360
aaagatggga ttctcctggc caccggcctg cacgtacacc ggaacagcgc tcacagtgct   420
ggggtgggcg ccatctttga cagggtgcta acagagctgg tgtctaagat gcgtgacatg   480
cagatggaca agacggagct gggctgcctg cgagccattg tcctgttcaa ccctgactct   540
aaggggctct caaaccctgc tgaggtggag gcgttgaggg agaaggtgta tgcgtcacta   600
gaagcgtact gcaaacacaa gtaccctgag cagccgggca ggtttgccaa gctgctgctc   660
cgcctgcctg cactgcgttc catcgggctc aagtgcctgg agcacctgtt cttcttcaag   720
ctcatcgggg acacgcccat cgacaccttc tcatggaga tgctggaggc accacatcaa   780
gccacctag                                                          789
```

<210> SEQ ID NO 23
<211> LENGTH: 714
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 23

```
gccaacgagg acatgcctgt agagaagatt ctggaagccg agcttgctgt cgagcccaag    60
actgagacat acgtggaggc aaacatgggg ctgaacccca gctcaccaaa tgaccctgtt   120
accaacatct gtcaagcagc agacaagcag ctcttcactc ttgtggagtg ggccaagagg   180
atcccacact ttctgagct gccctagac gaccaggtca tcctgctacg ggcaggctgg   240
aacgagctgc tgatcgccct cttctcccac cgctccatag ctgtgaaaga tgggattctc   300
ctggccaccg gcctgcacgt acaccggaac agcgctcaca gtgctgggt gggcgccatc   360 tttgacaggg tgctaacaga gctggtgtct aagatgcgtg acatgcagat ggacaagacg   420
gagctgggct gcctgcgagc cattgtcctg ttcaaccctg actctaaggg gctctcaaac   480
cctgctgagg tggaggcgtt gagggagaag gtgtatgcgt cactagaagc gtactgcaaa   540
cacaagtacc ctgagcagcc gggcaggttt gccaagctgc tgctccgcct gcctgcactg   600
```

```
cgttccatcg ggctcaagtg cctggagcac ctgttcttct tcaagctcat cggggacacg    660
cccatcgaca ccttcctcat ggagatgctg gaggcaccac atcaagccac ctag          714
```

<210> SEQ ID NO 24
<211> LENGTH: 536
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 24

```
ggatcccaca cttttctgag ctgcccctag acgaccaggt catcctgcta cgggcaggct     60
ggaacgagct gctgatcgcc tccttctccc accgctccat agctgtgaaa gatgggattc    120
tcctggccac cggcctgcac gtacaccgga acagcgctca cagtgctggg gtgggcgcca    180
tctttgacag ggtgctaaca gagctggtgt ctaagatgcg tgacatgcag atggacaaga    240
cggagctggg ctgcctgcga gccattgtcc tgttcaaccc tgactctaag ggctctcaa     300 accctgctga ggtggaggcg ttgagggaga aggtgtatgc gtcactagaa gcgtactgca    360
aacacaagta ccctgagcag ccgggcaggt ttgccaagct gctgctccgc ctgcctgcac    420
tgcgttccat cgggctcaag tgcctggagc acctgttctt cttcaagctc atcgggaca    480 cgcccatcga caccttcctc atggagatgc tggaggcacc acatcaagcc acctag       536
```

<210> SEQ ID NO 25
<211> LENGTH: 672
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 25

```
gccaacgagg acatgcctgt agagaagatt ctggaagccg agcttgctgt cgagcccaag     60
actgagacat acgtggaggc aaacatgggg ctgaacccca gctcaccaaa tgaccctgtt    120
accaacatct gtcaagcagc agacaagcag ctcttcactc ttgtggagtg ggccaagagg    180
atcccacact tttctgagct gcccctagac gaccaggtca tcctgctacg ggcaggctgg    240
aacgagctgc tgatcgcctc cttctcccac cgctccatag ctgtgaaaga tgggattctc    300
ctggccaccg gcctgcacgt acaccggaac agcgctcaca gtgctggggt gggcgccatc    360
tttgacaggg tgctaacaga gctggtgtct aagatgcgtg acatgcagat ggacaagacg    420
gagctgggct gcctgcgagc cattgtcctg ttcaaccctg actctaaggg gctctcaaac    480
cctgctgagg tggaggcgtt gagggagaag gtgtatgcgt cactagaagc gtactgcaaa    540
cacaagtacc ctgagcagcc gggcaggttt gccaagctgc tgctccgcct gcctgcactg    600
cgttccatcg gctcaagtg cctggagcac ctgttcttct tcaagctcat cggggacacg    660
cccatcgaca cc                                                        672
```

<210> SEQ ID NO 26
<211> LENGTH: 1123
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 26

```
tgcgccatct gcggggaccg ctcctcaggc aagcactatg gagtgtacag ctgcgagggg      60
tgcaagggct tcttcaagcg gacggtgcgc aaggacctga cctacacctg ccgcgacaac     120
aaggactgcc tgattgacaa gcggcagcgg aaccggtgcc agtactgccg ctaccagaag     180
tgcctggcca tgggcatgaa gcgggaagcc gtgcaggagg agcggcagcg tggcaaggac     240
cggaacgaga atgaggtgga gtcgaccagc agcgccaacg aggacatgcc ggtggagagg     300
atcctggagg ctgagctggc cgtggagccc aagaccgaga cctacgtgga ggcaaacatg     360
gggctgaacc ccagctcgcc gaacgaccct gtcaccaaca tttgccaagc agccgacaaa     420
cagcttttca ccctggtgga gtgggccaag cggatcccac acttctcaga gctgcccctg     480
gacgaccagg tcatcctgct gcgggcaggc tggaatgagc tgctcatcgc ctccttctcc     540
caccgctcca tcgccgtgaa ggacgggatc ctcctggcca ccgggctgca cgtccaccgg     600
aacagcgccc acagcgcagg ggtgggcgcc atctttgaca gggtgctgac ggagcttgtg     660
tccaagatgc gggacatgca gatggacaag acggagctgg gctgcctgcg cgccatcgtc     720
ctctttaacc ctgactccaa ggggctctcg aacccggccg aggtggaggc gctgagggag     780
aaggtctatg cgtccttgga ggcctactgc aagcacaagt acccagagca gccgggaagg     840
ttcgctaagc tcttgctccg cctgccggct ctgcgctcca tcgggctcaa atgcctggaa     900
catctcttct tcttcaagct catcggggac acacccattg acaccttcct tatggagatg     960
ctggaggcgc cgcaccaaat gacttaggcc tgcgggccca tcctttgtgc ccacccgttc    1020
tggccaccct gcctggacgc cagctgttct ctctcagcct gagccctgtcc ctgcccttct   1080 ctgcctggcc tgtttggact ttggggcaca gcctgtcact gct                     1123

<210> SEQ ID NO 27
<211> LENGTH: 925
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 27
aagcgggaag ccgtgcagga ggagcggcag cgtggcaagg accggaacga gaatgaggtg      60
gagtcgacca gcagcgccaa cgaggacatg ccggtggaga ggatcctgga ggctgagctg     120
gccgtggagc ccaagaccga gacctacgtg gaggcaaaca tggggctgaa ccccagctcg     180
ccgaacgacc ctgtcaccaa catttgccaa gcagccgaca aacagctttt caccctggtg     240
gagtgggcca agcggatccc acacttctca gagctgcccc tggacgacca ggtcatcctg     300
ctgcgggcag gctggaatga gctgctcatc gcctccttct cccaccgctc catcgccgtg     360
aaggacggga tcctcctggc caccgggctg cacgtccacc ggaacagcgc ccacagcgca     420
ggggtgggcg ccatctttga cagggtgctg acggagcttg tgtccaagat gcgggacatg     480
cagatggaca agacggagct gggctgcctg cgcgccatcg tcctcttta a ccctgactcc    540 aaggggctct cgaacccggc cgaggtggag gcgctgaggg agaaggtcta tgcgtccttg     600
gaggcctact gcaagcacaa gtacccagag cagccgggaa ggttcgctaa gctcttgctc     660
cgcctgccgg ctctgcgctc catcgggctc aaatgcctgg aacatctctt cttcttcaag     720
ctcatcgggg acacacccat tgacaccttc cttatggaga tgctggaggc gccgcaccaa     780
atgacttagg cctgcgggcc catcctttgt gcccacccgt tctggccacc ctgcctggac     840
gccagctgtt cttctcagcc tgagccctgt ccctgcccttc tctgcctggg cctgtttgga     900
```

```
ctttggggca cagcctgtca ctgct                                          925
```

<210> SEQ ID NO 28
<211> LENGTH: 850
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 28

```
gccaacgagg acatgccggt ggagaggatc ctggaggctg agctggccgt ggagcccaag     60
accgagacct acgtggaggc aaacatgggg ctgaacccca gctcgccgaa cgaccctgtc    120
accaacattt gccaagcagc cgacaaacag cttttcaccc tggtggagtg ggccaagcgg    180
atcccacact tctcagagct gccctggac gaccaggtca tcctgctgcg ggcaggctgg    240
aatgagctgc tcatcgcctc cttctcccac cgctccatcg ccgtgaagga cgggatcctc    300
ctggccaccg ggctgcacgt ccaccggaac agcgcccaca gcgcaggggt gggcgccatc    360
tttgacaggg tgctgacgga gcttgtgtcc aagatgcggg acatgcagat ggacaagacg    420
gagctgggct gcctgcgcgc catcgtcctc tttaaccctg actccaaggg gctctcgaac    480
ccggccgagg tggaggcgct gagggagaag gtctatgcgt ccttggaggc ctactgcaag    540
cacaagtacc cagagcagcc gggaaggttc gctaagctct tgctccgcct gccggctctg    600
cgctccatcg ggctcaaatg cctggaacat ctcttcttct tcaagctcat cggggacaca    660
cccattgaca ccttccttat ggagatgctg gaggcgccgc accaaatgac ttaggcctgc    720
gggcccatcc tttgtgccca cccgttctgg ccaccctgcc tggacgccag ctgttcttct    780
cagcctgagc cctgtccctg cccttctctg cctggcctgt ttggactttg gggcacagcc    840
tgtcactgct                                                            850
```

<210> SEQ ID NO 29
<211> LENGTH: 670
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 29

```
atcccacact tctcagagct gccctggac gaccaggtca tcctgctgcg ggcaggctgg     60
aatgagctgc tcatcgcctc cttctcccac cgctccatcg ccgtgaagga cgggatcctc    120
ctggccaccg ggctgcacgt ccaccggaac agcgcccaca gcgcaggggt gggcgccatc    180
tttgacaggg tgctgacgga gcttgtgtcc aagatgcggg acatgcagat ggacaagacg    240
gagctgggct gcctgcgcgc catcgtcctc tttaaccctg actccaaggg gctctcgaac    300
ccggccgagg tggaggcgct gagggagaag gtctatgcgt ccttggaggc ctactgcaag    360
cacaagtacc cagagcagcc gggaaggttc gctaagctct tgctccgcct gccggctctg    420
cgctccatcg ggctcaaatg cctggaacat ctcttcttct tcaagctcat cggggacaca    480
cccattgaca ccttccttat ggagatgctg gaggcgccgc accaaatgac ttaggcctgc    540
gggcccatcc tttgtgccca cccgttctgg ccaccctgcc tggacgccag ctgttcttct    600
cagcctgagc cctgtccctg cccttctctg cctggcctgt ttggactttg gggcacagcc    660
tgtcactgct                                                            670
```

<210> SEQ ID NO 30
<211> LENGTH: 672
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 30

```
gccaacgagg acatgccggt ggagaggatc ctggaggctg agctggccgt ggagcccaag      60
accgagacct acgtggaggc aaacatgggg ctgaacccca gctcgccgaa cgaccctgtc     120
accaacattt gccaagcagc cgacaaacag cttttcaccc tggtggagtg ggccaagcgg     180
atcccacact tctcagagct gcccctggac gaccaggtca tcctgctgcg ggcaggctgg     240
aatgagctgc tcatcgcctc cttctcccac cgctccatcg ccgtgaagga cgggatcctc     300
ctggccaccg ggctgcacgt ccaccggaac agcgcccaca gcgcaggggt gggcgccatc     360
tttgacaggg tgctgacgga gcttgtgtcc aagatgcggg acatgcagat ggacaagacg     420
gagctgggct gcctgcgcgc catcgtcctc tttaaccctg actccaaggg gctctcgaac     480
ccggccgagg tggaggcgct gagggagaag gtctatgcgt ccttggaggc ctactgcaag     540
cacaagtacc cagagcagcc gggaaggttc gctaagctct tgctccgcct gccggctctg     600
cgctccatcg ggctcaaatg cctggaacat ctcttcttct tcaagctcat cggggacaca     660
cccattgaca cc                                                         672
```

<210> SEQ ID NO 31
<211> LENGTH: 328
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 31

```
Cys Ala Ile Cys Gly Asp Arg Ser Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30

Leu Thr Tyr Thr Cys Arg Asp Asn Lys Asp Cys Leu Ile Asp Lys Arg
        35                  40                  45

Gln Arg Asn Arg Cys Gln Tyr Cys Arg Tyr Gln Lys Cys Leu Ala Met
    50                  55                  60

Gly Met Lys Arg Glu Ala Val Gln Glu Glu Arg Gln Arg Gly Lys Asp
65                  70                  75                  80

Arg Asn Glu Asn Glu Val Glu Ser Thr Ser Ser Ala Asn Glu Asp Met
                85                  90                  95

Pro Val Glu Lys Ile Leu Glu Ala Glu Leu Ala Val Glu Pro Lys Thr
            100                 105                 110

Glu Thr Tyr Val Glu Ala Asn Met Gly Leu Asn Pro Ser Ser Pro Asn
        115                 120                 125

Asp Pro Val Thr Asn Ile Cys Gln Ala Ala Asp Lys Gln Leu Phe Thr
    130                 135                 140

Leu Val Glu Trp Ala Lys Arg Ile Pro His Phe Ser Glu Leu Pro Leu
145                 150                 155                 160

Asp Asp Gln Val Ile Leu Leu Arg Ala Gly Trp Asn Glu Leu Leu Ile
                165                 170                 175
```

```
Ala Ser Phe Ser His Arg Ser Ile Ala Val Lys Asp Gly Ile Leu Leu
                180                 185                 190

Ala Thr Gly Leu His Val His Arg Asn Ser Ala His Ser Ala Gly Val
        195                 200                 205

Gly Ala Ile Phe Asp Arg Val Leu Thr Glu Leu Val Ser Lys Met Arg
        210                 215                 220

Asp Met Gln Met Asp Lys Thr Glu Leu Gly Cys Leu Arg Ala Ile Val
225                 230                 235                 240

Leu Phe Asn Pro Asp Ser Lys Gly Leu Ser Asn Pro Ala Glu Val Glu
                245                 250                 255

Ala Leu Arg Glu Lys Val Tyr Ala Ser Leu Glu Ala Tyr Cys Lys His
        260                 265                 270

Lys Tyr Pro Glu Gln Pro Gly Arg Phe Ala Lys Leu Leu Leu Arg Leu
        275                 280                 285

Pro Ala Leu Arg Ser Ile Gly Leu Lys Cys Leu Glu His Leu Phe Phe
        290                 295                 300

Phe Lys Leu Ile Gly Asp Thr Pro Ile Asp Thr Phe Leu Met Glu Met
305                 310                 315                 320

Leu Glu Ala Pro His Gln Ala Thr
                325

<210> SEQ ID NO 32
<211> LENGTH: 262
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 32

Lys Arg Glu Ala Val Gln Glu Glu Arg Gln Arg Gly Lys Asp Arg Asn
1               5                   10                  15

Glu Asn Glu Val Glu Ser Thr Ser Ser Ala Asn Glu Asp Met Pro Val
                20                  25                  30

Glu Lys Ile Leu Glu Ala Glu Leu Ala Val Glu Pro Lys Thr Glu Thr
        35                  40                  45

Tyr Val Glu Ala Asn Met Gly Leu Asn Pro Ser Ser Pro Asn Asp Pro
    50                  55                  60

Val Thr Asn Ile Cys Gln Ala Ala Asp Lys Gln Leu Phe Thr Leu Val
65                  70                  75                  80

Glu Trp Ala Lys Arg Ile Pro His Phe Ser Glu Leu Pro Leu Asp Asp
                85                  90                  95

Gln Val Ile Leu Leu Arg Ala Gly Trp Asn Glu Leu Leu Ile Ala Ser
            100                 105                 110

Phe Ser His Arg Ser Ile Ala Val Lys Asp Gly Ile Leu Leu Ala Thr
        115                 120                 125

Gly Leu His Val His Arg Asn Ser Ala His Ser Ala Gly Val Gly Ala
    130                 135                 140

Ile Phe Asp Arg Val Leu Thr Glu Leu Val Ser Lys Met Arg Asp Met
145                 150                 155                 160

Gln Met Asp Lys Thr Glu Leu Gly Cys Leu Arg Ala Ile Val Leu Phe
                165                 170                 175

Asn Pro Asp Ser Lys Gly Leu Ser Asn Pro Ala Glu Val Glu Ala Leu
            180                 185                 190

Arg Glu Lys Val Tyr Ala Ser Leu Glu Ala Tyr Cys Lys His Lys Tyr
        195                 200                 205
```

```
Pro Glu Gln Pro Gly Arg Phe Ala Lys Leu Leu Arg Leu Pro Ala
    210             215                 220

Leu Arg Ser Ile Gly Leu Lys Cys Leu Glu His Leu Phe Phe Lys
225             230                 235                 240

Leu Ile Gly Asp Thr Pro Ile Asp Thr Phe Leu Met Glu Met Leu Glu
                245             250                 255

Ala Pro His Gln Ala Thr
            260

<210> SEQ ID NO 33
<211> LENGTH: 237
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 33

Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
                20                  25                  30

Pro Ser Ser Pro Asn Asp Pro Val Thr Asn Ile Cys Gln Ala Ala Asp
            35                  40                  45

Lys Gln Leu Phe Thr Leu Val Glu Trp Ala Lys Arg Ile Pro His Phe
    50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
                100                 105                 110

His Ser Ala Gly Val Gly Ala Ile Phe Asp Arg Val Leu Thr Glu Leu
            115                 120                 125

Val Ser Lys Met Arg Asp Met Gln Met Asp Lys Thr Glu Leu Gly Cys
130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Lys Leu Ile Gly Asp Thr Pro Ile Asp Thr
    210                 215                 220

Phe Leu Met Glu Met Leu Glu Ala Pro His Gln Ala Thr
225                 230                 235

<210> SEQ ID NO 34
<211> LENGTH: 177
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 34
```

```
Ile Pro His Phe Ser Glu Leu Pro Leu Asp Asp Gln Val Ile Leu Leu
1               5                   10                  15

Arg Ala Gly Trp Asn Glu Leu Leu Ile Ala Ser Phe Ser His Arg Ser
            20                  25                  30

Ile Ala Val Lys Asp Gly Ile Leu Leu Ala Thr Gly Leu His Val His
            35                  40                  45

Arg Asn Ser Ala His Ser Ala Gly Val Gly Ala Ile Phe Asp Arg Val
        50                  55                  60

Leu Thr Glu Leu Val Ser Lys Met Arg Asp Met Gln Met Asp Lys Thr
65                  70                  75                  80

Glu Leu Gly Cys Leu Arg Ala Ile Val Leu Phe Asn Pro Asp Ser Lys
                85                  90                  95

Gly Leu Ser Asn Pro Ala Glu Val Glu Ala Leu Arg Glu Lys Val Tyr
            100                 105                 110

Ala Ser Leu Glu Ala Tyr Cys Lys His Lys Tyr Pro Glu Gln Pro Gly
        115                 120                 125

Arg Phe Ala Lys Leu Leu Leu Arg Leu Pro Ala Leu Arg Ser Ile Gly
    130                 135                 140

Leu Lys Cys Leu Glu His Leu Phe Phe Phe Lys Leu Ile Gly Asp Thr
145                 150                 155                 160

Pro Ile Asp Thr Phe Leu Met Glu Met Leu Glu Ala Pro His Gln Ala
                165                 170                 175

Thr
```

<210> SEQ ID NO 35
<211> LENGTH: 224
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 35

```
Ala Asn Glu Asp Met Pro Val Glu Lys Ile Leu Glu Ala Glu Leu Ala
1               5                   10                  15

Val Glu Pro Lys Thr Glu Thr Tyr Val Glu Ala Asn Met Gly Leu Asn
            20                  25                  30

Pro Ser Ser Pro Asn Asp Pro Val Thr Asn Ile Cys Gln Ala Ala Asp
            35                  40                  45

Lys Gln Leu Phe Thr Leu Val Glu Trp Ala Lys Arg Ile Pro His Phe
        50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
    130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175
```

```
Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
            195                 200                 205

Glu His Leu Phe Phe Lys Leu Ile Gly Asp Thr Pro Ile Asp Thr
            210                 215                 220

<210> SEQ ID NO 36
<211> LENGTH: 328
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 36

Cys Ala Ile Cys Gly Asp Arg Ser Ser Gly Lys His Tyr Gly Val Tyr
1               5                   10                  15

Ser Cys Glu Gly Cys Lys Gly Phe Phe Lys Arg Thr Val Arg Lys Asp
            20                  25                  30

Leu Thr Tyr Thr Cys Arg Asp Asn Lys Asp Cys Leu Ile Asp Lys Arg
        35                  40                  45

Gln Arg Asn Arg Cys Gln Tyr Cys Arg Tyr Gln Lys Cys Leu Ala Met
    50                  55                  60

Gly Met Lys Arg Glu Ala Val Gln Glu Glu Arg Gln Arg Gly Lys Asp
65                  70                  75                  80

Arg Asn Glu Asn Glu Val Glu Ser Thr Ser Ser Ala Asn Glu Asp Met
                85                  90                  95

Pro Val Glu Arg Ile Leu Glu Ala Glu Leu Ala Val Glu Pro Lys Thr
            100                 105                 110

Glu Thr Tyr Val Glu Ala Asn Met Gly Leu Asn Pro Ser Ser Pro Asn
        115                 120                 125

Asp Pro Val Thr Asn Ile Cys Gln Ala Ala Asp Lys Gln Leu Phe Thr
    130                 135                 140

Leu Val Glu Trp Ala Lys Arg Ile Pro His Phe Ser Glu Leu Pro Leu
145                 150                 155                 160

Asp Asp Gln Val Ile Leu Leu Arg Ala Gly Trp Asn Glu Leu Leu Ile
                165                 170                 175

Ala Ser Phe Ser His Arg Ser Ile Ala Val Lys Asp Gly Ile Leu Leu
            180                 185                 190

Ala Thr Gly Leu His Val His Arg Asn Ser Ala His Ser Ala Gly Val
        195                 200                 205

Gly Ala Ile Phe Asp Arg Val Leu Thr Glu Leu Val Ser Lys Met Arg
    210                 215                 220

Asp Met Gln Met Asp Lys Thr Glu Leu Gly Cys Leu Arg Ala Ile Val
225                 230                 235                 240

Leu Phe Asn Pro Asp Ser Lys Gly Leu Ser Asn Pro Ala Glu Val Glu
                245                 250                 255

Ala Leu Arg Glu Lys Val Tyr Ala Ser Leu Glu Ala Tyr Cys Lys His
            260                 265                 270

Lys Tyr Pro Glu Gln Pro Gly Arg Phe Ala Lys Leu Leu Leu Arg Leu
        275                 280                 285

Pro Ala Leu Arg Ser Ile Gly Leu Lys Cys Leu Glu His Leu Phe Phe
    290                 295                 300

Phe Lys Leu Ile Gly Asp Thr Pro Ile Asp Thr Phe Leu Met Glu Met
```

Leu Glu Ala Pro His Gln Met Thr
                325

<210> SEQ ID NO 37
<211> LENGTH: 262
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 37

Lys Arg Glu Ala Val Gln Glu Arg Gln Arg Gly Lys Asp Arg Asn
1               5                   10                  15

Glu Asn Glu Val Glu Ser Thr Ser Ser Ala Asn Glu Asp Met Pro Val
                20                  25                  30

Glu Arg Ile Leu Glu Ala Glu Leu Ala Val Glu Pro Lys Thr Glu Thr
            35                  40                  45

Tyr Val Glu Ala Asn Met Gly Leu Asn Pro Ser Ser Pro Asn Asp Pro
        50                  55                  60

Val Thr Asn Ile Cys Gln Ala Ala Asp Lys Gln Leu Phe Thr Leu Val
65                  70                  75                  80

Glu Trp Ala Lys Arg Ile Pro His Phe Ser Glu Leu Pro Leu Asp Asp
                85                  90                  95

Gln Val Ile Leu Leu Arg Ala Gly Trp Asn Glu Leu Leu Ile Ala Ser
            100                 105                 110

Phe Ser His Arg Ser Ile Ala Val Lys Asp Gly Ile Leu Leu Ala Thr
        115                 120                 125

Gly Leu His Val His Arg Asn Ser Ala His Ser Ala Gly Val Gly Ala
    130                 135                 140

Ile Phe Asp Arg Val Leu Thr Glu Leu Val Ser Lys Met Arg Asp Met
145                 150                 155                 160

Gln Met Asp Lys Thr Glu Leu Gly Cys Leu Arg Ala Ile Val Leu Phe
                165                 170                 175

Asn Pro Asp Ser Lys Gly Leu Ser Asn Pro Ala Glu Val Glu Ala Leu
            180                 185                 190

Arg Glu Lys Val Tyr Ala Ser Leu Glu Ala Tyr Cys Lys His Lys Tyr
        195                 200                 205

Pro Glu Gln Pro Gly Arg Phe Ala Lys Leu Leu Leu Arg Leu Pro Ala
    210                 215                 220

Leu Arg Ser Ile Gly Leu Lys Cys Leu Glu His Leu Phe Phe Phe Lys
225                 230                 235                 240

Leu Ile Gly Asp Thr Pro Ile Asp Thr Phe Leu Met Glu Met Leu Glu
                245                 250                 255

Ala Pro His Gln Met Thr
            260

<210> SEQ ID NO 38
<211> LENGTH: 237
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 38

Ala Asn Glu Asp Met Pro Val Glu Arg Ile Leu Glu Ala Glu Leu Ala

```
 1               5                  10                 15
Val Glu Pro Lys Thr Glu Thr Tyr Val Glu Ala Asn Met Gly Leu Asn
                20                 25                 30

Pro Ser Ser Pro Asn Asp Pro Val Thr Asn Ile Cys Gln Ala Ala Asp
                35                 40                 45

Lys Gln Leu Phe Thr Leu Val Glu Trp Ala Lys Arg Ile Pro His Phe
    50                 55                 60

Ser Glu Leu Pro Leu Asp Asp Gln Val Ile Leu Leu Arg Ala Gly Trp
65                  70                 75                 80

Asn Glu Leu Leu Ile Ala Ser Phe Ser His Arg Ser Ile Ala Val Lys
                85                 90                 95

Asp Gly Ile Leu Leu Ala Thr Gly Leu His Val His Arg Asn Ser Ala
                100                105                110

His Ser Ala Gly Val Gly Ala Ile Phe Asp Arg Val Leu Thr Glu Leu
            115                120                125

Val Ser Lys Met Arg Asp Met Gln Met Asp Lys Thr Glu Leu Gly Cys
130                 135                140

Leu Arg Ala Ile Val Leu Phe Asn Pro Asp Ser Lys Gly Leu Ser Asn
145                 150                155                160

Pro Ala Glu Val Glu Ala Leu Arg Glu Lys Val Tyr Ala Ser Leu Glu
                165                170                175

Ala Tyr Cys Lys His Lys Tyr Pro Glu Gln Pro Gly Arg Phe Ala Lys
            180                185                190

Leu Leu Leu Arg Leu Pro Ala Leu Arg Ser Ile Gly Leu Lys Cys Leu
            195                200                205

Glu His Leu Phe Phe Phe Lys Leu Ile Gly Asp Thr Pro Ile Asp Thr
    210                215                220

Phe Leu Met Glu Met Leu Glu Ala Pro His Gln Met Thr
225                 230                235

<210> SEQ ID NO 39
<211> LENGTH: 177
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 39

Ile Pro His Phe Ser Glu Leu Pro Leu Asp Asp Gln Val Ile Leu Leu
1               5                  10                 15

Arg Ala Gly Trp Asn Glu Leu Leu Ile Ala Ser Phe Ser His Arg Ser
                20                 25                 30

Ile Ala Val Lys Asp Gly Ile Leu Leu Ala Thr Gly Leu His Val His
            35                 40                 45

Arg Asn Ser Ala His Ser Ala Gly Val Gly Ala Ile Phe Asp Arg Val
50                  55                 60

Leu Thr Glu Leu Val Ser Lys Met Arg Asp Met Gln Met Asp Lys Thr
65                  70                 75                 80

Glu Leu Gly Cys Leu Arg Ala Ile Val Leu Phe Asn Pro Asp Ser Lys
                85                 90                 95

Gly Leu Ser Asn Pro Ala Glu Val Glu Ala Leu Arg Glu Lys Val Tyr
            100                105                110

Ala Ser Leu Glu Ala Tyr Cys Lys His Lys Tyr Pro Glu Gln Pro Gly
            115                120                125
```

```
Arg Phe Ala Lys Leu Leu Leu Arg Leu Pro Ala Leu Arg Ser Ile Gly
130                 135                 140

Leu Lys Cys Leu Glu His Leu Phe Phe Lys Leu Ile Gly Asp Thr
145                 150                 155                 160

Pro Ile Asp Thr Phe Leu Met Glu Met Leu Glu Ala Pro His Gln Met
                165                 170                 175

Thr

<210> SEQ ID NO 40
<211> LENGTH: 224
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 40

Ala Asn Glu Asp Met Pro Val Glu Arg Ile Leu Glu Ala Glu Leu Ala
1               5                   10                  15

Val Glu Pro Lys Thr Glu Thr Tyr Val Glu Ala Asn Met Gly Leu Asn
                20                  25                  30

Pro Ser Ser Pro Asn Asp Pro Val Thr Asn Ile Cys Gln Ala Ala Asp
            35                  40                  45

Lys Gln Leu Phe Thr Leu Val Glu Trp Ala Lys Arg Ile Pro His Phe
50                  55                  60

Ser Glu Leu Pro Leu Asp Asp Gln Val Ile Leu Leu Arg Ala Gly Trp
65                  70                  75                  80

Asn Glu Leu Leu Ile Ala Ser Phe Ser His Arg Ser Ile Ala Val Lys
                85                  90                  95

Asp Gly Ile Leu Leu Ala Thr Gly Leu His Val His Arg Asn Ser Ala
            100                 105                 110

His Ser Ala Gly Val Gly Ala Ile Phe Asp Arg Val Leu Thr Glu Leu
        115                 120                 125

Val Ser Lys Met Arg Asp Met Gln Met Asp Lys Thr Glu Leu Gly Cys
130                 135                 140

Leu Arg Ala Ile Val Leu Phe Asn Pro Asp Ser Lys Gly Leu Ser Asn
145                 150                 155                 160

Pro Ala Glu Val Glu Ala Leu Arg Glu Lys Val Tyr Ala Ser Leu Glu
                165                 170                 175

Ala Tyr Cys Lys His Lys Tyr Pro Glu Gln Pro Gly Arg Phe Ala Lys
            180                 185                 190

Leu Leu Leu Arg Leu Pro Ala Leu Arg Ser Ile Gly Leu Lys Cys Leu
        195                 200                 205

Glu His Leu Phe Phe Phe Lys Leu Ile Gly Asp Thr Pro Ile Asp Thr
    210                 215                 220

<210> SEQ ID NO 41
<211> LENGTH: 441
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 41
atgaagctac tgtcttctat cgaacaagca tgcgatattt gccgacttaa aaagctcaag      60
tgctccaaag aaaaaccgaa gtgcgccaag tgtctgaaga caactgggag tgtcgctac     120
```

```
tctcccaaaa ccaaaaggtc tccgctgact agggcacatc tgacagaagt ggaatcaagg    180
ctagaaagac tggaacagct atttctactg attttttcctc gagaagacct tgacatgatt    240
ttgaaaatgg attctttaca ggatataaaa gcattgttaa caggattatt tgtacaagat    300
aatgtgaata aagatgccgt cacagataga ttggcttcag tggagactga tatgcctcta    360
acattgagac agcatagaat aagtgcgaca tcatcatcgg aagagagtag taacaaaggt    420
caaagacagt tgactgtatc g                                              441
```

<210> SEQ ID NO 42
<211> LENGTH: 147
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 42

```
Met Lys Leu Leu Ser Ser Ile Glu Gln Ala Cys Asp Ile Cys Arg Leu
 1               5                  10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145
```

<210> SEQ ID NO 43
<211> LENGTH: 606
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 43

```
atgaaagcgt taacggccag caacaagag gtgtttgatc tcatccgtga tcacatcagc     60
cagacaggta tgccgccgac gcgtgcggaa atcgcgcagc gtttggggtt ccgttcccca   120
aacgcggctg aagaacatct gaaggcgctg gcacgcaaag gcgttattga aattgttttcc   180 ggcgcatcac gcgggattcg tctgttgcag gaagaggaag aagggttgcc gctggtaggt   240
cgtgtggctg ccggtgaacc acttctggcg caacagcata ttgaaggtca ttatcaggtc   300
gatccttcct tattcaagcc gaatgctgat ttcctgctgc gcgtcagcgg gatgtcgatg   360
aaagatatcg gcattatgga tggtgacttg ctggcagtgc ataaaactca ggatgtacgt   420
aacggtcagg tcgttgtcgc acgtattgat gacgaagtta ccgttaagcg cctgaaaaaa   480
```

```
cagggcaata aagtcgaact gttgccagaa aatagcgagt ttaaaccaat tgtcgtagat    540
cttcgtcagc agagcttcac cattgaaggg ctggcggttg gggttattcg caacggcgac    600
tggctg                                                               606
```

<210> SEQ ID NO 44
<211> LENGTH: 202
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 44

```
Met Lys Ala Leu Thr Ala Arg Gln Gln Glu Val Phe Asp Leu Ile Arg
1               5                   10                  15

Asp His Ile Ser Gln Thr Gly Met Pro Pro Thr Arg Ala Glu Ile Ala
            20                  25                  30

Gln Arg Leu Gly Phe Arg Ser Pro Asn Ala Ala Glu Glu His Leu Lys
        35                  40                  45

Ala Leu Ala Arg Lys Gly Val Ile Glu Ile Val Ser Gly Ala Ser Arg
    50                  55                  60

Gly Ile Arg Leu Leu Gln Glu Glu Glu Gly Leu Pro Leu Val Gly
65                  70                  75                  80

Arg Val Ala Ala Gly Glu Pro Leu Leu Ala Gln His Ile Glu Gly
                85                  90                  95

His Tyr Gln Val Asp Pro Ser Leu Phe Lys Pro Asn Ala Asp Phe Leu
            100                 105                 110

Leu Arg Val Ser Gly Met Ser Met Lys Asp Ile Gly Ile Met Asp Gly
        115                 120                 125

Asp Leu Leu Ala Val His Lys Thr Gln Asp Val Arg Asn Gly Gln Val
    130                 135                 140

Val Val Ala Arg Ile Asp Asp Glu Val Thr Val Lys Arg Leu Lys Lys
145                 150                 155                 160

Gln Gly Asn Lys Val Glu Leu Leu Pro Glu Asn Ser Glu Phe Lys Pro
                165                 170                 175

Ile Val Val Asp Leu Arg Gln Gln Ser Phe Thr Ile Glu Gly Leu Ala
            180                 185                 190

Val Gly Val Ile Arg Asn Gly Asp Trp Leu
        195                 200
```

<210> SEQ ID NO 45
<211> LENGTH: 271
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 45

```
atgggcccta aaagaagcg taaagtcgcc cccccgaccg atgtcagcct gggggacgag    60
ctccacttag acggcgagga cgtggcgatg gcgcatgccg acgcgctaga cgatttcgat   120
ctggacatgt tggggacgg ggattccccg gggccgggat ttaccccca cgactccgcc   180 ccctacggcg ctctggatat ggccgacttc gagtttgagc agatgtttac cgatgccctt   240
ggaattgacg agtacggtgg ggaattcccg g                                  271
```

<210> SEQ ID NO 46
<211> LENGTH: 90
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 46

```
Met Gly Pro Lys Lys Arg Lys Val Ala Pro Pro Thr Asp Val Ser
1               5                   10                  15

Leu Gly Asp Glu Leu His Leu Asp Gly Glu Asp Val Ala Met Ala His
                20                  25                  30

Ala Asp Ala Leu Asp Asp Phe Asp Leu Asp Met Leu Gly Asp Gly Asp
                35                  40                  45

Ser Pro Gly Pro Gly Phe Thr Pro His Asp Ser Ala Pro Tyr Gly Ala
    50                  55                  60

Leu Asp Met Ala Asp Phe Glu Phe Glu Gln Met Phe Thr Asp Ala Leu
65                  70                  75                  80

Gly Ile Asp Glu Tyr Gly Gly Glu Phe Pro
                85                  90
```

<210> SEQ ID NO 47
<211> LENGTH: 19
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 47

```
ggagtactgt cctccgagc                                               19
```

<210> SEQ ID NO 48
<211> LENGTH: 666
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 48

```
ggatccccag cttggaattc gacaggttat cagcaacaac acagtcatat ccattctcaa     60
ttagctctac cacagtgtgt gaaccaatgt atccagcacc acctgtaacc aaaacaattt    120
tagaagtact tcactttgt aactgagctg tcatttatat tgaattttca aaaattctta     180
cttttttttt ggatggacgc aaagaagttt aataatcata ttacatggca ttaccaccat    240
atacatatcc atatacatat ccatatctaa tcttacctcg actgctgtat ataaaaccag    300
tggttatatg tacagtactg ctgtatataa aaccagtggt tatatgtaca gtacgtcgac    360
tgctgtatat aaaaccagtg gttatatgta cagtactgct gtatataaaa ccagtggtta    420
tatgtacagt acgtcgaggg atgataatgc gattagtttt ttagccttat ttctggggta    480
attaatcagc gaagcgatga ttttgatct attaacagat atataaatgc aaaaactgca    540
taaccacttt aactaatact ttcaacattt tcggtttgta ttacttctta ttcaaatgta    600
ataaaagtat caacaaaaaa ttgttaatat acctctatac tttaacgtca aggagaaaaa    660
actata                                                              666
```

<210> SEQ ID NO 49
<211> LENGTH: 1542

```
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 49
ctggacctga aacacgaagt ggcttaccga ggggtgctcc caggccaggt gaaggccgaa      60
ccggggtcc acaacggcca ggtcaacggc cacgtgaggg actggatggc aggcggcgct     120
ggtgccaatt cgccgtctcc gggagcggtg gctcaacccc agcctaacaa tgggtattcg    180
tcgccactct cctcgggaag ctacgggccc tacagtccaa atgggaaaat aggccgtgag    240
gaactgtcgc cagcttcaag tataaatggg tgcagtacag atggcgaggc acgacgtcag    300
aagaagggcc ctgcgcccg tcagcaagag gaactgtgtc tggtatgcgg ggacagagcc     360
tccggatacc actacaatgc gctcacgtgt gaaggggtgta aagggttctt cagacggagt    420
gttaccaaaa atgcggttta tatttgtaaa ttcggtcacg cttgcgaaat ggacatgtac    480
atgcgacgga aatgccagga gtgccgcctg aagaagtgct tagctgtagg catgaggcct    540
gagtgcgtag tacccgagac tcagtgcgcc atgaagcgga aagagaagaa agcacagaag    600
gagaaggaca aactgcctgt cagcacgacg acggtggacg accacatgcc gcccattatg    660
cagtgtgaac ctccacctcc tgaagcagca aggattcacg aagtggtccc aaggtttctc    720
tccgacaagc tgttggagac aaaccggcag aaaaacatcc cccagttgac agccaaccag    780
cagttcctta tcgccaggct catctggtac caggacgggt acgagcagcc ttctgatgaa    840
gatttgaaga ggattacgca gacgtggcag caagcggacg atgaaaacga agagtctgac    900
actccccttcc gccagatcac agagatgact atcctcacgg tccaacttat cgtggagttc    960
gcgaagggat tgccagggtt cgccaagatc tcgcagcctg atcaaattac gctgcttaag   1020
gcttgctcaa gtgaggtaat gatgctccga gtcgcgcgac gatacgatgc ggcctcagac   1080
agtgttctgt tcgcgaacaa ccaagcgtac actcgcgaca actaccgcaa ggctggcatg   1140
gcctacgtca tcgaggatct actgcacttc tgccggtgca tgtactctat ggcgttggac   1200
aacatccatt acgcgctgct cacggctgtc gtcatctttt ctgaccggcc agggttggag   1260
cagccgcaac tggtggaaga aatccagcgg tactacctga atacgctccg catctatatc   1320
ctgaaccagc tgagcgggtc ggcgcgttcg tccgtcatat acggcaagat cctctcaatc   1380
ctctctgagc tacgcacgct cggcatgcaa aactccaaca tgtgcatctc cctcaagctc   1440
aagaacagaa agctgccgcc tttcctcgag gagatctggg atgtggcgga catgtcgcac   1500
acccaaccgc cgcctatcct cgagtccccc acgaatctct ag                      1542

<210> SEQ ID NO 50
<211> LENGTH: 513
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 50

Leu Asp Leu Lys His Glu Val Ala Tyr Arg Gly Val Leu Pro Gly Gln
 1               5                  10                  15

Val Lys Ala Glu Pro Gly Val His Asn Gly Gln Val Asn Gly His Val
            20                  25                  30

Arg Asp Trp Met Ala Gly Gly Ala Gly Ala Asn Ser Pro Ser Pro Gly
        35                  40                  45
```

```
Ala Val Ala Gln Pro Gln Pro Asn Asn Gly Tyr Ser Ser Pro Leu Ser
         50              55                  60
Ser Gly Ser Tyr Gly Pro Tyr Ser Pro Asn Gly Lys Ile Gly Arg Glu
 65              70                  75                      80
Glu Leu Ser Pro Ala Ser Ser Ile Asn Gly Cys Ser Thr Asp Gly Glu
                 85                  90                  95
Ala Arg Arg Gln Lys Lys Gly Pro Ala Pro Arg Gln Gln Glu Glu Leu
                 100                 105                 110
Cys Leu Val Cys Gly Asp Arg Ala Ser Gly Tyr His Tyr Asn Ala Leu
             115                 120                 125
Thr Cys Glu Gly Cys Lys Gly Phe Phe Arg Arg Ser Val Thr Lys Asn
         130                 135                 140
Ala Val Tyr Ile Cys Lys Phe Gly His Ala Cys Glu Met Asp Met Tyr
145                 150                 155                 160
Met Arg Arg Lys Cys Gln Glu Cys Arg Leu Lys Lys Cys Leu Ala Val
                 165                 170                 175
Gly Met Arg Pro Glu Cys Val Val Pro Glu Thr Gln Cys Ala Met Lys
             180                 185                 190
Arg Lys Glu Lys Lys Ala Gln Lys Glu Lys Asp Lys Leu Pro Val Ser
         195                 200                 205
Thr Thr Thr Val Asp Asp His Met Pro Pro Ile Met Gln Cys Glu Pro
210                 215                 220
Pro Pro Pro Glu Ala Ala Arg Ile His Glu Val Val Pro Arg Phe Leu
225                 230                 235                 240
Ser Asp Lys Leu Leu Glu Thr Asn Arg Gln Lys Asn Ile Pro Gln Leu
                 245                 250                 255
Thr Ala Asn Gln Gln Phe Leu Ile Ala Arg Leu Ile Trp Tyr Gln Asp
             260                 265                 270
Gly Tyr Glu Gln Pro Ser Asp Glu Asp Leu Lys Arg Ile Thr Gln Thr
         275                 280                 285
Trp Gln Gln Ala Asp Asp Glu Asn Glu Glu Ser Asp Thr Pro Phe Arg
         290                 295                 300
Gln Ile Thr Glu Met Thr Ile Leu Thr Val Gln Leu Ile Val Glu Phe
305                 310                 315                 320
Ala Lys Gly Leu Pro Gly Phe Ala Lys Ile Ser Gln Pro Asp Gln Ile
             325                 330                 335
Thr Leu Leu Lys Ala Cys Ser Ser Glu Val Met Met Leu Arg Val Ala
             340                 345                 350
Arg Arg Tyr Asp Ala Ala Ser Asp Ser Val Leu Phe Ala Asn Asn Gln
         355                 360                 365
Ala Tyr Thr Arg Asp Asn Tyr Arg Lys Ala Gly Met Ala Tyr Val Ile
         370                 375                 380
Glu Asp Leu Leu His Phe Cys Arg Cys Met Tyr Ser Met Ala Leu Asp
385                 390                 395                 400
Asn Ile His Tyr Ala Leu Leu Thr Ala Val Val Ile Phe Ser Asp Arg
             405                 410                 415
Pro Gly Leu Glu Gln Pro Gln Leu Val Glu Glu Ile Gln Arg Tyr Tyr
             420                 425                 430
Leu Asn Thr Leu Arg Ile Tyr Ile Leu Asn Gln Leu Ser Gly Ser Ala
         435                 440                 445
Arg Ser Ser Val Ile Tyr Gly Lys Ile Leu Ser Ile Leu Ser Glu Leu
         450                 455                 460
```

```
Arg Thr Leu Gly Met Gln Asn Ser Asn Met Cys Ile Ser Leu Lys Leu
465                 470                 475                 480

Lys Asn Arg Lys Leu Pro Pro Phe Leu Glu Glu Ile Trp Asp Val Ala
            485                 490                 495

Asp Met Ser His Thr Gln Pro Pro Pro Ile Leu Glu Ser Pro Thr Asn
            500                 505                 510

Leu

<210> SEQ ID NO 51
<211> LENGTH: 4375
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 51
tgtaattttg atgggcgccg tgatgcaccg tgtgccatat tgccatccag tcgaatagaa      60
aaaaaaaaaa aaaaaaaaat atcagttgtt ttgtccctcg ctcgctttcg agtgtattcg     120
gaatattaga cgtcataatt cacgagtgtc ttttaaattt atatagcgat tagcggggcc     180
gtttgttgga cgtgcgcttg cgtttagtgg agtgcaggga tagtgaggcg agtatggtag     240
ttcgtggtca tgtcaagtgt ggcgaagaaa gacaagccga cgatgtcggt gacggcgctg     300
atcaactggg cgcggccggc gccgccaggc ccgccgcagc cgcagtcagc gtcgcctgcg     360
ccggcagcca tgctgcagca gctcccgacg cagtcaatgc agtcgttaaa ccacatccca     420
actgtcgatt gctcgctcga tatgcagtgg cttaatttag aacctggatt catgtcgcct     480
atgtcacctc ctgagatgaa accagacacc gccatgcttg atgggctacg agacgacgcc     540
acttcgccgc ctaacttcaa gaactacccg cctaatcacc ccctgagtgg ctccaaacac     600
ctatgctcta tatgcggcga cagggcgtct gggaagcact atggggtgta cagttgcgaa     660
ggatgcaagg gtttcttcaa gcggaccgtc cggaaggacc tgtcgtacgc ttgccgggag     720
gagcggaact gcatcataga caagcgacaa aggaaccgat gccagtactg ccgctatcaa     780
aagtgtttgg cttgcggtat gaagcgagag cggtgcaag aggagcgcca gaggaatgct     840
cgcggcgcgg aggatgcgca cccgagtagc tcggtgcagg taagcgatga gctgtcaatc     900
gagcgcctaa cggagatgga gtctttggtg gcagatccca gcgaggagtt ccagttcctc     960
cgcgtggggc ctgacagcaa cgtgcctcca cgttaccgcg cgcccgtctc ctccctctgc    1020
caaataggca acaagcaaat agcggcgttg gtggtatggg cgcgcgacat ccctcatttc    1080
gggcagctgg agctggacga tcaagtggta ctcatcaagg cctcctggaa tgagctgcta    1140
ctcttcgcca tcgcctggcg ctctatggag tatttggaag atgagaggga gaacggggac    1200
ggaacgcgga gcaccactca gccacaactg atgtgtctca tgcctggcat gacgttgcac    1260
cgcaactcgg cgcagcaggc gggcgtgggc gccatcttcg accgcgtgct gtccgagctc    1320
agtctgaaga tgcgcacctt gcgcatggac caggccgagt acgtcgcgct caaagccatc    1380
gtgctgctca accctgatgt gaaaggactg aagaatcggc aagaagttga cgttttgcga    1440
gaaaaaatgt tctcttgcct ggacgactac tgccggcggt cgcgaagcaa cgaggaaggc    1500
cggtttgcgt ccttgctgct gcggctgcca gctctccgct ccatctcgct caagagcttc    1560
gaacacctct acttcttcca cctcgtggcc gaaggctcca tcagcggata catacgagag    1620
gcgctccgaa accacgcgcc tccgatcgac gtcaatgcca tgatgtaaag tgcgatacac    1680
gccctgccga tgtgagaaga actatggcta atagaagcga aactgaatac atctagggtg    1740
```

```
ggacttaact tgggactatc attaaagtat cacgcaaatt atgcgtagtc agaaagtcgc   1800
gtcgatcaaa cttttttata aacgaattga gtttctaacg actgcaacac agcggagttt   1860
tgcttctgat agttttttatt ctaatggtta agatgcttta cacgggcatt attgacattc   1920
aagtgtaagt ggaagttgac aaccttgaca tttatatcac gtttgtaatt ggttaaataa   1980
attaattaat cacaagtaag actaacatca acgtcacgat actaacgcca tttagtgata   2040
tttttcatgt caagaaactc attgttttga taaaatattt ttctaattac tccagtgaac   2100
tcatccaaat gtgacccagt ttcccgcaga gttgcccgtg taaaatcatc tttagggaca   2160 tatccccgc  tatctcatga aattccaagg atcagtaggg gccaattccc ccgatgtgtt   2220
gggaggcaga attttcgata atctacgact attgttagcc tacgaattag ttgaattttt   2280
tgaaattatt tttattaagt cgccactttc caaacacatc agcagggtat atgtgcaatt   2340
ttgtaacgat aactctattc atttctgata tttatcgaaa ttttatctta cataacatgc   2400
tggctggtcc aggtgtttgg tagttacata tgtatctacg gtttgtttta aattatagct   2460
tttttattgt aatctgtata aaattgagtt atcttacttc acactacgat cgagtaaacc   2520
catcgtcagc tacgaaaaac taatcgtata aggcgtaaga gtaaataact aattgacaac   2580
cagcaacgag gaccacctca gtcctcgtgc ttacattgtg ccgtagctta atatgatgga   2640
agctgtcgtc gttacgacat tagataaagt gcatgaatac caaaaatgta ccatcccgta   2700
ctgatctctc atgctctcgc tgcgtgggac ccgtgtcgag tgtcgtaagg actgactaat   2760
attttagact aggcgtctat gcttcagtaa ttccttatac atattataag tcatccaaat   2820
aacgagtaag gcggcatgtt gagatcagca ttccgagagt caaagagccc ctaacgtgac   2880
tgagaagtag agacaataca ctgattttct gagatgaacg caaccgagat tgacactaaa   2940
aatctattta tggatttcaa aatggcgatg cttgattgtc tgcggcgtgg atagactgaa   3000
atgggtttgc ttaacactgg atattgtttt tattagttaa tagtcttaca ttgcaagttg   3060
gtaattcggt gctaatatcg accggtttgt taactatcta acggttccca gtgtcaggca   3120
cacatctttc ccaagcagac aacgcaagag tgtacaaaat gtacatgtta caaaataagg   3180
aacattcgtc ggataagtgt aacagttgat aggtaaagaa aatggggccg cctctttatt   3240
attacgtagc cgtaaaatta ttaacgtatt tagtttagat gttcagctaa ttaggataat   3300
tctatttgtc gagtacctag atgtccatag tgaattaata taataattag actgttacgc   3360
gtaggtaatt ataaagttta ccaaatctct cttcaaagca aaactttgt  acacttccgt   3420 actgagacgt cgtagcttat tctgattcac gaaatatttg gatcacattg ttacaaggcg   3480
accgtcacgt agtatatgat tatttacaaa tgacacgtat gtatcaatgc tataagtgtt   3540
ttcgttacat atgtcggtgc tttaacgtgc atttcgatgt gcagattaaa aatagcaaga   3600
aatcttgaaa ttgttttaga aaatatttga tttccttatt gaaagttatt tttaaatgta   3660
aatatttcgt aatcataata attatgtatt gtgtagttat ttcacccttta cggttgggat   3720 attatttaat ggtggcctac gaaagtgatt ataaccatcc gcgtcctcaa aaaggccagt   3780 ttattttttgt acctcataca tactaattac gtaagtaata tcaggcgaat ggttgactaa   3840
caactaacca gtattaaaaa ttaaaagact tcgtcctaat aaaatgtaat atctatgtat   3900
aaaaatgaaa aatctggcgt ataataggta aaattaaact agattgttaa tgaatgtgat   3960
gtctcataaa cgtttagttt ttaatgagaa acatgtttag tcgcctacta taagacgaga   4020
cggcaagctc accgagttaa ctcgtaaaca ggaatgttga aaaagatgac acaatttata   4080
```

```
tttggtattg aaattatgac taaccatgcg ctctatcgtt tgttatggat gcatagtatt    4140
gctgttgaaa ataatggaat taggtaatta ctgcattaat gttgaaaact tgatattatt    4200
ctatggttgg gtatgaattc tatgttggaa gtgttgcagc ggttgtaaag atgatttata    4260
atgatgttca ctaaatatct gactaaatgt aagttatttt tttttgtata gacatagctt    4320
taagatgaag gtgattaaac tttatcctta tcacaataaa aaaaaaaaaa aaaaa         4375
```

<210> SEQ ID NO 52
<211> LENGTH: 472
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 52

```
Met Ser Ser Val Ala Lys Lys Asp Lys Pro Thr Met Ser Val Thr Ala
1               5                   10                  15

Leu Ile Asn Trp Ala Arg Pro Ala Pro Gly Pro Pro Gln Pro Gln
            20                  25                  30

Ser Ala Ser Pro Ala Pro Ala Ala Met Leu Gln Gln Leu Pro Thr Gln
        35                  40                  45

Ser Met Gln Ser Leu Asn His Ile Pro Thr Val Asp Cys Ser Leu Asp
    50                  55                  60

Met Gln Trp Leu Asn Leu Glu Pro Gly Phe Met Ser Pro Met Ser Pro
65                  70                  75                  80

Pro Glu Met Lys Pro Asp Thr Ala Met Leu Asp Gly Leu Arg Asp Asp
                85                  90                  95

Ala Thr Ser Pro Pro Asn Phe Lys Asn Tyr Pro Pro Asn His Pro Leu
            100                 105                 110

Ser Gly Ser Lys His Leu Cys Ser Ile Cys Gly Asp Arg Ala Ser Gly
        115                 120                 125

Lys His Tyr Gly Val Tyr Ser Cys Glu Gly Cys Lys Gly Phe Phe Lys
    130                 135                 140

Arg Thr Val Arg Lys Asp Leu Ser Tyr Ala Cys Arg Glu Glu Arg Asn
145                 150                 155                 160

Cys Ile Ile Asp Lys Arg Gln Arg Asn Arg Cys Gln Tyr Cys Arg Tyr
                165                 170                 175

Gln Lys Cys Leu Ala Cys Gly Met Lys Arg Glu Ala Val Gln Glu Glu
            180                 185                 190

Arg Gln Arg Asn Ala Arg Gly Ala Glu Asp Ala His Pro Ser Ser Ser
        195                 200                 205

Val Gln Val Ser Asp Glu Leu Ser Ile Glu Arg Leu Thr Glu Met Glu
    210                 215                 220

Ser Leu Val Ala Asp Pro Ser Glu Glu Phe Gln Phe Leu Arg Val Gly
225                 230                 235                 240

Pro Asp Ser Asn Val Pro Pro Tyr Arg Ala Pro Val Ser Ser Leu
                245                 250                 255

Cys Gln Ile Gly Asn Lys Gln Ile Ala Ala Leu Val Val Trp Ala Arg
            260                 265                 270

Asp Ile Pro His Phe Gly Gln Leu Glu Leu Asp Asp Gln Val Val Leu
        275                 280                 285

Ile Lys Ala Ser Trp Asn Glu Leu Leu Leu Phe Ala Ile Ala Trp Arg
    290                 295                 300

Ser Met Glu Tyr Leu Glu Asp Glu Arg Glu Asn Gly Asp Gly Thr Arg
```

| | | | | | | | | | | | | | | | |
|---|---|---|---|---|---|---|---|---|---|---|---|---|---|---|---|
|  |  |  | 305 |  |  |  | 310 |  |  |  | 315 |  |  |  | 320 |

Ser Thr Thr Gln Pro Gln Leu Met Cys Leu Met Pro Gly Met Thr Leu
                325                    330                 335

His Arg Asn Ser Ala Gln Gln Ala Gly Val Gly Ala Ile Phe Asp Arg
                340                    345                 350

Val Leu Ser Glu Leu Ser Leu Lys Met Arg Thr Leu Arg Met Asp Gln
                355                    360                 365

Ala Glu Tyr Val Ala Leu Lys Ala Ile Val Leu Asn Pro Asp Val
             370                   375                380

Lys Gly Leu Lys Asn Arg Gln Glu Val Asp Val Leu Arg Glu Lys Met
385                  390                    395               400

Phe Ser Cys Leu Asp Asp Tyr Cys Arg Arg Ser Arg Ser Asn Glu Glu
                405                    410               415

Gly Arg Phe Ala Ser Leu Leu Leu Arg Leu Pro Ala Leu Arg Ser Ile
                420                    425               430

Ser Leu Lys Ser Phe Glu His Leu Tyr Phe Phe His Leu Val Ala Glu
                435                    440               445

Gly Ser Ile Ser Gly Tyr Ile Arg Glu Ala Leu Arg Asn His Ala Pro
    450                    455                    460

Pro Ile Asp Val Asn Ala Met Met
465                  470

```
<210> SEQ ID NO 53
<211> LENGTH: 1404
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 53
atggacacca acatttcct gccgctcgac ttctctaccc aggtgaactc ttcgtccctc      60
aactctccaa cgggtcgagg ctccatggct gtcccctcgc tgcacccctc cttgggtccg     120
ggaatcggct ctccactggg ctcgcctggg cagctgcact ctcctatcag caccctgagc     180 tccccatca atggcatggg tccgcccttc tctgtcatca gctcccccat gggccgcac      240 tccatgtcgg tacccaccac acccacattg gcttcgggga ctggtagccc ccagctcaat     300
tcacccatga accctgtgag cagcactgag gatatcaagc cgccactagg cctcaatggc     360
gtcctcaagg ttcctgccca tccctcagga aatatggcct ccttcaccaa gcacatctgt     420
gctatctgtg gggaccgctc ctcaggcaaa cactatgggg tatacagttg tgagggctgc     480
aagggcttct tcaagaggac agtacgcaaa gacctgacct acacctgccg agacaacaag     540
gactgcctga tcgacaagag acagcggaac cggtgtcagt actgccgcta ccagaagtgc     600
ctggccatgg gcatgaagcg ggaagctgtg caggaggagc ggcagcgggg caaggaccgg     660
aatgagaacg aggtggagtc caccagcagt gccaacgagg acatgcctgt agagaagatt     720
ctggaagccg agcttgctgt cgagcccaag actgagacat acgtggaggc aaacatgggg     780
ctgaacccca gctcaccaaa tgaccctgtt accaacatct gtcaagcagc agacaagcag     840
ctcttcactc ttgtggagtg ggccaagagg atcccacact tttctgagct gcccctagac     900
gaccaggtca tcctgctacg ggcaggctgg aacgagctgc tgatcgccct cttctcccac     960
cgctccatag ctgtgaaaga tgggattctc ctggccaccg gcctgcacgt acaccggaac    1020
agcgctcaca gtgctggggt gggcgccatc tttgacaggg tgctaacaga gctggtgtct    1080
```

```
aagatgcgtg acatgcagat ggacaagacg gagctgggct gcctgcgagc cattgtcctg   1140
ttcaaccctg actctaaggg gctctcaaac cctgctgagg tggaggcgtt gagggagaag   1200
gtgtatgcgt cactagaagc gtactgcaaa cacaagtacc ctgagcagcc gggcaggttt   1260
gccaagctgc tgctccgcct gcctgcactg cgttccatcg ggctcaagtg cctggagcac   1320
ctgttcttct tcaagctcat cggggacacg cccatcgaca ccttcctcat ggagatgctg   1380
gaggcaccac atcaagccac ctag                                          1404
```

```
<210> SEQ ID NO 54
<211> LENGTH: 467
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 54
```

| | | | | | | | | | | | | | | |
|---|---|---|---|---|---|---|---|---|---|---|---|---|---|---|
| Met | Asp | Thr | Lys | His | Phe | Leu | Pro | Leu | Asp | Phe | Ser | Thr | Gln | Val | Asn |
| 1 | | | | 5 | | | | | 10 | | | | | 15 | |
| Ser | Ser | Ser | Leu | Asn | Ser | Pro | Thr | Gly | Arg | Gly | Ser | Met | Ala | Val | Pro |
| | | | 20 | | | | | 25 | | | | | 30 | | |
| Ser | Leu | His | Pro | Ser | Leu | Gly | Pro | Gly | Ile | Gly | Ser | Pro | Leu | Gly | Ser |
| | | 35 | | | | | 40 | | | | | 45 | | | |
| Pro | Gly | Gln | Leu | His | Ser | Pro | Ile | Ser | Thr | Leu | Ser | Ser | Pro | Ile | Asn |
| 50 | | | | | 55 | | | | | 60 | | | | | |
| Gly | Met | Gly | Pro | Pro | Phe | Ser | Val | Ile | Ser | Ser | Pro | Met | Gly | Pro | His |
| 65 | | | | | 70 | | | | | 75 | | | | | 80 |
| Ser | Met | Ser | Val | Pro | Thr | Thr | Pro | Thr | Leu | Gly | Phe | Gly | Thr | Gly | Ser |
| | | | | 85 | | | | | 90 | | | | | 95 | |
| Pro | Gln | Leu | Asn | Ser | Pro | Met | Asn | Pro | Val | Ser | Ser | Thr | Glu | Asp | Ile |
| | | | 100 | | | | | 105 | | | | | 110 | | |
| Lys | Pro | Pro | Leu | Gly | Leu | Asn | Gly | Val | Leu | Lys | Val | Pro | Ala | His | Pro |
| | | 115 | | | | | 120 | | | | | 125 | | | |
| Ser | Gly | Asn | Met | Ala | Ser | Phe | Thr | Lys | His | Ile | Cys | Ala | Ile | Cys | Gly |
| 130 | | | | | 135 | | | | | 140 | | | | | |
| Asp | Arg | Ser | Ser | Gly | Lys | His | Tyr | Gly | Val | Tyr | Ser | Cys | Glu | Gly | Cys |
| 145 | | | | | 150 | | | | | 155 | | | | | 160 |
| Lys | Gly | Phe | Phe | Lys | Arg | Thr | Val | Arg | Lys | Asp | Leu | Thr | Tyr | Thr | Cys |
| | | | | 165 | | | | | 170 | | | | | 175 | |
| Arg | Asp | Asn | Lys | Asp | Cys | Leu | Ile | Asp | Lys | Arg | Gln | Arg | Asn | Arg | Cys |
| | | | 180 | | | | | 185 | | | | | 190 | | |
| Gln | Tyr | Cys | Arg | Tyr | Gln | Lys | Cys | Leu | Ala | Met | Gly | Met | Lys | Arg | Glu |
| | | 195 | | | | | 200 | | | | | 205 | | | |
| Ala | Val | Gln | Glu | Glu | Arg | Gln | Arg | Gly | Lys | Asp | Arg | Asn | Glu | Asn | Glu |
| 210 | | | | | 215 | | | | | 220 | | | | | |
| Val | Glu | Ser | Thr | Ser | Ser | Ala | Asn | Glu | Asp | Met | Pro | Val | Glu | Lys | Ile |
| 225 | | | | | 230 | | | | | 235 | | | | | 240 |
| Leu | Glu | Ala | Glu | Leu | Ala | Val | Glu | Pro | Lys | Thr | Glu | Thr | Tyr | Val | Glu |
| | | | | 245 | | | | | 250 | | | | | 255 | |
| Ala | Asn | Met | Gly | Leu | Asn | Pro | Ser | Ser | Pro | Asn | Asp | Pro | Val | Thr | Asn |
| | | | 260 | | | | | 265 | | | | | 270 | | |
| Ile | Cys | Gln | Ala | Ala | Asp | Lys | Gln | Leu | Phe | Thr | Leu | Val | Glu | Trp | Ala |
| | | 275 | | | | | 280 | | | | | 285 | | | |
| Lys | Arg | Ile | Pro | His | Phe | Ser | Glu | Leu | Pro | Leu | Asp | Asp | Gln | Val | Ile |
| | | | | | 290 | | | | | 295 | | | | | 300 |

```
Leu Leu Arg Ala Gly Trp Asn Glu Leu Leu Ile Ala Ser Phe Ser His
305                 310                 315                 320

Arg Ser Ile Ala Val Lys Asp Gly Ile Leu Leu Ala Thr Gly Leu His
            325                 330                 335

Val His Arg Asn Ser Ala His Ser Ala Gly Val Gly Ala Ile Phe Asp
            340                 345                 350

Arg Val Leu Thr Glu Leu Val Ser Lys Met Arg Asp Met Gln Met Asp
            355                 360                 365

Lys Thr Glu Leu Gly Cys Leu Arg Ala Ile Val Leu Phe Asn Pro Asp
    370                 375                 380

Ser Lys Gly Leu Ser Asn Pro Ala Glu Val Glu Ala Leu Arg Glu Lys
385                 390                 395                 400

Val Tyr Ala Ser Leu Glu Ala Tyr Cys Lys His Lys Tyr Pro Glu Gln
                405                 410                 415

Pro Gly Arg Phe Ala Lys Leu Leu Leu Arg Leu Pro Ala Leu Arg Ser
            420                 425                 430

Ile Gly Leu Lys Cys Leu Glu His Leu Phe Phe Phe Lys Leu Ile Gly
            435                 440                 445

Asp Thr Pro Ile Asp Thr Phe Leu Met Glu Met Leu Glu Ala Pro His
    450                 455                 460

Gln Ala Thr
465

<210> SEQ ID NO 55
<211> LENGTH: 309
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 55
ggtgtggaaa gtccccaggc tccccagcag gcagaagtat gcaaagcatg catctcaatt      60
agtcagcaac caggtgtgga aagtccccag gctccccagc aggcagaagt atgcaaagca     120
tgcatctcaa ttagtcagca accatagtcc cgccctaac tccgcccatc ccgccctaa      180 ctccgcccag ttccgccat tctccgcccc atggctgact aattttttt atttatgcag      240 aggccgaggc cgcctcggcc tctgagctat tccagaagta gtgaggaggc ttttttggag    300
gcctaggct                                                             309

<210> SEQ ID NO 56
<211> LENGTH: 24
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 56
tatataatgg atccccgggt accg                                             24

<210> SEQ ID NO 57
<211> LENGTH: 1653
<212> TYPE: DNA
<213> ORGANISM: Artificial Sequence
<220> FEATURE:
<221> NAME/KEY: misc_feature
<223> OTHER INFORMATION: Novel Sequence
```

<400> SEQUENCE: 57

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaacgatatg ggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aaggggttgc aaaaaatttt gaacgtgcaa     420
aaaaaattac caataatcca gaaaattatt atcatggatt ctaaaacgga ttaccaggga     480
tttcagtcga tgtacacgtt cgtcacatct catctacctc ccggttttaa tgaatacgat     540
tttgtaccag agtcctttga tcgtgacaaa acaattgcac tgataatgaa ttcctctgga     600
tctactgggt tacctaaggg tgtggcccct ccgcatagaa ctgcctgcgt cagattctcg     660
catgccagag atcctatttt tggcaatcaa atcattccgg atactgcgat tttaagtgtt     720
gttccattcc atcacggttt tggaatgttt actacactcg atatttgat atgtggattt     780
cgagtcgtct taatgtatag atttgaagaa gagctgtttt tacgatccct tcaggattac     840
aaaattcaaa gtgcgttgct agtaccaacc ctattttcat tcttcgccaa agcactctg      900
attgacaaat acgattatc taatttacac gaaattgctt ctggggcgc acctctttcg      960
aaagaagtcg gggaagcggt tgcaaaacgc ttccatcttc cagggatacg acaaggatat    1020
gggctcactg agactacatc agctattctg attacacccg aggggatga taaaccgggc    1080
gcggtcggta agttgttcc attttttgaa gcgaaggttg tggatctgga taccgggaaa    1140
acgctgggcg ttaatcagag aggcgaatta tgtgtcagag acctatgat tatgtccggt    1200
tatgtaaaca atccggaagc gaccaacgcc ttgattgaca aggatggatg ctacattct    1260
ggagacatag cttactggga cgaagacgaa cacttcttca tagttgaccg cttgaagtct    1320
ttaattaaat acaaaggata tcaggtggcc cccgctgaat tggaatcgat attgttacaa    1380
caccccaaca tcttcgacgc gggcgtggca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa agttgcgcg gaggagttgt gtttgtggac    1560
gaagtaccga aaggtcttac cggaaaactc gacgcaagaa aaatcagaga gatcctcata    1620
aaggccaaga agggcggaaa gtccaaattg taa                                 1653
```

<210> SEQ ID NO 58
<211> LENGTH: 867
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 58

```
aagcgagagg cggtgcaaga ggagcgccag aggaatgctc gcggcgcgga ggatgcgcac      60
ccgagtagct cggtgcaggt aagcgatgag ctgtcaatcg agcgcctaac ggagatggag     120
tctttggtgg cagatcccag cgaggagttc cagttcctcc gcgtgggcc tgacagcaac     180
gtgcctccac gttaccgcgc gcccgtctcc tccctctgcc aaataggcaa caagcaaata     240
gcggcgttgg tggtatgggc gcgcgacatc cctcatttcg ggcagctgga gctggacgat     300
```

```
caagtggtac tcatcaaggc ctcctggaat gagctgctac tcttcgccat cgcctggcgc    360
tctatggagt atttggaaga tgagagggag aacgggacg gaacgcggag caccactcag     420
ccacaactga tgtgtctcat gcctggcatg acgttgcacc gcaactcggc gcagcaggcg    480
ggcgtgggcg ccatcttcga ccgcgtgctg tccgagctca gtctgaagat gcgcaccttg    540
cgcatggacc aggccgagta cgtcgcgctc aaagccatcg tgctgctcaa ccctgatgtg    600
aaaggactga agaatcggca agaagttgac gttttgcgag aaaaaatgtt ctcttgcctg    660
gacgactact gccggcggtc gcgaagcaac gaggaaggcc ggtttgcgtc cttgctgctg    720
cggctgccag ctctccgctc catctcgctc aagagcttcg aacacctcta cttcttccac    780
ctcgtggccg aaggctccat cagcggatac atacgagagg cgctccgaaa ccacgcgcct    840
ccgatcgacg tcaatgccat gatgtaa                                        867
```

```
<210> SEQ ID NO 59
<211> LENGTH: 225
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 59
tcgacattgg acaagtgcat tgaacccttg tctctcgaga gacaagggg ttcaatgcac      60 ttgtccaatg tcgagagaca aggggttca atgcacttgt ccaatgtcga gagacaaggg    120
ggttcaatgc acttgtccaa tgtcgagaga caagggggtt caatgcactt gtccaatgtc    180
gagagacaag ggggttcaat gcacttgtcc aatgtcgact ctaga                    225
```

```
<210> SEQ ID NO 60
<211> LENGTH: 619
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 60
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctcg tttagtgaac cgtcagatcg cctggagacg    540
ccatccacgc tgttttgacc tccatagaag acaccgggac cgatccagcc tccgcggccg    600
ggaacggtgc attggaacg                                                619
```

```
<210> SEQ ID NO 61
<211> LENGTH: 262
<212> TYPE: DNA
<213> ORGANISM: Artificial Sequence
<220> FEATURE:
<221> NAME/KEY: misc_feature
```

<223> OTHER INFORMATION: Novel Sequence

<400> SEQUENCE: 61

| | |
|---|---|
| atgtagtctt atgcaatact cttgtagtct tgcaacatgg taacgatgag ttagcaacat | 60 |
| gccttacaag gagagaaaaa gcaccgtgca tgccgatagg tggaagtaag gtggtacgat | 120 |
| cgtgccttat taggaaggca acagacgggt ctgacatgga ttggacgaac cactgaattc | 180 |
| cgcattgcag agatattgta tttaagtgcc tagctcgata caataaacgc catttgacca | 240 |
| ttcaccacat tggagtgcac ct | 262 |

<210> SEQ ID NO 62
<211> LENGTH: 1247
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 62

| | |
|---|---|
| tctatttcct caggccgtga ggaactgtcg ccagcttcaa gtataaatgg gtgcagtaca | 60 |
| gatggcgagg cacgacgtca gaagaagggc cctgcgcccc gtcagcaaga ggaactgtgt | 120 |
| ctggtatgcg gggacagagc ctccggatac cactacaatg cgctcacgtg tgaagggtgt | 180 |
| aaagggttct tcagacggag tgttaccaaa aatgcggttt atatttgtaa attcggtcac | 240 |
| gcttgcgaaa tggacatgta catgcgacgg aaatgccagg agtgccgcct gaagaagtgc | 300 |
| ttagctgtag gcatgaggcc tgagtgcgta gtacccgaga ctcagtgcgc catgaagcgg | 360 |
| aaagagaaga agcacagaa ggagaaggac aaactgcctg tcagcacgac gacggtggac | 420 |
| gaccacatgc cgcccattat gcagtgtgaa cctccacctc ctgaagcagc aaggattcac | 480 |
| gaagtggtcc caaggtttct ctccgacaag ctgttggaga caaaccggca gaaaaacatc | 540 |
| ccccagttga cagccaacca gcagttcctt atcgccaggc tcatctggta ccaggacggg | 600 |
| tacgagcagc cttctgatga agatttgaag aggattacgc agacgtggca gcaagcggac | 660 |
| gatgaaaacg aagagtctga cactcccttc cgccagatca cagagatgac tatcctcacg | 720 |
| gtccaactta tcgtggagtt cgcgaaggga ttgccagggt tcgccaagat ctcgcagcct | 780 |
| gatcaaatta cgctgcttaa ggcttgctca agtgaggtaa tgatgctccg agtcgcgcga | 840 |
| cgatacgatg cggcctcaga cagtgttctg ttcgcgaaca accaagcgta cactcgcgac | 900 |
| aactaccgca aggctggcat ggcctacgtc atcgaggatc tactgcactt ctgccggtgc | 960 |
| atgtactcta tggcgttgga caacatccat tacgcgctgc tcacggctgt cgtcatcttt | 1020 |
| tctgaccggc cagggttgga gcagccgcaa ctggtggaag aaatccagcg gtactacctg | 1080 |
| aatacgctcc gcatctatat cctgaaccag ctgagcgggt cggcgcgttc gtccgtcata | 1140 |
| tacggcaaga tcctctcaat cctctctgag ctacgcacgc tcggcatgca aaactccaac | 1200 |
| atgtgcatct ccctcaagct caagaacaga aagctgccgc ttttcct | 1247 |

<210> SEQ ID NO 63
<211> LENGTH: 440
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 63

Ser Ile Ser Ser Gly Arg Glu Glu Leu Ser Pro Ala Ser Ser Ile Asn

-continued

```
1               5                   10                  15
Gly Cys Ser Thr Asp Gly Glu Ala Arg Arg Gln Lys Lys Gly Pro Ala
                20                  25                  30
Pro Arg Gln Gln Glu Glu Leu Cys Leu Val Cys Gly Asp Arg Ala Ser
                35                  40                  45
Gly Tyr His Tyr Asn Ala Leu Thr Cys Glu Gly Cys Lys Gly Phe Phe
                50                  55                  60
Arg Arg Ser Val Thr Lys Asn Ala Val Tyr Ile Cys Lys Phe Gly His
 65                 70                  75                  80
Ala Cys Glu Met Asp Met Tyr Met Arg Arg Lys Cys Gln Glu Cys Arg
                85                  90                  95
Leu Lys Lys Cys Leu Ala Val Gly Met Arg Pro Glu Cys Val Val Pro
                100                 105                 110
Glu Thr Gln Cys Ala Met Lys Arg Lys Glu Lys Lys Ala Gln Lys Glu
                115                 120                 125
Lys Asp Lys Leu Pro Val Ser Thr Thr Thr Val Asp Asp His Met Pro
                130                 135                 140
Pro Ile Met Gln Cys Glu Pro Pro Pro Glu Ala Ala Arg Ile His
145                 150                 155                 160
Glu Val Val Pro Arg Phe Leu Ser Asp Lys Leu Leu Glu Thr Asn Arg
                165                 170                 175
Gln Lys Asn Ile Pro Gln Leu Thr Ala Asn Gln Gln Phe Leu Ile Ala
                180                 185                 190
Arg Leu Ile Trp Tyr Gln Asp Gly Tyr Glu Gln Pro Ser Asp Glu Asp
                195                 200                 205
Leu Lys Arg Ile Thr Gln Thr Trp Gln Gln Ala Asp Asp Glu Asn Glu
                210                 215                 220
Glu Ser Asp Thr Pro Phe Arg Gln Ile Thr Glu Met Thr Ile Leu Thr
225                 230                 235                 240
Val Gln Leu Ile Val Glu Phe Ala Lys Gly Leu Pro Gly Phe Ala Lys
                245                 250                 255
Ile Ser Gln Pro Asp Gln Ile Thr Leu Leu Lys Ala Cys Ser Ser Glu
                260                 265                 270
Val Met Met Leu Arg Val Ala Arg Arg Tyr Asp Ala Ala Ser Asp Ser
                275                 280                 285
Val Leu Phe Ala Asn Asn Gln Ala Tyr Thr Arg Asp Asn Tyr Arg Lys
                290                 295                 300
Ala Gly Met Ala Tyr Val Ile Glu Asp Leu Leu His Phe Cys Arg Cys
305                 310                 315                 320
Met Tyr Ser Met Ala Leu Asp Asn Ile His Tyr Ala Leu Leu Thr Ala
                325                 330                 335
Val Val Ile Phe Ser Asp Arg Pro Gly Leu Glu Gln Pro Gln Leu Val
                340                 345                 350
Glu Glu Ile Gln Arg Tyr Tyr Leu Asn Thr Leu Arg Ile Tyr Ile Leu
                355                 360                 365
Asn Gln Leu Ser Gly Ser Ala Arg Ser Ser Val Ile Tyr Gly Lys Ile
                370                 375                 380
Leu Ser Ile Leu Ser Glu Leu Arg Thr Leu Gly Met Gln Asn Ser Asn
385                 390                 395                 400
Met Cys Ile Ser Leu Lys Leu Lys Asn Arg Lys Leu Pro Pro Phe Leu
                405                 410                 415
Glu Glu Ile Trp Asp Val Ala Asp Met Ser His Thr Gln Pro Pro Pro
                420                 425                 430
```

```
Ile Leu Glu Ser Pro Thr Asn Leu
        435                 440

<210> SEQ ID NO 64
<211> LENGTH: 943
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 64
atgacttcga aagtttatga tccagaacaa aggaaacgga tgataactgg tccgcagtgg      60
tgggccagat gtaaacaaat gaatgttctt gattcattta ttaattatta tgattcagaa     120
aaacatgcag aaaatgctgt tatttttta catggtaacg cggcctcttc ttatttatgg      180
cgacatgttg tgccacatat tgagccagta gcgcggtgta ttataccaga ccttattggt     240
atgggcaaat caggcaaatc tggtaatggt tcttataggt tacttgatca ttacaaatat     300
cttactgcat ggtttgaact tcttaattta ccaaagaaga tcatttttgt cggccatgat     360
tggggtgctt gtttggcatt tcattatagc tatgagcatc aagataagat caaagcaata     420
gttcacgctg aaagtgtagt agatgtgatt gaatcatggg atgaatggcc tgatattgaa     480
gaagatattg cgttgatcaa atctgaagaa ggagaaaaaa tggttttgga gaataacttc     540
ttcgtggaaa ccatgttgcc atcaaaaatc atgagaaagt tagaaccaga agaatttgca     600
gcatatcttg aaccattcaa agagaaaggt gaagttcgtc gtccaacatt atcatggcct     660
cgtgaaatcc cgttagtaaa aggtggtaaa cctgacgttg tacaaattgt taggaattat     720
aatgcttatc tacgtgcaag tgatgattta ccaaaaatgt ttattgaatc ggacccagga     780
ttcttttcca atgctattgt tgaaggtgcc aagaagtttc ctaatactga atttgtcaaa     840
gtaaaaggtc ttcattttc gcaagaagat gcacctgatg aaatgggaaa atatatcaaa     900
tcgttcgttg agcgagttct caaaaatgaa caataattct aga                      943
```